(12) United States Patent
Forage et al.

(10) Patent No.: US 6,613,891 B1
(45) Date of Patent: Sep. 2, 2003

(54) POLYNUCLEOTIDES THAT ENCODE BOVINE INHIBIN

(75) Inventors: Robert Gregory Forage, Chatswood (AU); Andrew George Stewart, Sydney (AU); David Mark Milne-Robertson, Glen Waverley (AU); David Moritz de Kretser, Surrey Hills (AU); John Kerr Findlay, Mont Albert (AU)

(73) Assignee: Inhibin Pty. Limited, Thornleigh (AU)

( * ) Notice: Subject to any disclaimer, the term of this patent is extended or adjusted under 35 U.S.C. 154(b) by 0 days.

(21) Appl. No.: 08/478,696

(22) Filed: Jun. 7, 1995

Related U.S. Application Data

(63) Continuation of application No. 08/347,214, filed on Nov. 16, 1994, now abandoned, which is a continuation of application No. 07/866,340, filed on Apr. 9, 1992, now abandoned, which is a continuation of application No. 07/336,099, filed on Apr. 11, 1989, now abandoned, which is a continuation of application No. 06/852,523, filed on Apr. 16, 1986, now abandoned.

(30) Foreign Application Priority Data

| Apr. 18, 1985 | (AU) | PH0194 |
|---|---|---|
| Sep. 6, 1985 | (AU) | PH2320 |
| Sep. 29, 1985 | (AU) | PH3157 |
| Dec. 19, 1985 | (AU) | PH3960 |
| Dec. 20, 1985 | (AU) | PH3961 |

(51) Int. Cl.$^7$ ............... C12N 15/11; C12N 15/12; C12N 15/00; C12N 5/10
(52) U.S. Cl. ............ 536/23.5; 536/23.1; 536/24.3; 536/24.31; 530/350; 435/69.1; 435/252.3; 435/320.1; 435/455; 435/471
(58) Field of Search ............ 530/387.1, 388.24, 530/350; 435/70.21, 240.27, 69.1, 252.3; 536/23.1, 23.5

(56) References Cited

U.S. PATENT DOCUMENTS

| 4,399,216 A | | 8/1983 | Axel et al. | |
|---|---|---|---|---|
| 4,624,944 A | | 11/1986 | Li et al. | |
| 4,636,463 A | * | 1/1987 | Altman et al. | 435/7 |
| 4,643,969 A | | 2/1987 | Inouye et al. | |
| 4,717,666 A | | 1/1988 | Brawner et al. | |
| 4,737,578 A | | 4/1988 | Evans et al. | |
| 4,740,587 A | | 4/1988 | Ling et al. | |
| 4,742,003 A | * | 5/1988 | Derynck et al. | 435/68 |
| 4,798,885 A | | 1/1989 | Mason et al. | |
| 4,864,019 A | * | 9/1989 | Vale et al. | 530/387 |
| 5,011,691 A | | 4/1991 | Opperman et al. | |
| 5,102,807 A | | 4/1992 | Burger et al. | |

FOREIGN PATENT DOCUMENTS

| AU | 86/0009 | 1/1986 |
|---|---|---|
| EP | 0222491 | 5/1987 |
| WO | 00119 | 6/1985 |
| WO | 8600078 | 1/1986 |

OTHER PUBLICATIONS

Robertson DM et al 1985 Biochem. Biophys. Res. Comm. 126(1): 220–225.*
Sahni G. et al 1981 Andrologia 14(5):403–408.*
Dayloff et al., *Att. of Protein Seq. and Structure*, 5:88–89 (1972).
Pongor, S., *Methods in Epyg.*, 154:450–473 (1987).
Jaye et al., *NAR*, 11(8):2325 (1983).
Gordon et al., "Beta–Microseminoprotein (β–MSP is not an Inhibin," *Biology of Reproduction*, 36:829–835 (1987).
Albert B., *Molecular Biology of the Cell*, 185–196 (1983).
Wood et al., *Proc. Nat. Acad. Sci.*, 82:1585–1588 (Mar. 1985).
Sleggs et al., *Proc. Nat. Acad. Sci.*, 78(11):6613–6617 (1981).
Wooley, *J. Am. Board of Family Prac.*, 4(3):159–166 (1991).
Mason et al., "Complementary DNA Sequences of Ovarian . . . ," *Nature*, 318:659–663 (1985).
McCullagh, D.R., "Dual Endocrine Activity of the Testes," *Science*, 76:19–20 (1932).
deJong, F.H., "Inhibin–Fact or Artifact," *Molecular and Cellular Endocrinology*, 13:1–13 (1979).
Seidah et al., "Partial Amino Acid Sequences of a Human . . . ," *FEBS Letters*, 167:98–102 (1984).
Seidah et al., "Complete Amino Acid Sequence of Human . . . ," *FEBS Letters*, 175:349–355 (1984).
Sheth et al., "Characterization oa a polypeptide from Human . . . ," *FEBS Letters*, 165:11–15 (1984).
Beksac et al., "Evidence for the Prostatic Origin of Immi-noreactive . . . ," *Intl. J. of Andrology* 7:389–397 (1984).
Laemmli et al., "Cleavage of Structural Proteins During . . . ," *Nature*, 227:680–685 (1970).
Lilja et al., "Amino Acid Sequence of the Predominant . . . ," *FEBS Letters*, 182:181–184 (1985).
Scott et al., "A Simple and Rapid In Vitro Bioassay . . . ," *Endocrinology*, 107:1536–1542 (1980).
Au et al., "In Vitro Bioassay of Inhibin in Testes . . . ," *Endocrinology*, 112:239–244 (1983).
Reid et al., "A Simple Apparatus for Vertical Flat–Sheet Polyacrylamide . . . ," *Analytical Biochem.*, 22:374–381 (1968).

(List continued on next page.)

*Primary Examiner*—Phillip Gambel
(74) *Attorney, Agent, or Firm*—Foley & Lardner

(57) ABSTRACT

Recombinant nucleic acid molecules encoding 58 kD, 43 kD, 31 kD, 20 kD and 15 kD bovine inhibin and bovine inhibin subunits are disclosed. Vectors, host cells comprising recombinant nucleic acid molecules encoding bovine inhibin and bovine inhibin subunits are disclosed. In addition, methods for producing bovine inhibin and bovine inhibin subunits are disclosed.

38 Claims, 20 Drawing Sheets

OTHER PUBLICATIONS

Hunkapiller et al., "Analysis of Phenylthiohydantoin . . . ," *Methods in Enzymology*, 91:486–493 (1983).

O'Farrell, P., "High Resolution Two–Dimensional . . . ," *J. Biol. Chem.*, 250:4007–4021 (1975).

Vaitukaitis et al., "A Method for Producing Specific Antisera . . . ," *J. Clini. Endocrin. and Metab.* 33:988–991 (1971).

Bolton et al., "The Labeling of Proteins to High Specific . . . ," *Biochemistry* 133:529–539 (1973).

Peterson et al., "Separation of Bound From Free Hormone . . . ," *Clin. Chem.*, 25:1239–1241 (1979).

Mougdal et al., "Regulation of FSH Secretion . . . ," *Gonadal Proteins and Peptides and Their Biological Significance*, (Salram Ed.), 21–37 (1984).

Henderson et al., "Increase in Ovulation Rate After Active Immunization," *J. Endocrinol.*, 102:305–309 (1984).

Cummins et al., "Increased Ovulation Rate in the Ewe . . . ," *Proc. Aust. Soc. Reprod. Biol.* 15:81 (1983).

Al–Obaidi et al., "Advancement of Puberty in Ewe Lambs . . . ," *Proc. Aust. Soc. Reprod. Biol.* 15:80 (1983).

Gemzell, C., "Induction of Ovulation with Human Gonadotropins . . . ," *Hormone Res.* 21:179–204 (1965).

Bardin et al., "The Testes," *Textbook of Endocrinology*, Williams Eds. pp. 293–354 (1981).

Cummins, L., Thesis, University of New England, Armidale, Australia, pp. 160–166 (1983).

Ross et al., "The Ovaries and the Breasts,"0 *Textbook of Endocrinology*, Williams Eds. pp. 355–411 (1981).

Cepko et al. "Construction and Applications of a Highly Transmissible . . . ," *Cell*, 37:1053–1062 (1984).

Graham et al., "A New Technique for the Assay of Infectivity of Human Adenovirus 5 DNA," *Virology*, 52:456–467 (1973).

Parker et al., "Regulation of Simian Virus 40 Transcription: Sensivite Analysis . . . ," *J. of Virology*, 31:360–369 (1979).

Thomas, P.S., "Hybridization of Denatured RNA and Small DNA Fragments . . . ," *Proc. Natl. Acad. Sci.*, 77:5201–5205 (1980).

McLachlan et al., "The Radioimmunoassay of Bovine and Human Follicular . . . ," *Molec. and Cell. Endocr.*, 46:175–185 (1986).

Briand et al., "Synthetic Peptides as Antigens: Pitfalls of Conjugation Methods," *J. Immunol. Methods* 78:59–69 (1985).

Chari et al., "Biological Characteristics of Inhibin . . . ," *Int. Cong, Ser. Excerp. Med. 551 (Human Repro.*), 463–467 (1981).

deJong et al., "Purification, Characterization and Physiological Significance of Inhibin . . . ," *Adv. Biosci.*, 34:73–84 (1982).

Sevier et al., "Monoclonal Antibodies in Clinical Immunology," *Clin. Chem.*, 27:1797–1806 (1981).

Sheth et al., "Interaction of Thyrotrophin Releasing Hormone With Inhibin . . . ," *J. Endocrinology*, 98:1–6 (1983).

Dobos et al., "Isolation of Inhibin From Follicular Fluid . . . ," *Molecular and Cellular Endocrinology* 31:187–198 (1983).

Franchimont et al., "Inhibin: From Concept to Reality," *Vitamins and Hormones*, 37:243–302 (1979).

deJong et al., "Inhibin: 1985 Update on Action . . . ," *Molecular and Cellular Endocrinology* 42:95–103 (1985).

Astedt et al., "Purification of a Special Placental Plasminogen Activator . . . ," *Thrombosis and Haemostasis*, 122–125 (1985).

Ye et al., "cDNA Cloning and Expression in *E. Coli* of a Plasminogen . . . ," *J. Biol. Chem.*, 262:3718–3725 (1987).

Begent et al., "Liposomally Entrapped Second Antibody Improves Tumor . . . ," *The Lancet*, 2:739–741 (1974).

Ellouz et al., "Minimal Structural Requirements . . . ," *Bioch. and Biophys. Res. Comm.*, 59:1317–1325 (1974).

Lowry et al., "Protein Measurement with the Folin Phenol . . . ," *J. Biol. Chem.*, 193:265–275 (1951).

Bradford, M.M., "A Rapid and Sensitive Method for the Quantiation . . . ," *Analytical Biochem.*, 72:248–254 (1976).

Merril et al., "Ultrasensitive Stain for Proteins in Polyacrylamide Gels . . . ," *Science*, 211:1437–1438 (1981).

Botterman et al., "High Level of Production of the $EcoR_1$, Endonuclease Under . . . ," *Gene*, 37:229–239 (1985).

Joyce et al., "Construction of a Plasmid That Overproduces the Large . . . ," *Proc. Natl. Acad. Sci.*, 80:1830–1834 (1983).

Tessier et al., "The Influance of mRNA Primary and Secondary Structure . . . ," *Nucleic Aicds Research*, 12:7663–7675 (1984).

Mott et al., "Maximizing Gene Expression From Plasmid Vectors Containing . . . ," *Proc. Natl. Acad. Sci.*, 82:88–92 (1985).

Van Doren et al., "Infection of Eucaryotic Cells by Helper–Independent . . . ," *J. Virology*, 50:606–614 (1984).

Robertson et al., "Isolation of Inhibin From Bovine . . . ," *Biochem. and Biophys. Res. Comm.*, 126(1):220–226 (1985).

Miyamota et al., "Isolation of Porcine Follicular Fluid . . . ," *Biochem. and Biophys. Res. Comm.*, 129(2):396–403 (1985).

Ling et al., "Isolation and Partial Characterization . . . ," *Proc. Natl. Acad. Sci.*, 82:7217–7221 (1985).

Rivier et al., "Purification and Partial Characterization of Inhibin . . . ," *Biochem. & Biophy. Res. Comm.*, 133:120–127 (1987).

Fukuda et al., "Isolation of Bovine Follicular Fluid . . . ," *Molecular and Cellular Endocr.*, 44:55–60 (1986).

Mason et al, "Structure of Two Human Ovarian Inhibins," *Biochem. & Biophy. Res. Comm.*, 135:957–964 (1986).

Forage et al., "Cloning and Sequence Analysis of cDNA . . . ," *Proc. Natl. Acad. Sci.*, 83:3091–3095 (1986).

McLachlan et al., "Plasma Inhibin Levels During Gonadotropin–Induced . . . ," *The Lancet*, 1:1233–1234 (1986).

de Kretser et al., "Control of FSH and LH Secretion," *Monograph of Endocrin.—The Pituitary* . . . , 25:12–43 (1983).

Au et al., "Relationship Between Testicular Inhibin . . . ," *J. Reprod. Fert.*, 72:351–536 (1984).

Robertson et al., "The Effect of Inhibin Purified From Bovine . . . ," *Molecular and Cellular Endocr.*, 46:29–36 (1986).

de Krestser et al., "Inhibin Becomes Reality," *Research in Reproduction*, 18:1–4 (1986).

de Kretser et al., "Morphology and Physiology of the Testis," *Principles and Pract. of Endocr. and Metabol.*, Chapter 116 928–937.

McLachlan et al., "Circulating Immunoactive Inhibin in the Luteal Phase . . . ," *Fertility and Sterility*, 48:1001–1005 (1987).

Esch et al., "Peptides of Gonadal Origin Involved . . . ," Role Dept. Proteins Control Reprod. Proc. Workshop McCann (Ed), 275–290 (1983).

Li et al., "Human Seminal Alpha Inhibins . . . " *Proc. Natl. Acad. Sci.*, 82:4041–4044 (1985).

Baker et al., "Assays of Inhibin," *Academic Press London*, Intragonadal Regul. Reprod. 193–228 (1981).

Baker et al., "Studies on the Purification of Ovine Inhibin," Ann NY Acad Sci 383: 329–342 (1982).

Robertson et al., "The Use of 51Cr For Assessing Cytotoxicity in an In Vitro Bioassay For Inhibin," Endocrinol. 26:119–127 (1982).

O'Shea et al., "Ovarian Activity in Ewes Vaccinated with an Inhibin Enriched Fraction . . . ," Proc. Aust. Soc Rep. Biol 15:22 (1983).

Chirgwin et al., "Isolation of Biologically Active Ribonucleic Acid . . . ," Biochemistry 18:5294–5299 (1979).

Aviv et al., "Purification of Biologically Active Globin Messenger RNA . . . ," PNAS 39:1408–1412 (1972).

Locker, J., "Analytical and Preparative Electrophoresis of RNA in Agrose–Urea," Anal Biochem 98:353–367 (1979).

Gubler et al., "A Simple adn Very Efficient Method For Generating cDNA Libraries." Gene 25:263–269 (1983).

Hanahan et al., "Studies on Transformation of *Escherichia Coli* With Plasmids," J. Mol. Bio. 166:557–558 (1983).

Clewell, D.B., "Nature of Col E1 Plasmid Replication in *Escherichia Coli* . . . ," *J. Bacteriol.*, 667–676 (1972).

Hanshan et al., "Plasmid Screening at High Colony Density," Gene 10: 63–67 (1980).

Grunstein et al., "Colony Hybridization: A Method For The Isolation of Cloned DNAs That Contain a Specific Gene" PNAS 72:3961–3965 (1975).

Matteucci et al., "Synthesis of Deoxyoligonucleotides On A Polymer Support," J. Amer. Chem Soc 103:3185–3191 (1981).

Birnboim et al., "A Rapid Alkaline Extraction Procedure For Screening Recombinant . . .," Nuc. Acids 7:1513–1523 (1979).

Sanger et al., "DNA Sequencing With Chain Terminating Inhibitors," PNAS 74:5463–5467 (1977).

Murry et al., "Lamboid Phages That Simplify the Recovery of In Vitro Recombinants," Mol. Gen. Genes 150:53–61 (1977).

Bolivar et al., "Construction Characterization of New Cloning Vehicles: II A Multipurpose Cloning System," Gene 2:95–113 (1977).

Ruther et al., "Easy Identification of cDNA Clones," EMBO J 2:1791–1794 (1983).

Vieria et al., "The PUC Plasmids, An M13mp7–Derived System For Insertion Mutagenisis . . . ," Gene 19:259–268 (1982).

Watson, M.E.E., "Compilation of Published Signal Sequences," Nucl. Acids Res 12:5145–5154 (1984).

Steiner et al., "Processing Mechanisms In The Biosynthesis of Proteins," Ann N.Y. Acad Sci 343:1–16 (1980).

Wagh et al., Crit. Rev Biochem 10:"Sugar Residues on Proteins," 307–377 (1981).

Pierce et al., "Glycoprotein Hormones: Structure and Function," Ann Rev Biochem 52:465–495 (1981).

Nevins, J.R., "The Pathway of Eukaryotic mRNA Formation," Ann Rev Biochem 52:441–466 (1983).

Jacobs et al., "Isolation and Characterization of Genomic and cDNA Clones of Human Erythropoietin," Nature 313:806–810 (1985).

Feinberg et al., "A Technique for Radiolabelling DNA Restriction Endonuclease . . . ," Anal. Biochem 137:266–267 (1984).

Loenen et al., "A Bacteriophage Lambda Vector for Cloning Large DNA Fragments . . . ," Gene 20:249–259 (1980).

McCarthy et al., "Improved Computer Program Data for the Resolution and Fractionation . . . ," Anal. Biochem. 61:165–185 (1974).

Lazure et al., "Proteases and Post–Translational Processing of Prohormones," Eur. J. Biochem Cell Biology 61:501–515 (1985).

Derynck et al., "Human Transforming Growth Factor–B Complementary DNA Sequence . . . ," Nature 316:701–705 (1985).

Towbin et al., "Electrophoretic Transfer of Proteins from Plyacrylamide Gels . . . ," PNAS 76:4350–4354 (1979).

Mattick et al., "The Isolation and Characterization of Fatty Acid Synthetase mRNA . . . ," Eur. J. Biochem 114:643–651 (1980).

Nilsson et al., "Efficient Secretion and Purification of Human Insulin–Like Growth Factor–1 . . . ," Nucl. Acid Res 13:1151–1152 (1985).

Edman et al., "Synthesis of Hepatitis B Surface and Core Antigens in *E. Coli*," Nature 29:503–506 (1981).

Tacon et al., "The Construction and Characterization of Plasmid Vectors Suitable . . . ," Molec. Gen Genes 177:427–438 (1980).

Nagai et al., "Generation of B–Globulin By Sequence Specific Proteolysis of a Hybrid Protein . . . ," Nature 309:810–812 (1984).

Germino et al., "Rapid Purification of a Cloned Gene Product by Genetic Fusion and Site–Specific Proteolysis," PNAS 81:4692–4694(1984).

Bethell et al., "A Novel Method of Activation of Cross–Linked Agroses With 1,1'–Carbonyl . . . ," J. Biol. Chem. 254:2572–2574 (1979).

Douglass et al., "Polyprotein Gene Expression: Generation of Diversity of Neuroendocrine Peptides," Ann Rev Biochem 53:665–715 (1984).

Marana et al., "Influence of the Purity of Icoinated Tracer on the Specificity . . . ," Acta Endocrinol 92:585–594 (1979).

Twigg et al., "Trans–Complementable Copy–Number Mutants of Plasmid Co1E1," Nature 283:216–218 (1980).

Bradbury et al., "Mechanism of C–Terminal Amide Formulation By Pituitary Enzymes," Nature 298:686–688 (1982).

Frischauf et al., "Lambda Replacement Vectors Carrying Polylinker Sequences," J. Mol. Biol 170:827–842 (1983).

* cited by examiner

FIG. 3A

PROBES FOR THE 43 kD SUBUNIT

| Position | | 4 | 5 | 6 | 7 | 8 | |
|---|---|---|---|---|---|---|---|
| Amino Acid | | Gly | Gly | Phe | Met | Arg | |
| Probe 1 | 3' | CCN | CCN | AA<sup>A</sup><sub>G</sub> | TAC | C<sup>T</sup><sub>G</sub> | 5' |

(Probe 1: 3'  CCN  CCN  AA(A/G)  TAC  C(T/G)  5', where Phe codon has A/G and Arg codon has T/G)

| Position | | -10 | -9 | -8 | -7 | -6 | -5 | |
|---|---|---|---|---|---|---|---|---|
| Amino Acid | | Asp | Pro | Gly | Val | Arg | Arg | |
| Probe 3 | 3' | A | GGA | CCT | CAG | TCC | GCA | 5' |

| Position | | 217 | 218 | 219 | 220 | 221 | 222 | |
|---|---|---|---|---|---|---|---|---|
| Amino Acid | | Pro | Pro | Ser | Phe | Ile | Leu | |
| Probe 4 | 5' | CCT | CCC | AGT | TTC | ATC | T | 3' |

FIG. 3B

PROBES FOR THE 15 kD SUBUNIT

| Position | | 20 | 21 | 22 | 23 | 24 | |
|---|---|---|---|---|---|---|---|
| Amino Acid | | Phe | Lys | Asp | Ile | Gly | |
| Probe 2 | 3' | AA(A/G) | TT(T/C) | CT(A/G) | TAG(A/T) | CC | 5' |

(Probe 2: 3'  AA(A/G)  TT(T/C)  CT(A/G)  TA(A/T)G  CC  5')

| Position | | 5 | 6 | 7 | 8 | 9 | 10 | |
|---|---|---|---|---|---|---|---|---|
| Amino Acid | | Asp | Gly | Lys | Val | Asn | Ile | |
| Probe 5 | 3' | CTG | CC(C/G) | TTC | CA(C/G) | TTG | TA | 5' |

| Position | | -173 | -172 | -171 | -170 | -169 | -168 | -167 | -166 |
|---|---|---|---|---|---|---|---|---|---|
| Amino Acid | | Xaa | Phe | Glu | Ile | Ser | Lys | Glu | Gly |
| Probe 6 | 5' | C | TTT | GAG | ATT | TCC | AAA | GAA | GGC  3' |

Where the probes are DNA sequences in which  A = adenine
C = cytosine
G = guanine
T = thymine
N = A,C,G or T

FIG. 5A

```
 1:          ccctggcaga aggggcacag ggcagggtgt gggttcccag tgggcagggc caggggagct
           -60           Pvu II                   -50
 61:     ATG TGG CTT CAG CTG CTC CTC TTG CTG CTG GCC CCT CAG GGC GGG CAT GGC TGT
         Met Trp Leu Gln Leu Leu Leu Leu Leu Leu Ala Pro Gln Gly Gly His Gly Cys
             -40              -35            Bal I                          -25
115:     CAT GGG CTG GAG CTG GAC CGG GAA CTT GTC CTG GCC AAG GTG AGG GCC CTG TTT
         His Gly Leu Glu Leu Asp Arg Glu Leu Val Leu Ala Lys Val Arg Ala Leu Phe
                    -20              -15                  Sau 3a I
169:     CTG GAT GCC TTG GGG CCC CCA CCG GTG ACT GGG GAA GGT GGA GAT CCT GGA GTC
         Leu Asp Ala Leu Gly Pro Pro Pro Val Thr Gly Glu Gly Gly Asp Pro Gly Val
              -5             Sph I               5                  10
223:     AGG CGT CTG CAC CGG AGG CAT GCC GTG GGG GGC TTC ATG CGC AGG GGC TCT GAG
         Arg Arg Leu His Arg Arg His Ala Val Gly Gly Phe Met Arg Arg Gly Ser Glu
                                      20                       Pst I      Pvu
277:     CCC GAG GAC CAA GAT GTC TCC CAG GCC ATC CTT TTT CCG GCT GCA GGT GCC AGC
         Pro Glu Asp Gln Asp Val Ser Gln Ala Ile Leu Phe Pro Ala Ala Gly Ala Ser
         II                           40
331:     TGC GGG GAT GAG CCA GAT GCT GGA GAG GCT GAG GAG GGC CTC TTC ACG TAT GTG
         Cys Gly Asp Glu Pro Asp Ala Gly Glu Ala Glu Glu Gly Leu Phe Thr Tyr Val
              50                                    60              Pvu II
385:     TTC CAG CCA TCC CAG CAC ACA CGC AGC CGC CAG GTG ACT TCG GCC CAG CTG TGG
         Phe Gln Pro Ser Gln His Thr Arg Ser Arg Gln Val Thr Ser Ala Gln Leu Trp
                    70                                 80
439:     TTC CAC ACA GGA CTG GAC AGA CAG GAG ACC GCT GCC GCC AAC AGC TCT GAG CCC
         Phe His Thr Gly Leu Asp Arg Gln Glu Thr Ala Ala Ala Asn Ser Ser Glu Pro
            85             Rsa I            95         *        100
493:     CTG CTT GGC CTG CTG GTA CTG ACA TCC GGG GGT CCC ATG CCT GTG CCC ATG TCG
         Leu Leu Gly Leu Leu Val Leu Thr Ser Gly Gly Pro Met Pro Val Pro Met Ser
                                110               Bal I          120
547:     CTG GGC CAG GCC CCC CCT CGC TGG GCT GTC CTG CAC CTG GCC ACC TCC GCC TTC
         Leu Gly Gln Ala Pro Pro Arg Trp Ala Val Leu His Leu Ala Thr Ser Ala Phe
                      125          Hae II                135
601:     CCT CTG CTG ACC CAT CCT GTC CTG GCG CTC CTG CGT TGT CCT CTC TGT TCC
         Pro Leu Leu Thr His Pro Val Leu Ala Leu Leu Arg Cys Pro Leu Cys Ser
              140                              150
655:     TGC TCC ACT CGG CCC GAA GCC ACC CCC TTC CTG GTG GCC CAC ACA CGG GCC AAG
         Cys Ser Thr Arg Pro Glu Ala Thr Pro Phe Leu Val Ala His Thr Arg Ala Lys
              160                   Hae II          170
709:     CCG CCC AGT GGA GGG GAG AGG GCC CGG CGC TCC ACG CCC CCA CTG CCC TGG CCT
         Pro Pro Ser Gly Gly Glu Arg Ala Arg Arg Ser Thr Pro Pro Leu Pro Trp Pro
```

FIG. 5B

```
                          180        Pst I  Stu I              190
763: TGG TCT CCC GCT GCG CTG CGC CTG CTG CAG AGG CCT CCA GAG GAG CCC GCC GCC
     Trp Ser Pro Ala Ala Leu Arg Leu Leu Gln Arg Pro Pro Glu Glu Pro Ala Ala
                                200                                       210
817: CAT GCC GAC TGC CAC AGA GCC GCC CTC AAT ATC TCC TTC CAG GAG CTG GGC TGG
     His Ala Asp Cys His Arg Ala Ala Leu Asn Ile Ser Phe Gln Glu Leu Gly Trp
                                          *
                                         220
871: GAC CGG TGG ATA GTG CAC CCT CCC AGT TTC ATC TTC TAC TAC TGT CAT GGG GGG
     Asp Arg Trp Ile Val His Pro Pro Ser Phe Ile Phe Tyr Tyr Cys His Gly Gly
             230                                  240         Sma I
925: TGT GGG CTG TCC CCC CCA CAG GAC CTG CCC CTG CCG GTC CCC GGG GTG CCT CCT
     Cys Gly Leu Ser Pro Pro Gln Asp Leu Pro Leu Pro Val Pro Gly Val Pro Pro
                      250                                 260
979: ACC CCT GTC CAG CCC CTC TCT CTG GTC CCA GGG GCC CAG CCC TGT TGC GCT GCC
     Thr Pro Val Gln Pro Leu Ser Leu Val Pro Gly Ala Gln Pro Cys Cys Ala Ala
         Sma I           270                                      280
1033: CTC CCG GGA ACC ATG AGG CCC CTA CAC GTC CGC ACC ACC TCG GAT GGA GGT TAC
      Leu Pro Gly Thr Met Arg Pro Leu His Val Arg Thr Thr Ser Asp Gly Gly Tyr
                                     290                                300
1087: TCT TTT AAG TAT GAG ATG GTG CCC AAC CTT CTC ACC CAG CAC TGT GCT TGC ATC
      Ser Phe Lys Tyr Glu Met Val Pro Asn Leu Leu Thr Gln His Cys Ala Cys Ile

1141: TAA gggaatc ccgctgtgac AATAAAtgac atagtgcata tg poly(A)
      ***
```

FIG. 5C

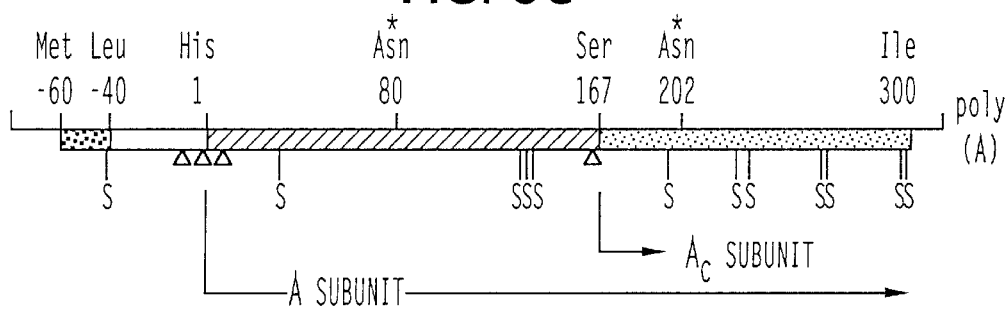

FIG. 6A

```
          -170                                      -160
  1: TTT GAG ATT TCC AAA GAA GGC AGT GAC CTG TCC GTG GTG GAA CGT GCA GAA ATC
     Phe Glu Ile Ser Lys Glu Gly Ser Asp Leu Ser Val Val Glu Arg Ala Glu Ile
                    -150                                      -140
 55: TGG CTC TTC CTG AAA GTT CCC AAG GCC AAC AGG ACC CGG AGC AAA GTC ACC ATC
     Trp Leu Phe Leu Lys Val Pro Lys Ala Asn Arg Thr Arg Ser Lys Val Thr Ile
                                                 *
                        -130       Pst I                          -120
109: CGT CTC TTT CAA CAG CAG AAG CAC CTG CAG GGC AGC TTG GAT GCA GGG GAG GAG
     Arg Leu Phe Gln Gln Gln Lys His Leu Gln Gly Ser Leu Asp Ala Gly Glu Glu
                              -110                          Eco RV
163: GCT GAG GAA GTG GGC TTG AAG GGG GAA AAG AGT GAA ATG TTG ATA TCG GAG AAG
     Ala Glu Glu Val Gly Leu Lys Gly Glu Lys Ser Glu Met Leu Ile Ser Glu Lys
         -100                                -90              Pvu II
217: GTG GTG GAT GCT CGG AAG AGC ACC TGG CAC ATC TTC CCT GTC TTC AGC TGC ATC
     Val Val Asp Ala Arg Lys Ser Thr Trp His Ile Phe Pro Val Ser Ser Cys Ile
         Hae II        -78            Sst I              -70
271: CAG CGC TTG CTG GAC CAG GGC AAG AGC TCC CTG GAC ATA CGG ATT GCC TGT GAG
     Gln Arg Leu Leu Asp Gln Gly Lys Ser Ser Leu Asp Ile Arg Ile Ala Cys Glu
                       -60                                      -50
325: CAG TGT CAG GAG ACC GGC GCA AGC CTG GTG CTC CTG GGC AAG AAG AAG AAG AAA
     Gln Cys Gln Glu Thr Gly Ala Ser Leu Val Leu Leu Gly Lys Lys Lys Lys Lys
                             -40                                  -30
379: GAA GAG GAG GGG GAA GGG AAG AAG AGG GAT GGA GAA GGA GGG GCG GGA GGG GAC
     Glu Glu Glu Gly Glu Gly Lys Lys Arg Asp Gly Glu Gly Gly Ala Gly Gly Asp
                                 -20           Pst I
433: GAG GAG AAG GAG CAG TCG CAC AGA CCT TTC CTC ATG CTG CAG GCC CGC CAG TCT
     Glu Glu Lys Glu Gln Ser His Arg Pro Phe Leu Met Leu Gln Ala Arg Gln Ser
          -10              Hae II      -1   1                       Hin
487: GAA GAC CAT CCT CAC CGG CGC CGG CGG CGG GGC CTG GAG TGT GAC GGC AAG GTC
     Glu Asp His Pro His Arg Arg Arg Arg Arg Gly Leu Glu Cys Asp Gly Lys Val
     dII  10                              20                  25
541: AAC ATC TGC TGT AAG AAA CAG TTC TTT GTT AGT TTC AAG GAC ATT GGC TGG AAT
     Asn Ile Cys Cys Lys Lys Gln Phe Phe Val Ser Phe Lys Asp Ile Gly Trp Asn
        Sau 3A I          35                       40
595: GAC TGG ATC ATT GCT CCC TCC GGC TAC CAC GCC AAC TAC TGT GAG GGT GAG TGC
     Asp Trp Ile Ile Ala Pro Ser Gly Tyr His Ala Asn Tyr Cys Glu Gly Glu Cys
                        50                  55              Taq I
649: CCC AGC CAC ATA GCA GGC ACA TCG GGC TCA TCC CTC TCC TTT CAC TCG ACG GTC
     Pro Ser His Ile Ala Gly Thr Ser Gly Ser Ser Leu Ser Phe His Ser Thr Val
```

FIG. 6B

```
                Sph I        70                                    80
703:   ATC AAC CAC TAC CGC ATG CGG GGC CAC AGC CCC TTC GCC AAC CTC AAG TCG TGC
       Ile Asn His Tyr Arg Met Arg Gly His Ser Pro Phe Ala Asn Leu Lys Ser Cys
                                   90       Rsa I
757:   TGT GTG CCC ACC AAG CTG AGA CCC ATG TCC ATG TTG TAC TAT GAC GAT GGG CAG
       Cys Val Pro Thr Lys Leu Arg Pro Met Ser Met Leu Tyr Tyr Asp Asp Gly Gln
            100             105         Sau 3A I                 115
811:   AAC ATC ATC AAG AAG GAC ATC CAG AAC ATG ATC GTG GAG GAG TGT GGT TGC TCA
       Asn Ile Ile Lys Lys Asp Ile Gln Asn Met Ile Val Glu Glu Cys Gly Cys Ser

Hae II
865:   TAG agc gcccagcctg gggggggatgg gagcgagacg gtccagagaa gacagtggtg
       ***

921:   acacgaagac atgtttaagg tttctgactg aaacaacc poly(A)
```

FIG. 6C

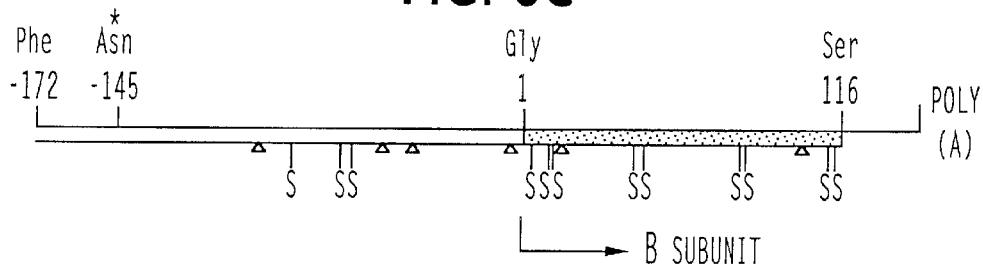

FIG. 7A

```
                -60
  1: tgagctc ATG GTG CTG CAC CTA CTG CTC TTC TTG CTG CTG ACC CCA CAG GGT GGG
             Met Val Leu His Leu Leu Leu Phe Leu Leu Leu Thr Pro Gln Gly Gly
                    -40                                  -30
 56: CAC AGC TGC CAG GGG CTG GAG CTG GCC CGG GAA CTT GTT CTG GCC AAG GTG AGG
     His Ser Cys Gln Gly Leu Glu Leu Ala Arg Glu Leu Val Leu Ala Lys Val Arg
                -20                                  -10
110: GCC CTG TTC TTG GAT GCC TTG GGG CCC CCC GCG GTG ACC AGG GAA GGT GGG GAC
     Ala Leu Phe Leu Asp Ala Leu Gly Pro Pro Ala Val Thr Arg Glu Gly Gly Asp
                                -1  1
164: CCT GGA GTC AGG CGG CTG CCC CGA AGA CAT GCC CTG GGG GGC TTC ACA CAC AGG
     Pro Gly Val Arg Arg Leu Pro Arg Arg His Ala Leu Gly Gly Phe Thr His Arg
         10                                  20
218: GGC TCT GAG CCC GAG GAA GAG GAG GAT GTC TCC CCA GCC ATC CTT TTC CCA GCC
     Gly Ser Glu Pro Glu Glu Glu Glu Asp Val Ser Gln Ala Ile Leu Phe Pro Ala
                 30                                  40
272: ACA GAT GCC AGC TGT GAG GAC AAG TCA GCT GCC AGA GGG CTG GCC CAG GAG GCT
     Thr Asp Ala Ser Cys Glu Asp Lys Ser Ala Ala Arg Gly Leu Ala Gln Glu Ala
                     50                                  60
326: GAG GAG GGC CTC TTC AGA TAC ATG TTC CGG CCA TCC CAG CAT ACA CGC AGC CGC
     Glu Glu Gly Leu Phe Arg Tyr Met Phe Arg Pro Ser Gln His Thr Arg Ser Arg
                             70                                  80
380: CAG GTG ACT TCA GCC CAG CTG TGG TTC CAC ACC GGG CTG GAC AGG CAG GGC ACA
     Gln Val Thr Ser Ala Gln Leu Trp Phe His Thr Gly Leu Asp Arg Gln Gly THr
                                 90
434: GCA GCC TCC AAT AGC TCT GAG CCC CTG CTA GGC CTG CTG GCA CTG TCA CCG GGA
     Ala Ala Ser Asn Ser Ser Glu Pro Leu Leu Gly Leu Leu Ala Leu Ser Pro Gly
         100                                 110
488: GGA CCC GTG GCT GTG CCC ATG TCT TTG GGC CAT GCT CCC CCT CAC TGG GCC GTG
     Gly Pro Val Ala Val Pro Met Ser Leu Gly His Ala Pro Pro His Trp Ala Val
             120                                 130
542: CTG CAC CTG GCC ACC TCT GCT CTC TCT CTG CTG ACC CAC CCC GTC CTG GTG CTG
     Leu His Leu Ala Thr Ser Ala Leu Ser Leu Leu Thr His Pro Val Leu Val Leu
                 140                                 150
596: CTG CTG CGC TGT CCC CTC TGT ACC TGC TCA GCC CGG CCT GAG GCC ACG CCC TTC
     Leu Leu Arg Cys Pro Leu Cys Thr Cys Ser Ala Arg Pro Glu Ala Thr Pro Phe
                             160                                 170
650: CTG GTG GCC CAC ACT CGG ACC AGA CCA CCC AGT GGA GGG GAG AGA GCC CGA CGC
     Leu Val Ala His Thr Arg Thr Arg Pro Pro Ser Gly Gly Glu Arg Ala Arg Arg
                                     180
704: TCA ACT CCC CTG ATG TCC TGG CCT TGG TCT CCC TCT GCT CTG CGC CTG CTG CAG
     Ser Thr Pro Leu Met Ser Trp Pro Trp Ser Pro Ser Ala Leu Arg Leu Leu Gln
```

FIG. 7B

```
     190                                                200
758: AGG CCT CCG GAG GAA CCG GCT GCC CAT GCC AAC TGC CAC AGA GTA GCA CTG AAC
     Arg Pro Pro Glu Glu Pro Ala Ala His Ala Asn Cys His Arg Val Ala Leu Asn
              210                                               220
812: ATC TCC TTC CAG GAG CTG GGC TGG GAA CGG TGG ATC GTG TAC CCT CCC AGT TTC
     Ile Ser Phe Gln Glu Leu Gly Trp Glu Arg Trp Ile Val Tyr Pro Pro Ser Phe
                             230                                240
866: ATC TTC CAC TAC TGT CAT GGT GGT TGT GGG CTG CAC ATC CCA CCA AAC CTG TCC
     Ile Phe His Tyr Cys His Gly Gly Cys Gly Leu His Ile Pro Pro Asn Leu Ser
                                     250                                260
920: CTT CCA GTC CCT GGG GCT CCC CCT ACC CCA GCC CAG CCC TAC TCC TTG CTG CCA
     Leu Pro Val Pro Gly Ala Pro Pro Thr Pro Ala Gln Pro Tyr Ser Leu Leu Pro
                                             270
974: GGG GCC CAG CCC TGC TGT GCT GCT CTC CCA GGG ACC ATG AGG CCC CTA CAT GTC
     Gly Ala Gln Pro Cys Cys Ala Ala Leu Pro Gly Thr Met Arg Pro Leu His Val
      280                                         290
1028: CGC ACC ACC TCG GAT GGA GGT TAC TCT TTC AAG TAT GAG ACA GTG CCC AAC CTT
      Arg Thr Thr Ser Asp Gly Gly Tyr Ser Phe Lys Tyr Glu Thr Val Pro Asn Leu
           300
1082: CTC ACG CAG CAC TGT GCT TGT ATC TAA ggg tgggggggtct tccttcttaa tcc
      Leu Thr Gln His Cys Ala Cys Ile ***
```

FIG. 8

```
                   -10                                              -1  1
  1: GCC CGG CAG TCT GAA GAC CAC CCT CAT CGC CGG CGT CGG CGG GGC TTG GAG TGT
     Ala Arg Gln Ser Glu Asp His Pro His Arg Arg Arg Arg Arg Gly Leu Glu Cys
                        10                                      20
 55: GAT GGC AAG GTC AAC ATC TGC TGT AAG AAA CAG TTC TTT GTC AGT TTC AAG GAC
     Asp Gly Lys Val Asn Ile Cys Cys Lys Lys Gln Phe Phe Val Ser Phe Lys Asp
                             30                                          40
109: ATC GGC TGG AAT GAC TGG ATC ATT GCT CCC TCT GGC TAT CAT GCC AAC TAC TGC
     Ile Gly Trp Asn Asp Trp Ile Ile Ala Pro Ser Gly Tyr His Ala Asn Tyr Cys
                                      50
163: GAG GGT GAG TGC CCG AGC CAT ATA GCA GGC ACG TCC GGG TCC TCA CTG TCC TTC
     Glu Gly Glu Cys Pro Ser His Ile Ala Gly Thr Ser Gly Ser Ser Leu Ser Phe
              60                                      70
217: CAC TCA ACA GTC ATC AAC CAC TAC CGC ATG CGG GGC CAT AGC CCC TTT GCC AAC
     His Ser Thr Val Ile Asn His Tyr Arg Met Arg Gly His Ser Pro Phe Ala Asn
                   80                                       90
270: CTC AAA TCG TGC TGT GTG CCC ACC AAG CTG AGA CCC ATG TCC ATG TTG TAC TAT
     Leu Lys Ser Cys Cys Val Pro Thr Lys Leu Arg Pro Met Ser Met Leu Tyr Tyr
                        100                                     110
325: GAT GAT GGT CAA AAC ATC ATC AAA AAG GAC ATT CAG AAC ATG ATC GTG GAG GAG
     Asp Asp Gly Gln Asn Ile Ile Lys Lys Asp Ile Gln Asn Met Ile Val Glu Glu

379: TGT CGG TGC TCA TAG agttg cccagcccag ggggaaaggg agcaaga
     Cys Arg Cys Ser ***
```

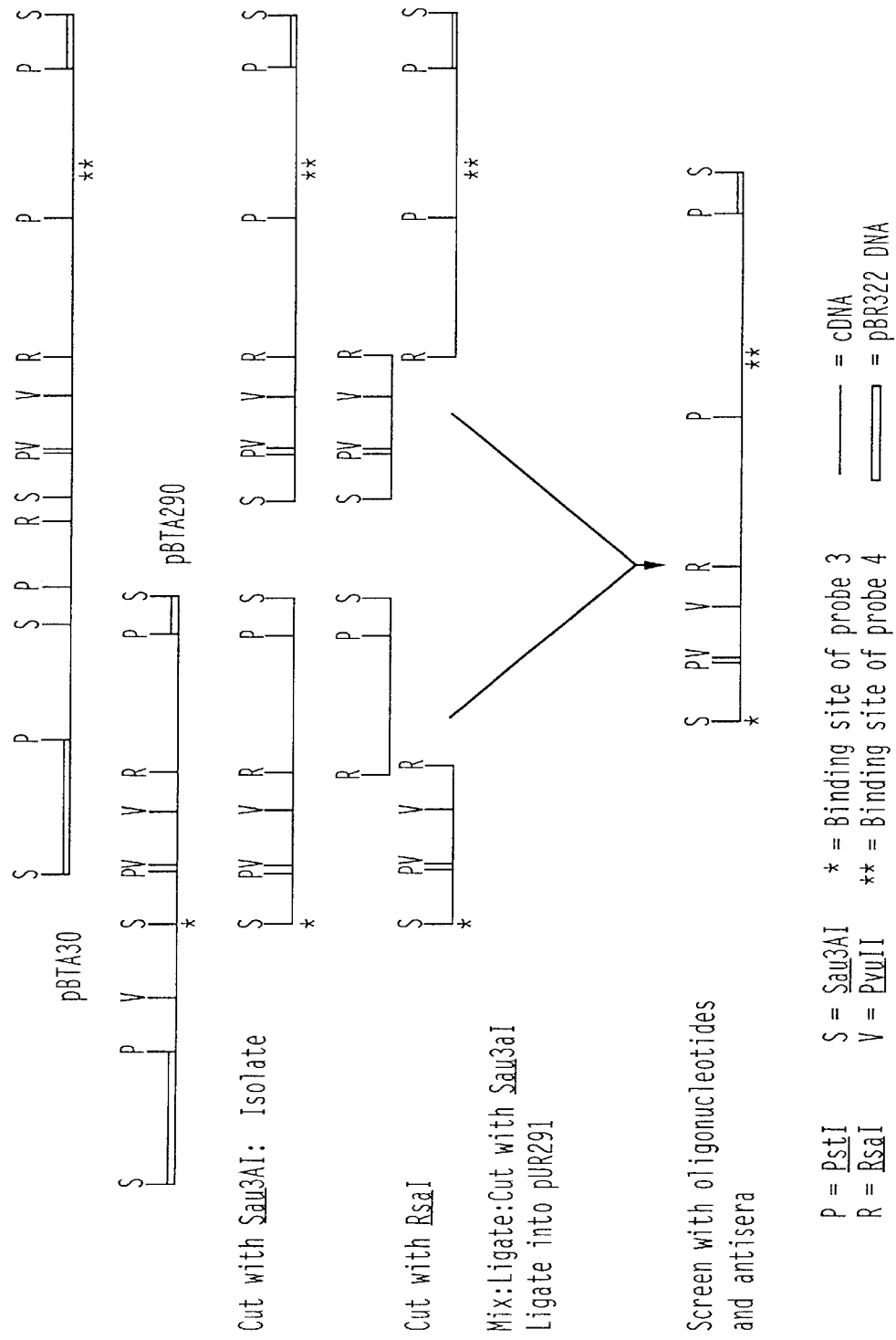

FIG. 11A

LINKERS FOR EXPRESSION OF THE A SUBUNIT

Sph I SITE LINKERS

```
    Linkers    5'          GATCCGAAGCTTGCATCGATTATGCATG              3'
               3'              GCTTCGAACGTAGCTAATAC                  5'
```

Spliced 5' End

```
                                                     1   2   3
                    Asp Pro Lys Leu Ala Ser Ile Met His Ala Val
               5'   GAT CCG AAG CTT GCA TCG ATT ATG CAT GCC GTG       3'
               3'       GC TTC GAA CGT AGC TAA TAC GTA CGG CAC       5'
                      BamHI  HindIII    ClaI           SphI
```

Pvu II SITE LINKERS

```
    Linkers    5'          GATCCGAAGCTTATGTGGCTTCAG                  3'
               3'              GCTTCGAATACACCGAAGTC                  5'
```

Spliced 5' End

```
                                         -60 -59 -58 -57 -56 -55
                    Asp Pro Lys Leu Met Trp Leu Gln Leu Leu
               5'   GAT CCG AAG CTT ATG TGG CTT CAG CTG CTC          5'
               3'       GC TTC GAA TAC ACC GAA GTC GAC GAG          3'
                      BamHI  HindIII              PvuII
```

Hae II SITE LINKERS

```
    Linkers    5'   GATCCGGCATCGATTATGCGGCGC                         3'
               3'       GCCGTAGCTAATACGCGC                           5'
```

Spliced 5' End

```
                                        165 166 167 168
                    Asp Pro Ala Ser Ile Met Arg Arg Ser Thr
               5'   GAT CCG GCA TCG ATT ATG CGG CGC TCC ACG          3'
               3'       GC CGT AGC TAA TAC GCC GCG AGG TGC           5'
                      BamHI     ClaI           HaeII
```

FIG. 11B

LINKERS FOR EXPRESSION OF THE B SUBUNIT

Hae II Site Linkers

```
LINKERS        5'  GATCCGGCATCGATTATGCGGCGC                              3'
               3'      GCCGTAGCTAATACGC                                  5'

Spliced 5' End                          -5  -4  -3  -2  -1   1
                   Asp Pro Ala Ser Ile Met Arg Arg Arg Arg Arg Gly
               5' GAT CCG GCA TCG ATT ATG CGG CGC CGG CGG CGG GGC        3'
               3'     GC CGT AGC TAA TAC GCC GCG GCC GCC GCC CCG         5'
                  BamHI       ClaI           HaeII
```

Hind II site linkers

```
LINKERS        5'  GATCCGGCATCGATTATGGGCCTGGAGTGTGACGGCAAGGTC             3'
               3'      GCCGTAGCTAATACCCGGACCTCACACTGCCGTTCCAG             5'

Spliced 5' End                          1   2   3   4   5   6   7   8   9  10
                   Asp Pro Ala Ser Ile Met Gly Leu Glu Cys Asp Gly Lys Val Asn Ile
               5' GAT CCG GCA TCG ATT ATG GGC CTG GAG TGT GAC GGC AAG GTC AAC ATC   3'
               3'     GC CGT AGC TAA TAC CCG GAC CTC ACA CTG CCG TTC CAG TTG TAG   5'
                  BamHI       ClaI       HaeIII                         HindII
```

Where the LINKERs are DNA sequences in which A = adenine
C = cytosine
G = guanine
T = thymine

FIG. 12

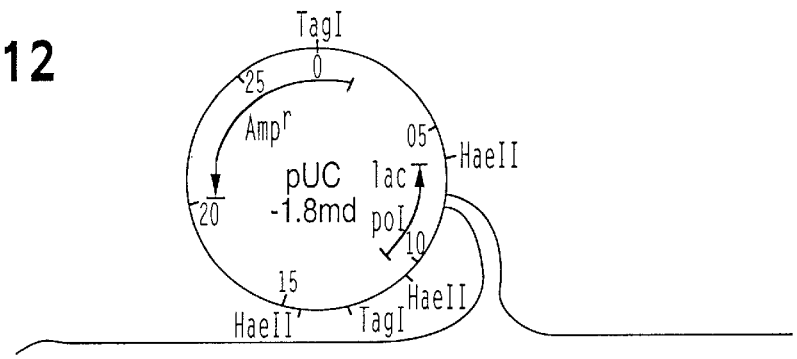

```
                                          -10 -9 -8 -7
          Met Thr Met Ile Thr Asn Ser Pro Asp Pro Gly Val
pBTA302   ATG ACC ATG ATT ACG AAT TCC CCG GAT CCT GGA GTC └────//────
                           EcoRI    BamHI 297 298 299 300
          Cys Ala Cys Ile ***
          ┘TGC GCT TGC ATC TAA GGGAAT Poly(C)CTGCAG ══GATCCGGGGAATTC
                                                PstI     Sau3A   EcoRI
```

```
          Met Thr Met Ile Thr Pro Ser Leu Gly Cys Arg Ser Thr
pBTA303   ATG ACC ATG ATT ACG CCA AGC TTG GGC TGC AGG TCG ACT
                              HINDIII    PstI    SalI
                                                   165 166 167 168
          Leu Glu Asp Pro Ala Ser Ile Met Arg Arg Ser Thr
          CTA GAG GAT CCC GCA TCG ATT ATG CGG CGC TCC ACG └───//────┘
          XbaI BamHI      ClaI 297 298 299 300
          Cys Ala Cys Ile ***
          TGC GCT TGC ATC TAA GGGAAT poly(C)CTGCAG══GATCCGATCCCCGGGCGAGCTCGAATTC
                                                   Sau3AI SmaI     SacI   EcoRI
```

```
                                          -16 -15 -14 -13
          Met Thr Met Ile Thr Asn Ser Arg Gly Ser Val Asp Leu Gln Ala Arg
pBTA304   ATG ACC ATG ATT ACG AAT TCC CGG GGA TCC GTC GAC CTG CAG GCC CGC └──//──
                              EcoRI    SmaI    BamHI   SalI    PstI 113 114 115 116
          Cys Gly Cys Ser ***
          ┘TGT GGT TGC TCA TAG └─//─┘poly(A)poly(C)CTGCAGCCAAGCTT
                                                    PstI    HindIII
```

└──//──┘ = Inhibin subunit sequences       ══ = pBR322 bases 3615-3671

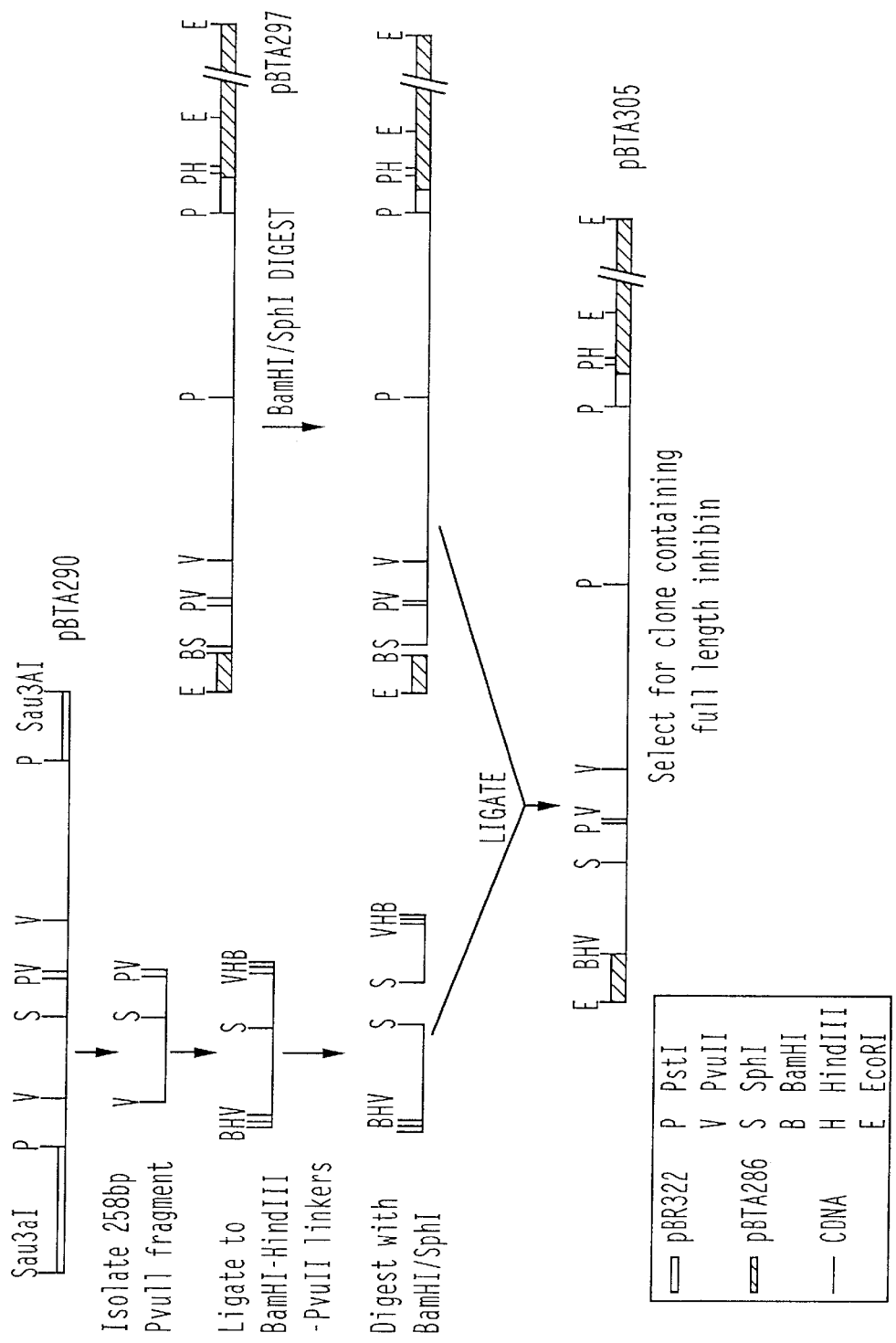

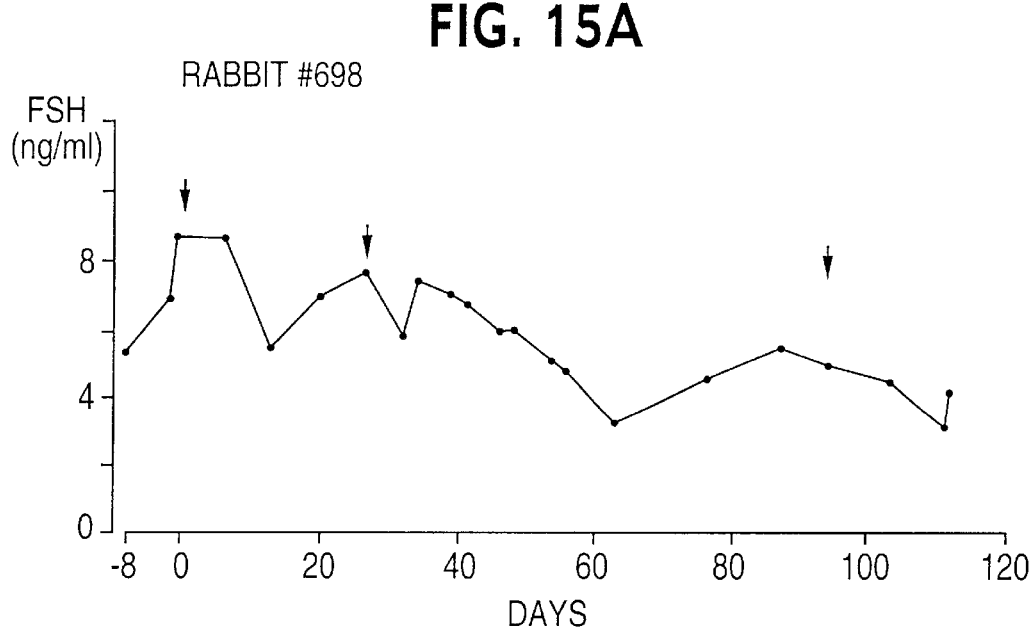
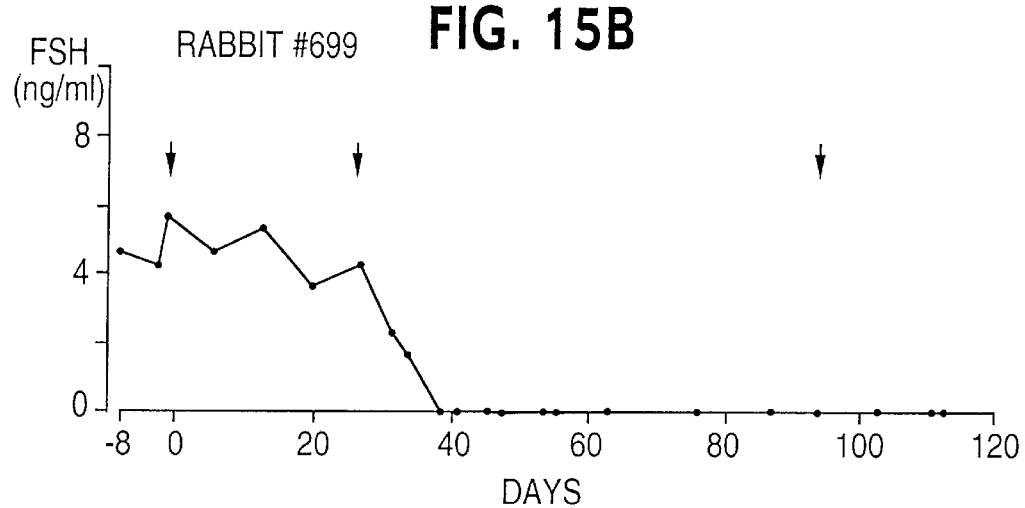

POLYNUCLEOTIDES THAT ENCODE BOVINE INHIBIN

This application is a continuation of application Ser. No. 08/347,214, filed Nov. 16, 1994, now abandoned which is a continuation of Ser. No. 07/866,340, filed Apr. 9, 1992, now abandoned which is a continuation of Ser. No. 07/336,099, filed Apr. 11, 1989, now abandoned, which is a continuation of Ser. No. 06/852,523, filed Apr. 16, 1986, now abandoned.

TECHNICAL FIELD

This invention relates, inter alia, to the construction of cloning vectors that contain deoxyribonucleic acid (DNA) sequences which code for part or all of the hormone inhibin, and of host cells such as bacterial strains containing such vectors, and of host cells such as bacterial strains which produce part, all or precursors of inhibin. In addition it relates to the production and uses of expression products of said vectors and strains and to the production and uses of fragments of the expression products and vectors, be they natural or synthetic in origin.

BACKGROUND ART

It was suggested in 1932 that the gonads produce a non-steroidal factor called inhibin which is involved in feedback regulation of pituitary function (McCullagh, D. R. (1932) Science 76, 19–20). Since that time, it has been shown that the anterior pituitary produces at least two gonadotrophins, follicle stimulating hormone or follitropin (FSH) and luteinising hormone or lutropin (LH) which together regulate the development and functioning of the gonads. Sensitive radioimmunoassays have permitted accurate independent monitoring of each hormone and have shown feedback regulation of these hormones by the gonads. The feedback regulation of LH appears to be predominantly via steroids whereas that of FSH is via the protein or glycoprotein factor, inhibin, in addition to steroids.

Inhibin can now be defined as a protein or glycoprotein hormone secreted from the granulosa cells in the ovary or Sertoli cells in the testis. It is secreted in response to FSH and acts on the pituitary as a feedback inhibitor of FSH synthesis and secretion but which leaves the basal synthesis and secretion of LH largely intact. Whether inhibin, its mRNA or precursors are formed in other cells and tissues is not yet known.

Since the early 1970's a number of attempts have been made to purify inhibin from a variety of gonadal sources, both testicular and ovarian, and with conflicting results (de Jong, F. H. (1979) Mol. Cell. Endocrinol. 13, 1–10) due in part to the use of a variety of bioassay systems where any suppression of FSH in pituitary cells in vitro or in vivo was assumed to be due to inhibin and checks were not always made for non-specific toxic effects of the test substances (Baker, H. W. G. et al. (1981) in Intragonadal Regulation of Reproduction (Franchimont, P. and Channing, C. P. Eds.), Academic Press, London pp. 193–228; Baker H. W. G. et al., (1982) Ann. New York Acad. Sci. 383, 329–342).

Recently, inhibin from bovine follicular fluid (bFF) has been purified to homogeneity. (International Patent Application PCT/AU85/00119; Robertson, D. M. et al., (1985) Biochem. Biophys. Res. Commun. 126, 220–226). This achievement was aided by the use of a rigorous cultured rat pituitary cell assay (Scott, R. S. et al., (1980) Endocrinol. 107, 1536–1542) which incorporates a means of assessing the cytotoxic effects of the substances under test (Robertson, D. M. et al., (1982) Mol. Cell. Endocrinol. 26, 119–127) so that non-specific toxic effects that lowered the FSH content of the cells under measurement could be identified as distinct from the effects of inhibin. The standard employed was a bovine follicular fluid preparation with an inhibit activity of 20 U/ml in terms of a previously described ovine testicular lymph standard assigned an arbitary activity of 1 U/mg (Scott, R. S. et al., (1980) Endocrinol. 107, 1536–1542)

The inhibin from bFF was purified about 3,500-fold to a specific activity of 200,000 units/mg protein and is a protein of 58 kD composed of two disulphide-linked subunits A and B of approximately 43 kD and 15 kD respectively as evidenced from electrophoresis in polyacrylamide gels in the presence of sodium dodecylsulphate (SDS-PAGE). The amino acid sequences for the $NH_2$-terminus of each subunit have been determined. This purified substance has the in vitro physiological properties defined earlier as those of inhibin, namely inhibiting the synthesis and release of endogenous FSH from rat pituitary cells whilst leaving intact the synthesis and release of LH prolactin and thyroid stimulating hormone.

Since FSH is important for determining the incidence and rate of ovulation in females and spermatogenesis in males, it follows that the main potential applications of inhibin, analogues, or homologues of inhibin or antibodies against inhibin will be to inhibit or to stimulate gonadal function in man and domestic animals and as diagnostic tools for analysis of gonadal function. Many experiments have been performed in vivo using crude or partially fractionated gonadal extracts or secretions in attempts to analyse the physiological effects of inhibin. Effects attributed to be due to the inhibin or antibodies against inhibin in these experiments include 1. Inhibition of gonadal function (Moudgal, N. R. et al. (1985) in Gonadal Proteins and Peptides and their Biological Significance (Sairam, M. R. and Atkinson, L. E., Eds.) World Scientific Publishing Co., Singapore, pp 21–37).
2. An increase in ovulation rate (O'Shea, T. et al., (1982) Proc. Aust. Soc. Rep. Biol. 14, 85; O'Shea, T. et al. (1983) Proc. Aust. Soc. Rep. Biol. 15, 22; Henderson, K. M. et al., (1984) J. Endocrinol. 102, 305–309).
3. An advancement of the onset of puberty (Al-Obaidi, F. A. R. et al., (1983) Proc. Aust. Soc. Rep. Biol. 15, 80).

The commercial exploitation of these properties and further physiological studies in live animals require large quantities of pure inhibin or fragments thereof or inhibin agonists and antagonists whether of natural or synthetic origin. Such quantities cannot be obtained solely by the present methods of purification since source material may be limited (e.g. human follicular fluid) and a typical extraction starting with 50 ml bFF yields only 5–10 µg of purified material.

The present invention seeks, inter alia, to overcome these limitations by the identification and characterisation of the genes which code inhibin so as to allow the molecular cloning of genes or parts of genes coding for inhibin into a host such as *Escherichia coli* and by manipulating the cloned genes or parts thereof to create hosts, such as bacterial strains, which can synthesise all, part or precursors of the inhibin molecule, including subunits thereof.

DESCRIPTION OF THE INVENTION

In a first embodiment the present invention provides a first DNA sequence which acts as a coding sequence for amino acid sequences of all, part of precursors of inhibin, or a DNA sequence which hybridises to said first DNA sequence, said sequences being from whatever source obtained, including natural, synthetic or semi-synthetic sources, said sequences including sequences related by mutation, including single or multiple base substitutions, deletions, insertions, and inversions and including DNA sequences which on expression code for all, part or precursors or homologues and analogues of a polypeptide which is inhibin or which displays similar immunological or biological activity as that of inhibin.

Preferred sequences of the invention are those coding for a polypeptide corresponding to the 43 kD and 15 kD (A and B) subunits of bovine and human inhibin as described hereinafter in more detail and depicted in FIGS. 5, 6, 7 and 8 of the accompanying drawings.

In another preferred embodiment, the DNA codes for the 20 kD ($A_C$) subunit of inhibin described hereinafter.

The DNA sequences embraced by the present invention can be prepared for example from vertibrate cells by extracting total DNA therefrom and isolating the sequences by standard techniques. Alternatively the DNA may be prepared in vitro, synthetically or biosynthetically, such as by the use of an mRNA terplate.

Also, within the scope of the present invention, is a process for selecting a DNA or RNA sequence coding for all, part or precursors of a polypeptide which is inhibin or which displays an immunological or biological activity similar to inhibin, which process comprises providing one or more DNA or RNA sequences, and determining which of said sequences hybridises with a DNA or RNA sequence known to code for a part, all or precursors of polypeptides having such an activity or providing an antiserum to inhibin or part thereof and identifying host-vector combinations that express part or all of inhibin.

The above sequence may be from natural sources, may be RNA sequences, synthetic sequences, DNA sequences from recombinant DNA molecules and combinations of such sequences.

In a preferred form of the present invention the process used to identify and characterise DNA coding for at least a portion of the protein inhibin involves the extraction of mRNA species from inhibin-producing cells, their conversion to double stranded DNA (complementary DNA or cDNA) and the insertion of these into an autonomously replicating factor, such as a plasmid. This is followed by transformation of a host cell such as a bacterial strain with the factor and screening of the library produced with synthetic DNA probes which are complementary to inhibin-like mRNA or DNA sequences in order to detect those clones which contain DNA coding for inhibin as opposed to any other cell protein.

Therefore, in another form the present invention provides synthetic polynucleotide probes for the identification of inhibin-like mRNa or DNA which probes comprise a polynucleotide and a label, the said polynucleotide having a sequence selected from:

```
                          T   G
    Probe 1    5'      C CAT AANCCNCC           3'
                          G   A A A T  A
    Probe 2    5'      CCGAT TC TT AA           3'
                          T G C  G Probe 3    5'      ACGCCTGACTCCAGGA         3'
```

-continued

```
    Probe 4    5'      CCTCCCAGTTTCATCT         3'

C     C
    Probe 5    5'      ATGTT ACCTT CCGTC        3'
                              G     G Probe 6    5'      CTTTGAGATTTCCAAAGAAGGC   3'
```

Preferably the label is a $^{32}PO_4$ group attached to the 5' end, or other label.

In a further embodiment the invention provides recombinant DNA molecules characterised by a DNA insert comprising a first DNA sequence which codes for amino acid sequences of all, part or precursors of inhibin or a DNA sequence which hybridises with said first sequence, said sequences being derived from whatever source including natural, synthetic, biosynthetic or semisynthetic sources and which sequences include those related by mutation, single or multiple base substitutions, deletions, insertions and inversions and including sequences which code for all, part or precursors, analogues or homologues of a polypeptide which is inhibin or which displays similar immunological or biological activity to inhibin.

Preferred recombinant DNA molecules of the invention include an expression control sequence operatively linked to said DNA insert. In one preferred form of the invention, the said DNA insert is operatively linked to the β-galactosidase gene of *E.coli,* Other preferred control systems include those of the tryptophan (trp) operon, the leftward promoter of bacteriophage λ ($P_L$) and hybrid promoters such as tac or viral promoters such as that of the long terminal repeat of Moloney leukaemia virus.

A preferred recombinant DNA molecule of the present invention is a plasmid which contains a DNA insert as described above. Preferred plasmids of the present invention will be described in detail hereinafter and include pBTA22, pBTA23, pBTA28, pBTA29, pBTA30, pBTA290 and pBTA292–pBTA305.

Alternatively, said recombinant DNA molecules may comprise said DNA insert linked to DNA of a suitable bacteriophage such as bacteriophage λ or to DNA of a virus capable of replicating in an eukaryotic cell in vitro or in whole organisms.

The invention also provides a fused gene comprising a promoter, a translation start signal, and a first DNA sequence which corresponds to or, on expression, codes for an amino acid sequence of all, part or precursors of a polypeptide which is inhibin or which has similar immunological or biological activity to inhibin, a DNA sequence which hybridises with said first sequence or a DNA sequence related by mutation, single or multiple base substitution, deletions, insertions and inversions to said first DNA sequence.

Preferred recombinant DNA molecules of the present invention comprise a plasmid into which has been inserted a DNA sequence comprising DNA of the present invention. Suitable plasmids include pBR322, pUR290, pUR291 or pUR292 or pBTA286, pUC7, pUC8 or pUC9 or pUC13 or ptrpL1 or pWT111, pWT121 or pWT131 and derivatives thereof. Also included are viral vectors such as pZIP Neo SV(X)1, vaccinia viruses, baculoviruses and derivatives thereof.

Also embraced within the present invention is a process for the manufacture of a recombinant DNA molecule, which process comprises providing a DNA insert comprising first DNA sequence which corresponds to or, upon expression codes for an amino acid sequence of all, part, analogues, homologues or precursors of a polypeptide which is inhibin or which has similar immunological or biological activity to inhibin, a DNA sequence which hybridises with said first sequence or a sequence related by mutation, single or multiple base substitutions, deletions, insertions and inversions to said first DNA sequence or hybridising sequence; introducing into a cloning vehicle said DNA insert.

Preferably said DNA sequence is introduced into the cloning vehicle in correct spacing and correct reading frame is essential reading frame with an expression control sequence.

In a further embodiment of the present invention there is provided a host transformed with at least one recombinant DNA molecule of the present invention and capable of expressing all, part or parts, or precursors of the polypeptide inhibin or a polypeptide having similar immunological or biological activity to inhibin.

Suitable hosts include bacterial cells, bacteriophages, yeasts, other fungi, vertebrate cells or insect cells, plant cells including human cells, human tissue cells or whole eukaryotic organisms.

Suitable bacterial hosts include *E.coli* and other enteric organisms, Pseudomonas and Bacillus. Preferred host cultures are identified as: *E. coli* BTA545, BTA634, BTA637, BTA647 and BTA652 and host-vector combinations as: ATCC67054–ATCC67059 and BTA1361.

Also included within the scope of the present invention is a process for transforming a host which process comprises: providing a suitable host, introducing into said host a recombinant DNA molecule of the present invention in correct reading frame.

The invention further provides expression products of the transformed host of the present invention which products comprise all, part or precursors are of a polypeptide which is inhibin or a polypeptide having similar immunological or biological properties of inhibin. Preferably these expression products are provided in substantially pure form.

In a preferred embodiment of the present invention, the expression products comprise a first polypeptide sequence homologous to the host and a second polypeptide sequence which is the amino acid sequence coding for all, part or precursors, analogous or homologues of a polypeptide which is inhibin or which has similar immunological or biological properties to inhibin.

In a preferred embodiment of the present invention, the first amino acid sequence is part or all of β-galactosidase and the host cell is *E.coli*. In a further preferred embodiment of the invention, the first sequence is the $NH_2$-terminal sequence of the expression product.

In a further embodiment of the present invention there is provided a process for the biosynthesis of a polypeptide which comprises all, part or precursors of inhibin or a polypeptide having similar immunological or biological activity, which process comprises: tranforming a suitable host with a recombinant DNA molecule of the present invention so that the host is capable of expressing a proteinaceous product which includes a polypeptide which is all, part of a precursor of inhibin or a polypeptide having similar biological or immunological activity; culturing said host to obtain said expression; and collecting said polypeptide.

In a preferred embodiment, the polynucleotide sequence codes on expression for a polypeptide selected from the group consisting of –60 to 166 amino acid sequence of FIG. 5, the –10 to 166 amino acid sequence of FIG. 5, the 1 to 166 amino acid sequence of FIG. 5, the –172 to 115 amino acid sequence of FIG. 6, the 1 to 116 amino acid sequence of FIG. 6, the –172 to –1 amino acid sequence of FIG. 6, and the –145 to –1 amino acid sequence of FIG. 6.

In a preferred form the expression product is formed as an insoluble inclusion body and is purified from cell extracts by centrifugation away from the soluble cell proteins. Preferred purification methods include the addition of proteolysis inhibitors and membrane disrupting agents and density gradient centrifugation. If necessary, the purified inclusion bodies may be solubilised and the proteins released by further treated, such as by selective cleavage and/or by additional purification, so as to remove unnecessary proteinaceous matter.

Furthermore, the present invention will yield an inhibin-like protein expressed by bacteria transformed with the plasmids pBTA28, pBTA29, pBTA292 and pBTA296–pBTA305.

In a further embodiment the invention provides a pharmaceutical composition comprising one or more expressed products of the invention in pharmaceutically acceptable form or synthetic equivalent.

In a further form, the invention embraces synthetic peptides which are part of inhibin and which may be inhibin agonists, antagonists or capable of eliciting an antigenic response and used to affect FSH levels or reproductive physiology.

Compositions include those suitable for oral administration or in injectable form and preferably include a pharmaceutically acceptable adjuvant. Also included in the pharmaceutical compositions of the present invention are those in sustained release form, particularly suited for implantation and sustained release in an vertibrate. In such a form the composition can be implanted into an vertibrate to affect gonadal function and removed when the desired effect is obtained.

In a further form the invention provides a vaccine comprising one or more of the expressed proteins in pharmaceutically acceptable form.

The invention also includes a method of affecting gonadal function in a vertebrate comprising administering to said vertibrate an effective amount of a pharmaceutical composition of the present invention.

In a further form the invention embraces antibody preparations prepared as a result of immunological challenge to a vertibrate by administration of one or more expression products of the present invention or pharmaceutical compositions of the present invention. Such antibody preparations include polyclonal and monoclonal antibody preparations.

Throughout this specification and claims use of the term "inhibin" is non-species specific and accordingly embraces related species of inhibin such as bovine, human, ovine, porcine, chicken and fish and particularly human and bovine inhibin. Also the term embraces non-glycosylated and glycosylated inhibin species.

The term "vertebrate" embraces species of fish, amphibians, reptiles, birds and maammals including humans.

Subunit structure of inhibin

As indicated throughout the specification, inhibin as secreted into follicular fluid is a 58 kD protein comprising two subunits: a 43 kD and a 15 kD subunit—A and B respectively. The A or 43 kD species is a homologous protein between species with certain differences such that it would be likely to act as an antigen when one inhibin species was administered to another species. In this way it is thought that different species of inhibins could be used to raise anti-inhibin antibodies with uses hereinafter discussed.

By comparison, the B subunit or 15 kD subunit is virtually identical in amino acid sequence between a number of species, such as human and bovine species.

In certain circumstances the whole protein is cleaved to a 31 kD form comprising two subunits of molecular weight 20 kD and 15 kD—$A_C$ and B respectively. The 31 kD form exhibits inhibin activity and forms part of the present invention. Cleavage of the 58 kD form to the 31 kD form liberates a polypeptide fragment referred to as the $A_N$ fragment which itself could play a significant role in regulating gonadal function and thus is also part of the present invention.

BRIEF DESCRIPTION OF THE DRAWINGS

Notwithstanding the above forms which fall within the broad form of the present invention, preferred forms of the invention will be further described with reference to the following experimental methodology and accompanying drawings wherein:

FIGS. 3A and 3B depict the sequences of the 43 kD (A) subunit and 15 kD (B) subunit probes;

FIGS. 5A, 5B and 5C depict the nucleotide sequence of the bovine inhibin A subunit cDNA as well as its predicted amino acid sequence. Selected restriction enzyme sites are shown above the DNA sequence.

FIGS. 6A, 6B and 6C depict the nucleotide sequence of the bovine inhibin B subunit cDNA as well as its predicted amino acid sequence. Selected restriction enzyme sites are shown above the DNA sequence.

FIGS. 7A and 7B depict the nucleotide sequence of the human inhibin A subunit DNA as well as its predicted amino acid sequence.

FIG. 8 depicts the nucleotide sequence of the human inhibin B subunit DNA as well as its predicted amino acid sequence.

FIG. 10 depicts the strategy for obtaining a full length A subunit cDNA.

FIGS. 11A and 11B describe linkers used to obtain expression of A and B subunit cDNA.

FIG. 12 shows maps of plasmids pBTA302, pBTA303 and pBTA304.

FIGS. 14A and 14B show the strategy for construction of a full length pre pro A subunit cDNA.

FIGS. 15A and 15B show the serum FSH levels of rabbits immunised with a synthetic peptide. Arrows mark the times of vaccination.

Figure 1:
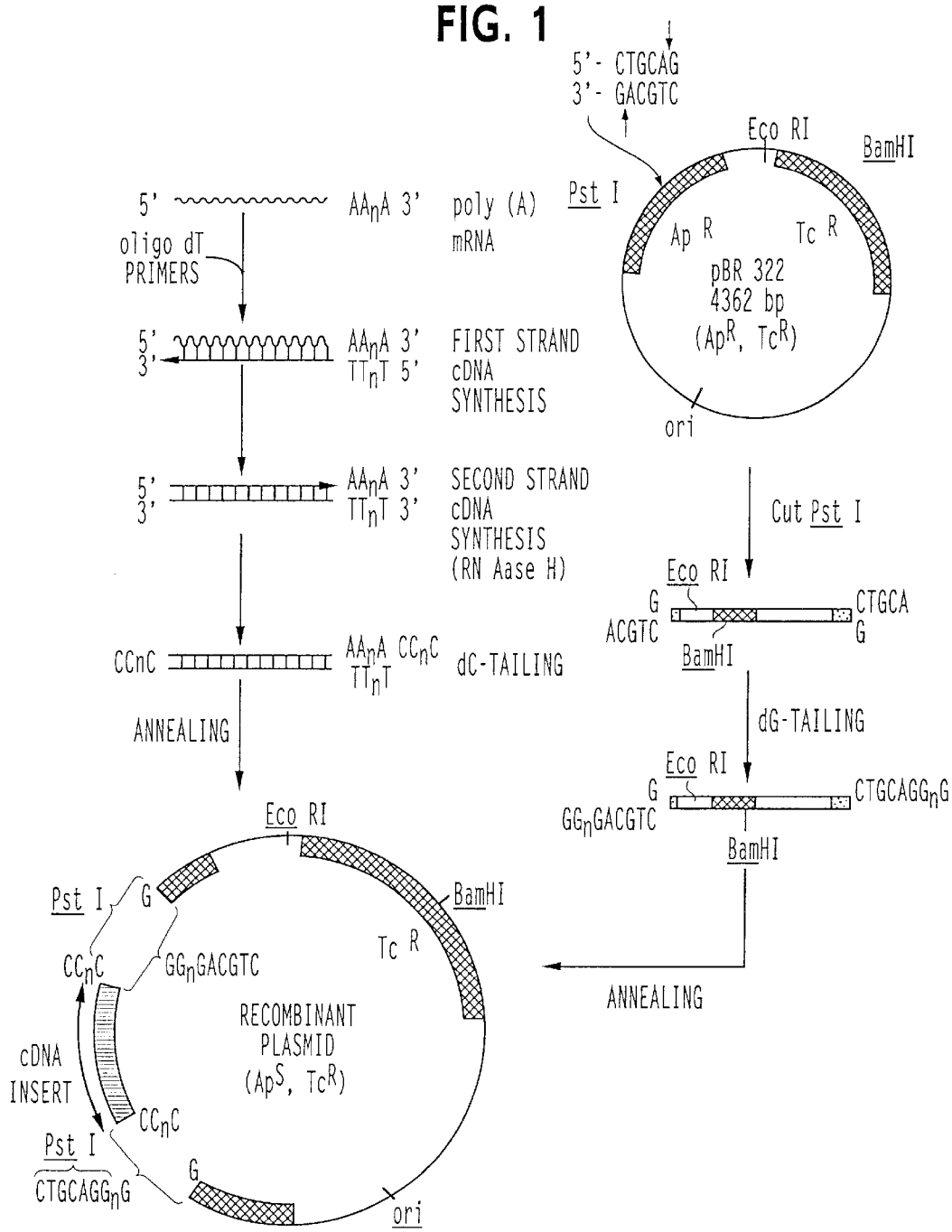
FIG. 1 depicts the strategy for synthesis of recombinant plasmids containing bovine granulosa cell cDNA.

| BEST MODES OF CARRYING OUT THE INVENTION | |
|---|---|
| The following abbreviations are used in the text. | |
| ATP: | adenosinetriphosphate |
| bFF: | bovine follicular fluid |
| bp: | base pairs |
| cDNA: | complementary DNA |
| CG: | chorionic gonadotrophin |
| Ci: | Curies |
| D: | Daltons |
| dATP: | 2'-deoxyadenosinetriphosphate |
| dCTP: | 2'-deoxycytidinetriphosphate |
| dGTP: | 2'deoxyguanosinetriphosphate |
| DNA: | deoxyribonucleic acid |
| DTT: | dithiothreitol |
| dTTP: | 2'-deoxythymidinetriphosphate |
| EDTA: | ethylenediaminetetraacetic acid |
| ELISA: | enzyme-linked immunosorbent assay |
| FSH: | follitropin or follicle stimulating hormone |
| X G: | times the force due to gravity |
| g: | gram |
| HPLC: | high performance liquid chromatography |
| k: | (prefix) kilo |
| l: | liter |
| M: | molar concentration |
| m: | (prefix) milli |
| mol: | moles |
| mRNA: | messenger RNA |
| p: | (prefix) pico |
| n: | (prefix) nano |
| PAGE: | polyacrylamide gel electrophoresis |
| PCMB: | parachloromercuribenzoic acid |
| PMS: | human post-menopausal serum |
| PMSF: | phenylmethylsulfonylfluoride |
| PMSG: | pregnant mares' serum gonadotrophin |
| RIA: | radioimmunoassay |
| RNA: | ribonucleic acid |
| RP-HPLC: | reversed phase HPLC |
| SDS: | sodium dodecylsulphate |
| SS: | steer serum |
| Tris: | tris(hydroxymethyl)aminomethane |
| μ: | (prefix) micro |

In addition, the following terms are defined and used interchangeably in the text irrespective of origin or glycosylation status:

A subunit=43 kD subunit=large subunit of 58 kD inhibin=amino acids His 1 to Ile 330 (FIG. 5)=amino acids His 1 to Ile 306 (FIG. 7).

$A_C$ subunit=20 kD subunit=large subunit of 31 kD inhibin=amino acids Ser 167 to Ile 300 (FIG. 5)=amino acids Ser 172 to Ile 306 (FIG. 7).

$A_N$ fragment=NH$_2$-terminal portion of A subunit=amino acids His 1 to Arg 166 (FIG. 5)=amino acids His 1 to Arg 171 (FIG. 7).

B subunit=15 kD=small subunit of 58 kD and 31 kD inhibin=amino acids Gly 1 to Ser 116 (FIGS. 6 and 8)

By the use of the phrase "having similar immunological activity" it is meant to include a protein which is sufficiently homologous to inhibin or parts thereof so that (1) the immune system of the recipient reacts in the same way as to the native protein or (2) administration will generate antibodies to the protein which are capable of recognising endogenous inhibin.

Also, it should be understood that the term "parts of inhibin" includes sub-units of inhibin.

The methods and products of this work are described in detail below and it is to be understood that there are alternative methods available to a skilled person in the art which fall within the broad form of the present invention.

EXAMPLE 1

Isolation of Messenger RNA (mRNA) from Bovine Granulosa Cells

Whole testes and ovaries or isolated Sertoli and granules cells may be used as a source of inhibin mRNA. In this instance, isolated granulosa cells were used.

a. Collection of granulosa cells.

Bovine follicular fluid (bFF) containing granulosa cells was collected from large follicles on the surface of fresh bovine ovaries at a local slaughterhouse, by use of a needle and syringe. The fluid was stored ice cold from immediately after collection until arrival at the laboratory. The cells from 70–100 ml bFF were centrifuged at 500× G for 5 minutes and the supernatant removed for purification of native inhibin. RNA was extracted from the cells as described below.

b. Extraction and purification of RNA.

Immediately after harvesting, the granulosa cells were lysed by adding 24 ml 4.2 M guanidinium isothiocyanate/20 mM mercaptoethanol/5% (v/v) sacrosyl/10 mM Tris-HCl pH 7.4 (Chirgwin, J. M. et al. (1979) Biochemistry 18; 5294–5299). The lysate was homogenised in a Sorvall Omnimix at speed 4 for 30 seconds then centrifuged at 20,000× G for 15 minutes to remove cell debris. To the supernatant was added 1 g CsCl per 2.5 ml. This mixture was overlaid on a 9 ml 5.7 M CsCl/10 mM EDTA/50 mM Tris-HCl pH 7.8 cushion and centrifuged at 122,000× G for 65 hours at 15° C.

The RNA pellet was washed several times in 5 ml 70% ethanol/30% TE (1 mM EDTA/10 mM Tris-HCl pH 7.5) to remove CsCl. It was finally precipitated from 3 ml TE by the addition of 0.3 ml 3 M Na acetate pH 7.5 and 6 ml ethanol followed by freezing to −70° C. and centrifugation at 20,000× G for 10 minutes. The RNA pellet was redissolved in 1 ml TE and kept at −70° C. until required.

c. Isolation of mRNA.

mRNA was extracted from the total RNA by chromatography on oligo dT cellulose (Aviv. H. and Leder, P. (1972) Proc. Natl. Acad. Sci. USA, 69; 1408–1412). The RNA solution was made 1 M in NaCl/1 mM in EDTA/20 mM in Tris-HCl pH 7.5, heated to 70° C. for 2 min. snap chilled in ice-water and applied to a column (0.5 g dry bed weight) of oligo dT Cellulose (BRL). The flow through fractions were heated, chilled and reapplied twice. The column was washed with 5 ml of the loading buffer then with 5 ml of the same buffer but containing 0.5 M NaCl. The mRNA was eluted at 60° C. in TE. Fractions (0.25 ml) were collected and their mRNA content precipitated using sodium acetate and ethanol (see above) and the pellets dried in vacuo. The mRNA was redissolved in 0.1 ml TE and aliquots (25 $\mu$l) frozen at −70° C.

The integrity of the RNA fractions from these extraction and purification steps was examined by electrophoresis of 1–2 $\mu$g samples on agarose-urea gels (Locker, J. (1979) Anal. Biochem. 98, 353–367). Specifically, the RNA sample in 10 $\mu$l TE containing 5 M urea and 0.01% (w/v) each of the tracking dyes bromophenol blue and xylene cyanol FF were heated to 70° C. for 2 minutes then subjected to electrophoresis in a gel of 1.5% agarose containing 5.6 M urea/14 mM iodoacetate/1 mM EDTA/36 mM $NaH_2PO_4$/40 mM Tris-NaOH pH 7.4. The electrophoresis was terminated when the bromophenol blue dye reached the bottom of the gel and the RNA was visualised under ultratraviolet light after staining with a solution of ethidium bromide.

The concentration of RNA was measured by its absorbtion at 260 nm, an $A_{260}$ reading of 1.0 using a 1 cm light path being taken as 40 $\mu$g RNA per ml. Typically, 60–100 ml bFF would give 1–3 g wet weight pelleted granulosa cells from which 600–900 $\mu$g total RNA and 20–60 $\mu$g mRNA could be extracted.

This mRNA fraction contains mRNA specific for inhibin, its subunits or inhibin-like polypeptides but it is to be understood that the mRNA fraction is a mixture of a large number of different mRNA species in different abundances within the mixture most of which are unrequired.

During the next steps of cDNA synthesis and tailing, each behaves similarly to the mRNA species specific for inhibin, its subunits or inhibin-like polypeptides and their presence will result ultimately in the generation of a large number of unrequired clones and necessitate a screening procedure to identify correct clones, i.e., clones containing cDNA sequences coding for part of, or subunits of, or all of inhibin.

The strategy for preparation of cDNA from mRNA and its incorporation into the vector pBR322 is shown in FIG. 1 and is described in greater detail in Examples 2 and 3 but by example only.

EXAMPLE 2

Synthesis of Copy DNA (cDNA) from mRNA a. Synthesis of the first cDNA strand.

A reaction mix limited in dATP was set up and a small portion of it removed in order to monitor the extent of cDNA synthesis by incorporation of $\alpha$-$^{32}$P dATP. Excess dATP was then added back to the main reaction mix to allow complete first strand synthesis. Specifically, a sample (2 $\mu$g) of the mRNA preparation was made up to 27 $\mu$l volume in water and heated at 70° C. for 2 minutes then snap chilled in ice water. The reaction was started by addition of 23.5 $\mu$l mixture containing 500 ng oligo $dT_{10-17}$ primers (Boehringer), 50 nmols each of dCTP, dTTP and dGTP, 5 nmols of dATP, 100 nmols DTT, 20 units AMV reverse transcriptase (Life Sciences) 2 $\mu$mols of KCl, 400 nmols $MgCl_2$ and 2.5 $\mu$mols Tris-HCl pH 8.5.

Immediately after mixing the analytical reaction was set up by taking a 2 $\mu$l sample into a separate tube containing 0.5 $\mu$l of $\alpha$-$^{32}$P dATP (1800 Ci/nmol; 5 $\mu$Ci/$\mu$l) and 0.5 $\mu$l 60 mM dATP was added back to the main reaction which was placed at 42° C. for 60 min. From the analytical reaction, 0.5 $\mu$l was removed and snap frozen in an ethanol dry ice bath to serve as a zero time control. The remainder of the reaction was placed at 42° C. for 60 min afterwhich a further 0.5 $\mu$l was taken for analysis.

Figure 2:
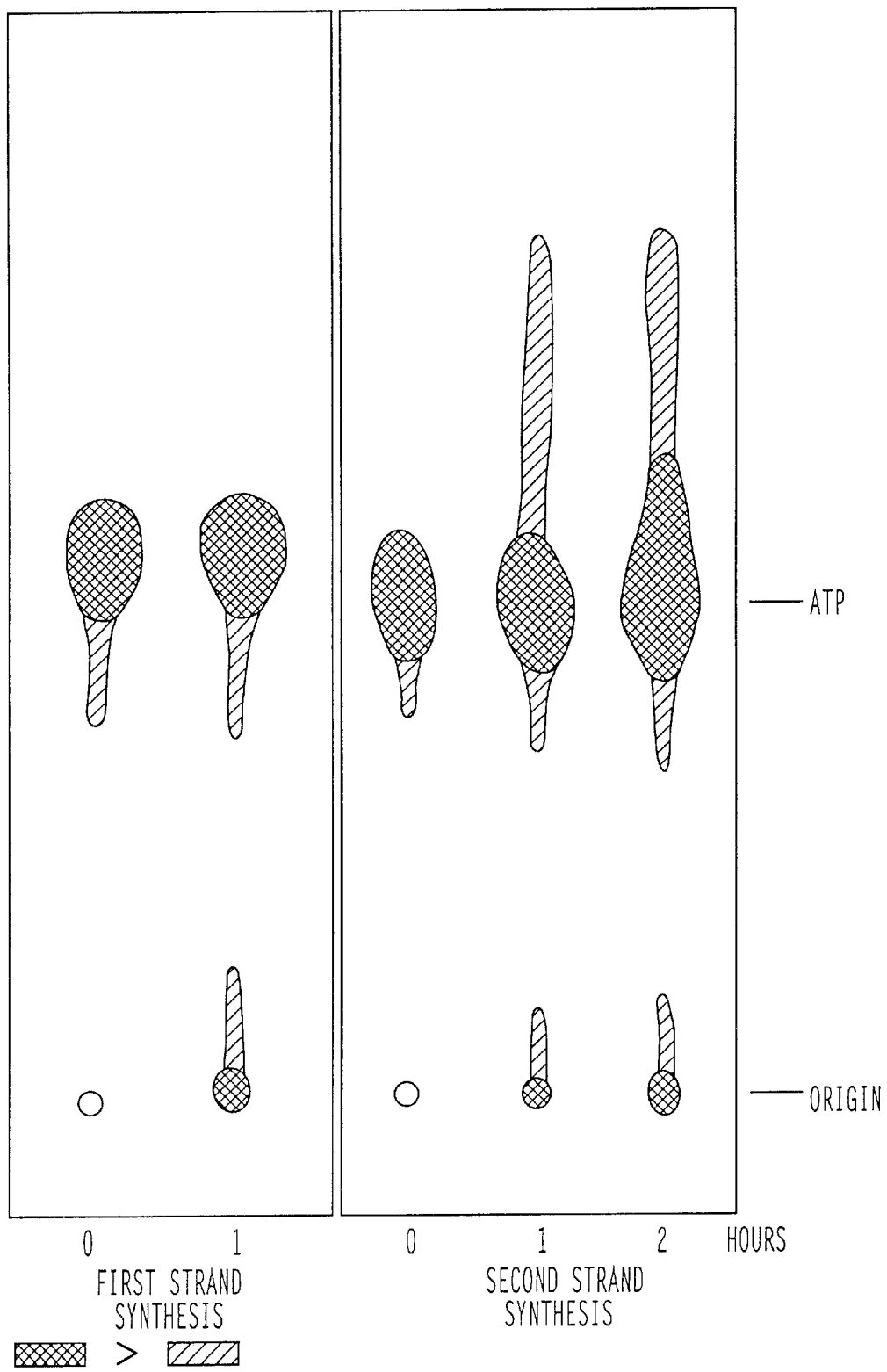
FIG. 2 is a thin layer chromatograph on polyethyleneimine cellulose of the products of cDNA synthesis from messenger RNA of bovine granulosa cells.

Each of the radioactive samples was subjected to thin layer chromatography on polyethyleneimine (PEI) cellulose (Merck) in 0.75 M $KH_2PO_4$ buffer pH 3.5. The results after autoradiography are shown in FIG. 2. By this means the unincorporated nucleotides are removed from the newly synthesised first strands (DNA-RNA hybrids) which remain at the origin. The individual spots were cut out following autoradiography and the incorporated radioactivity determined to give an estimate of the efficiency of incorporation. Incorporation of 10% (estimated maximum incorporation 33%) of the total counts or greater was taken as satisfactory to proceed with the second strand of cDNA synthesis. The remainder of the radioactive material was precipitated twice from 2M ammonium acetate/67% ethanol and subjected to electrophoresis on agarose-urea gels after boiling for 2 minutes in the loading buffer (see above) to separate the RNA and DNA strands. The gel was then subjected to autoradiography on Fuji RX X-ray film. This procedure gives an estimate of the size of cDNA products and typically yielded a range from more than 1000 bases to less than 200 bases.

First strand synthesis may be obtained via other procedures known to those skilled in the art. In this example, oligo dT was used as a primer to give first strand cDNA synthesis from all mRNA species having poly(A) regions. Random primers may also be used to oligo cDNA synthesis from mRNA species. Alternatively, primers having a sequence complementary to some part of inhibin mRNA may be used to obtain specific synthesis of inhibin cDNA. Oligo dT or other primers having a sequence complementary to some part of inhibin mRNA may be used as primers for first strand synthesis.

b. Synthesis of the second strand.

In a strategy similar to that of first strand cDNA synthesis, bulk and analytical reactions were derived from an initial reaction mix that was deficient in dATP.

Specifically, the cDNA-RNA hybrid molecules of the first strand main reaction were precipitated by adding 50 μl 3 M ammonium acetate pH 7.5, and 200 μl ethanol followed by chilling at −70° C. and centrifugation for 5 minutes at 15,000× G. The pellet was resuspended in 50 μl TE, reprecipitated then dried and finally taken up in 50 μl TE.

To this was added 350 μl solution containing 16 nmols each of dCTP, dTTP and dGTP, 1 nmol dATP, 3.5 units RNAase H (BRL) 92 units DNA polymerase I (Boehringer), 40 μg BSA, 6 nmols β-NAD, 400 nmols $(NH_4)_2SO_4$, 4 μmols KCl, 200 nmols $MgCl_2$ and 800 nmols Tris-HCl pH 7.5 (Gubler, U. and Hoffman, B. J. (1983) Gene 25; 263–269.)

Immediately after mixing, the analytical reaction was set up by taking a 2 μl sample into a separate tube containing 0.5 μl α-$^{32}$P dATP (1800 Ci/nmol; 5 μCi/μl) and 2 μl 10 mM dATP added back to the main reaction which was placed at 15° C. for 60 minutes then 22° C. for 60 minutes. From the analytical reactions, 0.5 μl samples were taken and snap frozen in an ethanol-dry ice bath at zero time, 1 hour and 2 hour and analysed by thin layer chromatography as described for the first strand synthesis (FIG. 2). An incorporation of at least 5% (estimated maximum 8%) of the total counts was taken as evidence of good second strand synthesis.

Second strand synthesis may be obtained via other procedures known to those skilled in the art. Examples are given below.

In this case, an RNAase specific for RNA in DNA/RNA hybrids (e.g. RNAase H) together with a DNA polymerase was used. Alternatively, the RNA in the DNA/RNA hybrids resulting from first strand synthesis may be destroyed chemically or enzymatically or removed from the DNA and the DNA allowed to self prime. Second strand synthesis is then carried out by use of a DNA polymerase or a reverse transcriptase and the hairpin loop remaining is digested by means of a single strand specific release such as S1 nuclease.

A third method involves the removal or degradation of the mRNA followed by addition of oligonucleotide (e.g. oligo dC) tails to the 3'-end of the first strand DNA products. A complementary oligonucleotide (e.g. oligo dG) is annealed to the tail and serves as a primer for the second strand reaction by a DNA polymerase or reverse transcriptase. Single- or double-stranded DNA with sequences complementary or identical or similar to inhibin cDNA can also be made by chemical synthesis for cloning.

EXAMPLE 3

Construction of Bovine Granulosa Cell cDNA Libraries in *E. coli* a. Tailing and Annealing cDNA.

The double stranded cDNA from the second strand synthesis was precipitated by the addition of 40 μl 3 M Na acetate pH 7.5 and 800 μl ethanol, followed by chilling to −70° C. and centrifugation at 20,000× G for 5 minutes. The pellet was redissolved in 50 μl TE, extracted twice with an equal volume of phenol (pre-equilibrated with TE), extracted three times with 100 μl diethyl ether (pre-equilibrated with TE) then precipitated by the addition of 50 μl 4 M ammonium and 200 μl ethanol followed by chilling to −70° C. In contrast to previous precipitations, the cold mixture was allowed to come back up to room temperature before centrifugation at 15,000× G for 5 minutes. This procedure helps to remove unincorporated nucleotides. The pellet was dissolved in 50 μl TE and reprecipitated using ammonium acetate and ethanol. The pellet was dried in vacuo and resuspended in 30 μl TE.

To 15 μl cDNA was added an equal volume of buffer containing 30 nmols $CoCl_2$, 3 nmols DTT, 1.5 μmols potassium cacodylate pH 7.2, 5 μg bovine serum albumin, 30 nmols dCTP and 17 units of terminal transferase (BRL). The mixture was incubated at 37° C. for 3–5 minutes, before freezing in an ethanol-dry ice bath then heating to 65° C. for 5 minutes. The tailed DNA was stored at −20° C. until required for use. The cDNA species were incorporated by the process known as annealing into commercially obtained pBR322 plasmid molecules (FIG. 1; Table 2) that contained approximately 24 dG residues on the 3' overhanging ends of the Pst I restriction endonuclease site (BRL Cat. No. 5355 SA). In the annealing process, the dC tails of the cDNA form stable hybrids with the dG tails of the plasmid. Because the Pst I site lies within the pBR322 B-lactamase gene, the resultant plasmids are sensitive to ampicillin but still resistant to tetracycline.

For annealing, 2.5 μl dC-tailed cDNA and approximately 0.5 μg dG-tailed pBR322 were heated at 65° C. for 5 minutes in 50 μl TE containing 0.1 M NaCl then incubated at 57° C. for 2 hours. The solution was then cooled gradually to room temperature over a period of 1 hour and kept on ice or frozen at −20° C. until further use.

The insertion of cDNA species into vector molecules may be obtained by other procedures known to those skilled in the art. For example, any nucleotides may be added to the 3' ends of DNA molecules by use of the terminal transferase reaction known as tailing. These molecules can then be annealed with vector DNA molecules tailed with complementary sequences. Alternatively the cDNA molecules can have synthetic linkers added by DNA ligases which when cut by restriction enzymes, provide convenient sequences for cloning. Alternatively the cDNA may be cleaved directly by restriction enzymes or dNAases for direct cloning. Blunt ended DNA molecules may also be cloned directly into vectors, such vectors include plasmids, cosmids, bacteriophages and other viruses.

b. Transformation of *E. coli* ED8654 with Recombinant Plasmids.

*E.coli* ED8654 (Table 2) was made competent by the procedure of D. Hanahan (1983; J.Mol. Biol. 160, 557–580) and 0.2 ml competent cells were transformed with 10 μl of the annealed cDNA-pBR322 hybrids. After transformation, the cells were grown for 2 hours in 2 ml SOC (5 g/l yeast extract/20 g/l tryptone/10 mM NaCl/2.5 mM KCl/20 mM $MgCl_2$/20 mM $MgSO_4$/20 mM glucose) then centrifuged at 2,000× G for 5 minutes, resuspended in 0.5 ml 0.85% NaCl and the whole suspension plated on a 280 mm LB (5 g yeast extract/10 g tryptone/5 g NaCl per liter) agar (15 g agar per liter) plate containing 10 μg/ml tetracycline-HCl in order to select cells transformed with pBR322 or recombinant plasmids. The incubation was at 37° C. for 48 hours. By this means a typical transformation would yield approximately $5 \times 10^3$ to $5 \times 10^4$ colonies per μg recombinant pBR322 or approximately $10^4$–$10^5$ colonies per μg cDNA. Typically, more than 78% of the transformants contained recombinant plasmids as determined by random screening of plasmid from 14 tetracycline-resistant colonies.

c. Storage of transformed cells.

The colonies from each plate were scraped off in 10 ml LB. The cells resulting from an estimated 2,000 independent transformation events were pooled, centrifuged at 1,500× G for 5 min and resuspended in 5 ml LB (v/v) to which 0.5 ml DMSO was added. Portions (0.4 ml) were frozen in liquid nitrogen and kept at −70° C. until required. Five such pools, were constructed by this means.

Because each original transformant contains a recombinant DNA species which is derived from a complete or partial copy of one of the mRNA species present in the mRNA fraction, collections or pools of such transformants are called libraries. In this instance, libraries of bovine granulosa cell cDNA have been constructed in *E. coli*. An eukaryotic cell may make some $1 \times 10^4$–$2 \times 10^4$ different proteins so a collection of $10^4$ independent transformants should contain members derived from all the more abundant mRNA species. Obviously the vast majority of the cells in these libraries contain cDNA that is not of immediate interest but a few contain complete or partial copies of an inhibin mRNA species and the following procedures are designed to identify and isolate those colonies.

EXAMPLE 4

Screening the Libraries for Inhibin Clones a. Preparation of libraries for screening.

A tube of frozen cells was thawed and diluted $5 \times 10^5$-fold then 0.5 ml spread on the surface of a 280 nm LB agar plate containing 10 μg/ml tetracycline-HCl and incubated at 37° C. overnight. This gave approximately $10^4$ colonies per plate so each transformant in the original library should be represented 1–5 times. Duplicate replicas were taken on nitrocellulose (Schleicher and Schuell) filters and orientation marks made by stabbing through the filters into the agar with a needle dipped in indian ink. The master plates were stored at 4° C. until required and the replica filters incubated face up on fresh LB agar plates containing 10 μg/ml tetracycline-HCl for 8 hours. They were then transferred to LB agar plates containing 50 μg/ml chloramphenicol and incubated overnight to increase the copy number per cell of the recombinant plasmids (Clewell, D. B. (1972) J. Bacteriol. 110; 667–676; Hanahan, D. and Meselson, M. (1980), Gene 10, 63–67). The filters were treated by a modification of the methods of Grunstein, M. and Hogness, D. S. (1975; Proc. Natl. Acad. Sci. USA 72, 3961–3965). The filters were laid face up on a sheet of Whatman 3MM paper saturated in 0.5 M NaOH/1.5 M NaCl for 15 minutes to promote lysis of the cells and formation of single stranded DNA, then neutralized for 15 minutes on 2 changes of paper saturated in 1.5 M NaCl/0.5 M Tris-HCl pH 7.5. They were air dried, laid on a Buchner funnel then saturated with 20 ml $CHCl_3$ before aspiration. The filters were then baked for 2 hours at 80° C. in a vacuum oven.

b. Strategy.

In order to identify those clones containing an inhibin cDNA gene or part thereof, radioactively labelled oligodeoxyribonucleotide (oligonucleotide) probes were employed. They were designed to be complementary to part of the mRNA coding for the $NH_2$-terminal amino acid sequences of each of the 43 kD and 15 kD subunits (Probes 1 and 5, FIG. 3). The $NH_2$-terminal sequences of the 43 kD and 15 kD subunits were derived from amino acid sequencing of intact 58 kD inhibin and its separated subunits and the first 16 amino acids of each were given in International Patent Application PCT/AU85/00119. Subsequently, by subtracting the amino acid sequence of the 43 kD subunit (as determined by cDNA sequencing in pBTA22 and pBTA23, see Example 6A) from that of intact 58 kD inhibin, it was possible to refine and extend the original analysis of the 15 kD subunit as shown in Table 1. This refinement indicated another area useful for making oligonucleotide probes, that of amino acids 20 to 24 inclusive. FIG. 3 shows the oligonucleotide probe made (Probe 2). It is a 24-fold degenerate 14mer and was used to isolate pBTA293 and pBTA294. Because each amino acid (with the exception of methionine and tryptophane) has more than one DNA codon that specifies it, it is desirable to incorporate all possible combinations of codons in the probes. Thus there are 64 possible DNA sequences that code for most of the amino acid sequence chosen for the large subunit of inhibin (Probe 1, FIG. 3) and 24 possible DNA sequences that code for most of the amino acid sequence chosen for small subunit of inhibin (Probe 2, FIG. 3). In order to maximise the possibility of obtaining representative molecules of each of these sequences. Probe 1 was pooled from four independent syntheses having, at positions 2 and 6 from the 5'-end, either dG and dA or dT and dA or dG and dG or dT and dG. Probe 2 was synthesised in a single batch.

c. Oligonucleotide synthesis and purification.

The oligonucleotide probes were synthesized with the aid of an automatic DNA synthesiser (Applied Biosystems Inc., Model 380A). The machine was programmed to sequentially couple N,N'-diisopropyl phosphoramidite deoxyribonucleotide derivates to a derivatised controlled pore glass support according to the methodology originally developed by Matteucci, M. D. and Caruthers, M. H. (1981), J. Amer. Chem. Soc. 103, 3185–3191).

The protocol recommended by Applied Biosystems Inc. was used. Degenerate oligonucleotides were generated by substituting a mixture of phosphoramidite deoxyribonucleotides for a single derivatised base. The oligonucleotides were purified away from prematurely terminated oligonucleotides by preparative electrophoresis in a gel (20 cm×20 cm×1.5 cm) containing 20% (w/v) acrylamide/1.0% (w/v) N,N'-bis acrylamide/1 mM EDTA/50 mM Tris adjusted to pH 8.3 with solid boric acid. Electrophoresis was at 500 V for 1.5 hours then the oligonucleotides were visualised by placing the gel on a Kieselgel™ F254 (Merck) thin layer chromatography plate for examination under UV light. The oligonucleotides appear as dark bands. They were excised and eluted from the gel overnight in 0.8 ml sterile water. The concentration of eluted oligonucleotides was estimated by determining the absorbance at 260 nm, an $A_{260}$ reading of 1.0 using a 1 cm light path being taken as 35 μg single stranded DNA per ml.

d. 5' end labelling reaction.

The purified oligonucleotides were made radioactive by adding a $^{32}P$-labelled phosphate group to their 5' ends.

Specifically, 40 pmols oligonucleotide and 40 pmol γ-$^{32}P$ ATP (2000 Ci/mmol; 5 μCi/μl) were lyophilised then dissolved and incubated at 37° C. for 90 minutes in 20 μl buffer containing 4 units T₄ polynucleotide kinase/10 mM MgCl₂/10 mM DTT/1 mM spermidine/50 mM Tris-HCl pH 7.5.

The radioactive oligonucleotides were purified as described above and visualisation was by autoradiography for 5 minutes on Fuji RX™ X-ray film. Elution was in 0.8 ml sterile water overnight. Each of the 4 oligonucleotide pools that together constitute Probe 1 (see Example 1b) was treated separately up to this stage then combined.

TABLE 1

NH₂-TERMINAL SEQUENCE ANALYSIS AND PROBE DESIGN

| Residue | 1 | 2 | 3 | 4 | 5 | 6 | 7 | 8 | 9 | 10 | 11 | 12 | 13 |
|---|---|---|---|---|---|---|---|---|---|---|---|---|---|
| Inhibin | | Ala | Glu | Gly | Gly | Phe | Met | Val | Arg | Gly | Ser | Glu | Pro |
| | | Leu | Val | | Asp | Gly | Lys | | Asn | Ile | | | Lys |
| A Subunit | Asn | Ala | Val | <u>Gly</u> | <u>Gly</u> | <u>Phe</u> | <u>Met</u> | <u>Arg</u> | Arg | Gly | Ser | Glu | Pro |
| B Subunit | Tyr | Leu | Glu | | <u>Asp</u> | <u>Gly</u> | <u>Lys</u> | <u>Val</u> | <u>Asp</u> | <u>Ile</u> | | | Lys* |

| Residue | 14 | 15 | 16 | 17 | 18 | 19 | 20 | 21 | 22 | 23 | 24 | 25 | 26 |
|---|---|---|---|---|---|---|---|---|---|---|---|---|---|
| Inhibin | Glu | ASp | Gln | Asp | Val | Ser | Gln | Ala | Ile | Leu | Phe | Pro | Ala |
| | Lys | Gln | Phe | Phe | | | Phe | Lys | Asp | Ile | Gly | | Asn |
| A Subunit | Glu | Asp | Gln | (Asp)Val | | (Ser) | (Gln) | (Ala) | Ile | Leu | (Phe) | (Pro) | (Ala) |
| B Subunit | Lys* | Gln* | Phe* | Phe* | | | <u>Phe*</u> | <u>Lys*</u> | <u>Asp*</u> | <u>Ile*</u> | <u>Gly*</u> | | Asn* |

58 kD inhibin was reduced, alkylated and the separated subunits isolated by electro-elution from SDS-PAGE gels. 58 kD inhibin (80 pmol). A subunit (17 pmol) and B subunit (6 pmol) were subjected to Edman degradation in a gas phase sequenator.
(Xaa)=Amino acids determined from cDNA sequence.
Xaa*=Amino acids identified by subtraction of the A subunit sequence from the double sequence of 58 kD inhibin.
Regions used to design oligionucleotide probes are underlined.

e. Use of the probes for screening the libraries.

Each set of radioactive probes was taken up in 40 ml 5× SSC/10× Denhardt's solution (20× SSC in 3 M NaCl/0.3 M trisodium citrate pH 7.0 and 50× Denhardt's solution is 1% (w/v) Ficoll/1% (w/v) polyvinylpyrrolidone/1% (w/v) bovine serum albumin) and one filter representative of each of the libraries was immersed in the solutions with gentle agitation overnight.

The filters were washed in several changes of 1× SSC/0.1% SDS (sodium dodecyl sulphate) at room temperature and subjected to autoradiography for 3–5 hours at −70° C. using Fuji RX™ X-ray film and a Dupont Cronex™ Hi Plus intensifying screen. The film was developed and the filters washed again in 1× SSC/0.1% SDS at 37° C. then subjected to autoradiography overnight.

Any areas which were more intense than the background after the wash at room temperature or which were still visible after the wash at 37° C., and which corresponds to the position of colonies on the master plates were deemed to be potential inhibin clones.

The foregoing examples describe some means and a strategy by which cells containing inhibin or inhibin-like DNA sequences may be obtained but are not meant to exclude alternative means or strategies. For example, it is possible, to use genomic DNA as the starting DNA and so preclude the need for cDNA synthesis (see Example 8). Also, the cloning vector may be one in which expression of cloned DNA fragments is obtained and the screening procedure is based on the use of anti-inhibin antiserum (see Example 10) or the direct detection of inhibin or inhibin-like biological activity. Such methods are well known to those experienced in the art.

EXAMPLE 5

Characterisation of Putative Clones a. Purification of potential inhibin clones.

The areas corresponding to the dark spots on the autoradiograms were picked and streaked for single colonies on LB plates containing 10 μg/ml tetracycline-HCl and incubated for 16 hours at 37° C. Replicas of these plates were stored at 4° C. until required. The filters were placed for 3–6 hours on LB agar with tetracycline-HCl then transferred to LB agar containing 50 μg/ml chloramphenicol for 16 hours, then the colonies were lysed as described previously and screened again using the radioactive oligonucleotide probes. Single colonies corresponding to the darkest spots on autoradiograms from these filters were picked, restreaked and analysed.

b. Restriction mapping of plasmid DNA.

The plasmid DNA content of at least one isolate of every putative inhibin clone was analysed by extraction and digestion with the restriction endonuclease Pst I. This enzyme releases the cDNA insert from the plasmid and also cleaves the cDNA at any internal Pst I sites. Plasmid DNA extraction was based on the method of Birnboim and Doly (1979; Nucl. Acids Res. 7: 1513–1523). An overnight culture of cells grown in 3 ml LB was centrifuged and resuspended in 0.2 ml lysis buffer (50 mM glucose/10 mM EDTA/0.2% lysozyme/25 mM Tris-HCl pH 8.0) and incubated at 0° C. for 10 minutes. To this, 0.4 ml alkaline SDS (0.2 M NaOH/1% (w/v) SDS) was added and after 10 minutes at 0° C., 0.3 ml 3 M Na acetate pH 4.8. After 15–30 minutes at 0° C. the resulting white precipitate was removed by centrifugation. The plasmid content of 0.8 ml of the supernatant was precipitated by adding 0.7 ml isopropanol, chilling to −70° C. and centrifuging at 15,000× g for 5 minutes. The pellet was redissolved in 0.4 ml TE and precipitated by adding 40 μl 3M Na acetate pH 7.5 and 0.8 ml ethanol, chilling and centrifuging as above. The final pellet was dried in vacuo and dissolved in 0.2 ml TE. A sample (20 μl) was digested with 20 units Pst I (Boehringer) in a final volume of 40 μl TA buffer (66 mM potassium acetate/10 mM magnesium acetate/0.5 mM DTT/0.1 mg/ml BSA/33 mM Tris-acetate pH 7.9) containing 10 μg/ml RNAse A at 37° C. for 60 minutes then subjected to electrophoresis on polyacrylamide gels (up to 10% acrylamide/0.27% bis acrylamide) in TBE buffer (2.5 mM EDTA/133 mM Tris/89 mM boric acid. Samples of pBR322 digested with Alu I (Boehringer) were used as size standards. The clones identified initially are listed in Table 2.

c. Sequencing strategies.

Appropriate restriction enzyme fragments (created with one or more of the enzymes Pst I, Pvu II, Sau 3AI or Sma I) were purified from polyacrylamide gels by elution in 0.5M ammonium acetate/10 mM magnesium acetate/0.1M EDTA/ 0.1% SDS at 37° C. overnight then precipitated with ethanol, redissolved in TE and subcloned into the replicative forms of bacteriophages M13 mp8 and MB13 mp9 for sequencing by the dideoxy chains termination method of Sanger F. et al. (1977; Proc. Natl. Acad. Sci. USA 74, 5463–5467) using univeral primer (17 mers; #1211 or #1212; New England Biolabs) or oligonucleotide primers complementary to the cDNA itself. The latter are particularly useful for isolating overlapping cDNA species and for extending known sequences from overlapping cDNA species or for sequencing from the dG/dC tails towards the centre of the cDNA.

For all sequencing, subcloning and expression work (see Example 10) restriction enzymes were used in TA (Example 5B) and T4 ligase (Boehringer) was used according to the manufacturers instructions.

(e) BTA647=E. coli K12, hsdR$_k$, supE44, supF58, lac Y1, galT22, galK2, trpR55/F'lacI$^q$, Δ(lacZ)M15, lacY$^+$A$^+$, proA$^+$B$^+$, tra$^+$.

(f) Ruther, U. and Muller-Hill, B. (1983) EMBO J. 2; 1791–1794

(g) BTA634=E. coli K12 Δ(lac,pro), supE(glnV), thi, lon-1, zaj:: Tn5/F' proA$^+$B$^+$, lacI$^q$, Δ(lacZ)M15, lacY$^+$A$^+$, traD36.

(h) pBTA286 is a derivative of pUR291 in which a Hpa I—Ava I DNA fragment of 2355 base pairs has been deleted from the coding sequence of the lacZ gene such that the coding sequence remains in frame.

(i) BTA 652=E.coli K12 Δ(lac, pro), thi$^-$, supE(glnV)44, hsdR$_K$17 endA1, gyrA96, relA1/F' proA$^+$B$^+$, lacI$^q$, Δ(lacZ)M15, lacY$^+$A$^+$ traD36.

(j) Viera, J. and Messing, J. (1982) Gene 19, 259–268.

(k) BTA545=E. coli K12 thi$^-$, Δ(lac, arg F), U169 Δ(lon) 100, hf1150, zje/zjf::Tn10, rpsL, hsdR$_K$/F' lacI$^q$, Δ(lacZ) M15, lacY$^+$A$^+$, proA$^+$B$^+$, tra$^+$.

(l) BTA637=BTA652, lon-1, zaj::Tn5

Plasmids BTA413, BTA416, BTA417, BTA418 have been deposited with the Australian Government Analytical

TABLE 2

PLASMIDS AND BACTERIAL STRAINS

| CODE[a] | BACTERIAL STRAIN | PLASMID CONTENT | PARENT PLASMID | SUBUNIT; FRAGMENTS; | RESTRICTION SIZE[b] |
|---|---|---|---|---|---|
| BTA123 | ED8654[c] | — | — | — | |
| | ED8654 | pBR322[d] | — | — | |
| BTA404 | ED8654 | pBTA22 | pBR322 | A; Pst I; 215/175 | |
| BTA405 | ED8654 | pBTA23 | pBR322 | A; Pst I; 480/295/150 | |
| | BTA647[e] | pUR292[f] | — | — | |
| BTA410 | BTA647 | pBTA28 | pUR292 | A; pBTA23 Pst I; 480 | |
| BTA411 | BTA647 | pBTA29 | pUC9 | A; pBTA23 Pst I; 480 | |
| BTA412 | ED8654 | pBTA30 | pBR322 | A; Pst I; 300/240/480/410 | |
| BTA413 | ED8654 | pBTA290 | PBR322 | A; Pst I; 480/360 | |
| BTA415 | BTA647 | pBTA292 | pUR291 | A; pBTA30 Pst I; 410 | |
| BTA416 | ED8654 | pBTA293 | pBR322 | B; 135/510 | |
| BTA417 | ED8654 | pBTA294 | pBR322 | B; 165/320/530 | |
| BTA418 | ED8654 | pBTA295 | pBR322 | A; 300/500 | |
| BTA419 | BTA634[g] | pBTA296 | pUR290 | A; Sau 3A I-Sau 3A I | |
| BTA420 (BTA420 = ATCC67054) | BTA634 | pBTA297 | pBTA286[h] | A; pBTA296; EcoRI-EcoRI | |
| BTA421 | BTA634 | pBTA298 | pUR290 | A$_c$; Hae II-Sau 3A I plus adapter | |
| BTA422 (BTA422 = ATCC67059) | BTA634 | pBTA299 | pBTA286 | A$_c$; pBTA298 EcoRI-EcoRI | |
| BTA423 | BTA634 | pBTA300 | pUR291 | B; pBTA293 Pst I; 510 | |
| BTA424 (BTA424 = ATCC67058) | BTA634 | pBTA301 | pBTA286 | B; pBTA300 EcoRI-EcoRI | |
| BTA425 | BTA634 | pBTA286 | pUR291 | — | |
| BTA426 (BTA426 = ATCC67057) | BTA652[i] | pBTA302 | pUC7[j] | A; pBTA296 Sau 3A I-Sau 3A I | |
| BTA427 (BTA427 = ATCC67056) | BTA545[k] | pBTA303 | pUC13 | A$_C$; Hae II-Sau 3A I plus adapter | |
| BTA1360 (BTA1360 = ATCC67055) | BTA637[l] | pBTA304 | pUC8 | B; pBTA293 Pst I; 510 | |
| BTA1361 | BTA634 | pBTA305 | pBTA297 | A; full length pre proA | |

(a) Code number for Biotechnology Australia Pty. Ltd. Culture Collection.

(b) Sizes (where given) are bp estimated from electrophoresis on polyacrylamide gels against standards of pBR322 digested with Alu I. These values differ slightly from actual sizes derived by DNA sequencing.

(c) Murray, N. K. et al., (1977), Mol. Gen. Genet. 150; 53–61.

(d) Bolivar, F. et al., (1977) Gene 2; 95–113.

Laboratories (AGAL, 1, Suakin Street, Pymble, NSW 2073, Australia) and been given accession numbers NM00/13784, NM00/13785, NM00/13786, NM00/13787, respectively. Plasmids BAT 420, BTA 1360, BTA 427, BTA 426, BTA 424 and BTA 422 have been deposited with the American Type Culture Collection (ATCC 10801 University Boulevard, Manassas, Va.) and been given accession numbers ATC 67054, ATC 67055, ATCC 67056, ATCC 67057, ATCC 67058, and ATCC 67059, respectively.

Figure 4:
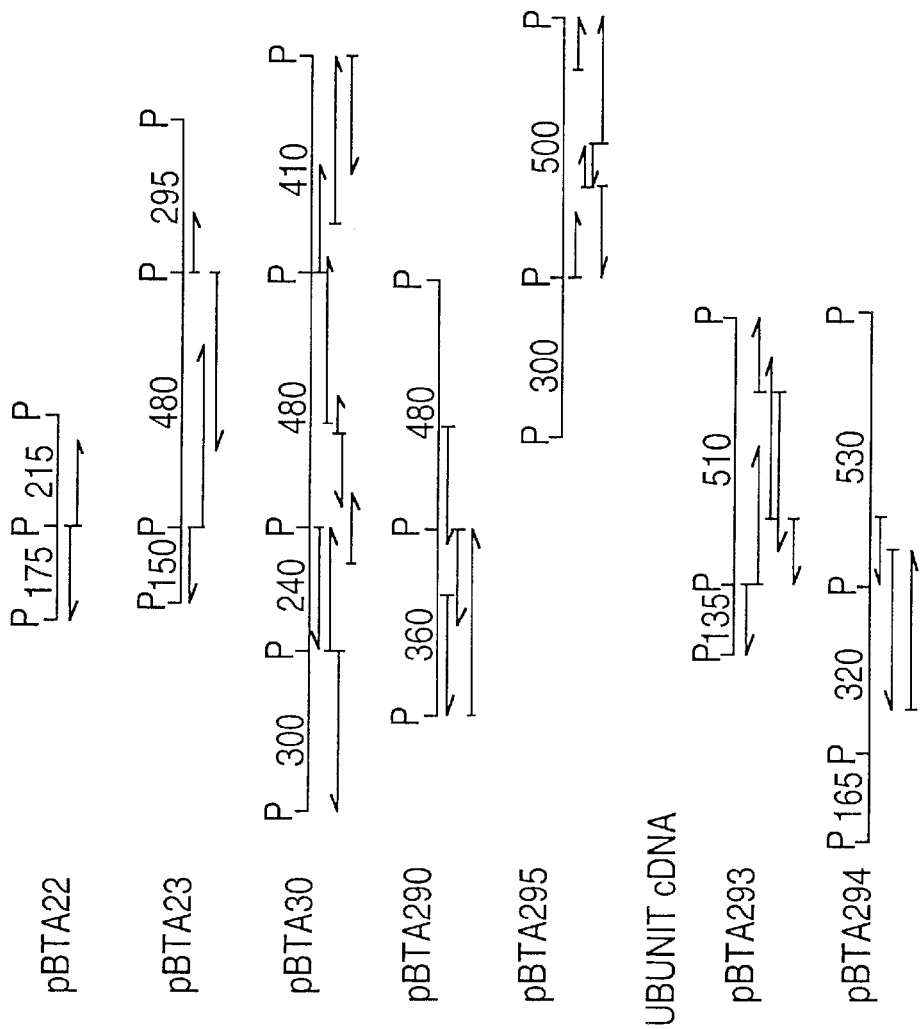
FIG. 4 depicts a restriction enzyme (Pst I) map and sequencing strategy of seven inhibin cDNAs.

The Pst I map and the strategy for sequencing the cDNA inserts from the plasmids is given in FIG. 4 and a composite nucleotide sequence encoding the A subunit is shown in FIG. 5. This sequence is entirely contained within the cDNA from plasmids pBTA290 and pBTA295. The 410 bp fragment of PBTA30 contains the stop codon and the next 6 base of the 3'-untranslated region before the dG/dC tails. The CAG encoding His 1 of the A subunit is present in the 5'-PsI I cDNA fragments of pBTA22, pBTA23 and pBTA290 but not in either the 240 or 300 base pair Pst I cDNA fragments of pBTA30. These two fragments contain no open reading frames or sequences in common with the other clones and may therefore represent part of an unspliced intron.

The cDNA sequence contains an open reading frame from base 1 to 1140. In this reading frame, the first ATG is at base 61 (Met −60) and the amino acid sequence following Met −60 is indicative of a signal peptide but, in contrast to most signal peptides, there is no arginine or lysine before the string of hydrophobic leucines (Watson, M. E. E. (1984) Nucl. Ac. Res. 12, 5145–5164). This signal peptide is expected to finish between Gly −44 and Gly −41 leaving a pro-peptide of some 40 amino acids preceding His −1. Thus the A subunit of inhibin is initially synthesized as a pre-proprotein of 38,810 Daltons extending from Met −60 to Ile 300.

The A subunit is derived from its precursor by cleavage at paired arginine residues (−2, −1), a common signal for proteolytic processing of precursor proteins (Steiner, D. F. et al. (1980) Ann. N.Y. Acad. Sci. 343, 1–16). The A subunit proprotein contains three other pairs of arginine residues at positions −6, −5, 8, 9 and 165, 166. Cleavage of the A subunit at residues 165, 166 would generate two fragments of similar size here designated $A_N$ and $A_C$. The $A_C$ fragment constitutes the 20-kDa subunit of 31-kDa bovine inhibin (see Example 9). The A subunit is predicted to contain 11 cysteine residues, 4 of which are in the $A_N$ fragment from His 1 to Arg 166. These 4 residues are expected to be internally bonded allowing removal of the $A_N$ fragment from the $A_C$ subunit. The $A_C$ subunit contains 7 cysteines and at least one of these is expected to form a disulphide link to the B subunit. The A subunit has two potential N-glycosylation sites at Asn 80 and Asn 202 based on the recognition sequence Asn-X-Ser/Thr (Wagh, P. V. and Bahl, O. P. (1981) CRC Crit. Rev. Biochem. 10, 307–377) and Asn 202 is contained in the $A_C$ subunit. The predicted molecular weights of the protein chains of subunits A and $A_C$ are 32,298 and 14.624 which are approximately 25% less than those estimated by SDS-page for natural inhibin (43-kD and 20-kD respectively). This may be use in part to the carbohydrate content of the native molecules which may alter both their molecular weights and molar volumes. From these differences, both the $A_N$ and $A_C$ portions are expected to be glycosylated, probably at Asn 80 and Asn 202 but whether O-linked glycosylation of serine and threonine residues is involved is not known. The carbohydrate content of the glycoprotein hormones bovine LH, human CG and PMSG has been estimated at 16%, 29–31% and 45% by weight (Pierce J. G. and Parsons, T. F., (1981) Ann. Rev. Biochem. 50: 465–495) so our figure of approximately 25% based on apparent molecular weight may represent the lower end of this range.

The cDNA sequence predicts a 3'-untranslated region in the mRNA of 42 bases. This includes a typical polyadenylation signal (AATAAA) 16 bases before the poly(A) tail (Nevins, J. R. (1983) Ann. Rev. Biochem 52, 441–466). The 3'-untranslated region is A+T rich (40.4% G+C) in contrast to the coding sequence (66.3% G+C) and the 5'-untranslated region (71.6% G+C).

b. B (15 kD) SUBUNIT CLONES

Five independent clones were detected with Probe 2 and the cDNA encoding the mature B subunit from two representatives is shown in FIG. 4. The other three clones contained cDNA with a restriction pattern similar to pBTA293 but with shorter 5'-Pst I fragments.

The nucleotide sequence of B subunit cDNA was derived from sequencing pBTA293 and pBTA294 (FIG. 6). The B subunit is synthesized at least as a proprotein and, like the $A_C$ subunit, it is the C-terminus of is respective proprotein. It is separated from the pro-section by 5 consecutive arginine residues. It contains two pairs of lysine resides at positions 13, 14 and 102, 103 but it is unlikely that these are processing sites (Steiner, D. F. et al. (1980) vide supra). There are nine crysteine residues and the odd number suggests that at least one is available for crosslinking to the $A_C$ subunit. From the cDNA sequence it is predicted that the protein chain of the B subunit has a molecular mass of 12,977 daltons which is close to the apparent molecular weight of 14,900 estimated from SDS-PAGE of the native B subunit. There are no apparent N-glycosylation sequences in the mature B subunit but Asn −145 in the preprotein may be glycosylated.

The 3'-untranslated region of the B subunit is 94 nucleotides long and there is no AATAAA polyadenylation signal as in the cDNA coding for the A subunit. The last 12 bases of the 3'-untranslated region before the poly(A) tails match closely the last 12 bases of erythropoietin 3'-untranslated cDNA (ACTGAAACCACC) which also has no AATAAA sequence (Jacobs, K. et al. (1985) Nature 313, 806–810). The G+C content of the B subunit coding region (bases 157 to 504) is 54.2% and that of the 3'-untranslated region is similar (55.3%) in contrast to the differences observed for the A subunit coding sequence and 3'-untranslated region.

EXAMPLE 7

Identification of Bovine Inhibin-Like Sequences in Genomic DNA

Sequences similar or homologous to the genes coding for the large (43 kD) and small (15 kD) subunits of bovine inhibin were identified in human, ovine, porcine, fish and chicken genomic DNA.

This was achieved essentially by standard Southern Blot hybridisation techniques (Maniatis T. et al. (1982), "Molecular Cloning", Cold Spring Harbour). Essentially, genomic DNA is digested with a restriction enzyme and the resulting fragments separated according to size by electrophoresis on agarose gels. The DNA is transferred to a nitrocellulose (or other) membrane which is then probed with [$^{32}$P]-labelled cDNA coding for substantial parts of the 43 kD or 15 kD bovine inhibin subunits. This results in the detection of genomic DNA fragments which are similar or identical in nucleotide sequence.

Specifically, genomic DNA was prepared either from a human macrophage cell line U937 (ATCC CRL 1539) or from human blood, pig blood and chicken blood or from bovine and ovine soft tissues. From the soft tissues and the human cell line the method used was essentially as described in Maniatis T. et al., vide supra. From blood, DNA was prepared as follows: 15–15 ml of blood (+0.625% citrate) was diluted to 40 ml with cold 10 mM EDTA/10 mM Tris-HCl, pH 7.5, (TE 10—10) and placed on ice for 5 min to lyse the blood cells. After centrifuging for 5 min at 4000 x g the pellet was resuspended in 10 ml cold TE 10—10, diluted to 40 mls with TE 10—10 and centrifuged 5 min at 3000 x g The pellet was disaggregated in 10 mM Tris pH 7.5, 5 mM EDTA (the same volume as the starting blood volume). 10% SDS was added to 0.5%, proteinase K added to 50 μg/ml and the mixture incubated at 37° overnight with gentle shaking. 10 ml of phenol saturated with 0.1 mM Tris-HCl pH 8.0 and containing 0.1% 8-hydroxyquinoline was added and mixed gently for 5–10 min at room temperature. 10 ml of $CHCl_3$: isoamyl alcohol (24:1) was added and mixed for 5–10 min, followed by centrifugation at 8000 x g, for 10 minutes at room temperature. The aqueous phase was re-extracted twice more with 15 ml $CHCl_3$: isoamyl alcohol. 1/20 the volume of 5M NaCl and 2 volumes of ethanol were added at room temperature and mixed. The DNA was removed with a Pasteur pipette, air dried 30–60 seconds and dissolved in 4 ml of TE by gentle agitation at 37° for 3 hours. The DNA was re-precipitated as above and redissolved in 3 ml TE.

Samples (generally 10 μg) of this DNA were cut with various restriction endonucleases according to the manufacturer's instructions at a concentration of 40–50 μg/ml using up to 500 units/ml of enzyme and incubating for 16 hours. The products were deproteinised by extraction with an equal volume of phenol followed by three extractions with chloroform and precipitation in 0.2M NaCl with 2.5 volumes of ethanol. The pelleted DNA was dissolved in water and size fractionated by electrophoresis (75 volts/4 hours) on all 11x14 cm 1% agarose gel in TAE buffer. DNA was denatured by immersing the gel in a solution of 1.5M NaCl/0.5M NaOH for 45 minutes followed by neutralisation for 2x45 minutes in 3.0M NaCl/0.5M Tris-HCl pH 7. The DNA was transferred by capillary action to a nitrocellulose membrane (Schleicher and Schuell) and fixed by baking under vacuum at 80° for two hours. The filters were prehybridised with a solution containing 50% formamide, 5 x SSPE (Maniatis et al, vide supra), 5 x Denhardts and 25 μg/ml sonicated herring sperm DNA for 2–4 hours.

The hybridising probes were as follows:
a) the 790 bp Sph I—Sma I fragment from the A subunit cDNA gene of pBTA23 (FIG. 5).
b) a 1109 bp Sph I—Eco RI fragment obtained from the bovine B subunit clone pBTA293 (FIG. 4). This contains the B subunit cDNA from base position 361 to 718 (FIG. 6) as well as a 751 bp fragment from the Pst I to Eco RI sites of pBR322.

These fragments were isolated from low gelling temperature agarose gels after electrophoresis and labelled with α-$^{32}$P dATP by the method of Feinberg, A. P. and Vogelstein, B. (1984) Anal. Biochem. 137, 266–267.

Approximately 30 ng of DNA was labelled to a specific activity of $2 \times 10^8$ to $10^9$ counts per minute (CPM)/μg of DNA and between 3 and $4 \times 10^6$ CPM of probe mixed, after heating to 100° C., with a solution containing 1 x Denhardts/ 50% formamide/5 x SSPE/1X Denhardts/10% dextran sulphate/25 μg/ml sonicated herring sperm DNA. Hybridisation of the filters was for 20 hours at 42°. The filter was rinsed at room temperature in 2 x SSC, 0.1% SDS then washed at 50° for 30 minutes each in 2 x SSC/0.1% SDS then 1 x SSC/0.1% SDS then 0.2 x SSC/0.1% SDS. The conditions of hybridisation were such that hybridising sequences must be at least 70–75% homologous overall to the bovine cDNA sequences. After exposure to Fuji RX X-ray film for at least 24 hours the sizes of hybridising fragments could be determined against marker DNA fragments of known sizes.

The approximate size (in base pairs) of the fragments of human, bovine, ovine, procine and chicken genomic DNAs which hybridised strongly to the A or B bovine subunit gene probes are as follows:

TABLE 3

| GENOME | ENZYME | FRAGMENTS | ENZYME | FRAGMENTS | ENZYME | FRAGMENTS |
|---|---|---|---|---|---|---|
| A SUBUNIT PROBE ||||||||
| Bovine | Pst I | 3400, 2700, 960, 480 | Pvu II | 1700 | Bam HI | 13000 |
| Human | " | 2450, 1200, 480 | " | 700 | " | 18000 |
| Ovine | " | 2650, 980, 480 | " | ND | " | 11000 |
| Porcine | " | 2200, 2000, 480 | " | ND | " | 2150 |
| Chicken | " | (some hybridisation) | " | ND | " | 6600 |
| Bovine | Eco RI | 5–6000 | Hind III | 5000 | | |
| Human | " | 15000 | " | 20000 | | |
| B SUBUNIT PROBE ||||||||
| Bovine | Eco RI | 7000 | Hind III | 3300 | Pst I | ND |
| Human | " | 9000 | " | 11000 | " | 650 |
| Ovine | " | 7000 | " | 3900 | " | 680 |
| Porcine | " | 7000 | " | 6000 | " | 1100, 680 |
| Chicken | " | 14000 | " | 4350 | " | 1310 |
| Fish (*Melanotaenia splendida*) | | ND | | ND | " | 3600 |

(ND = not determined)

The DNA from each species tested possesses a limited number (generally one, and exceptionally up to three on digestion with Pst I) of fragments hybridising to the large or small bovine inhibin subunit cDNA probes. Characteristic was an approximately 480 bp Pst I fragment common to all species probed with the large subunit cDNA. These hybridising fragments demonstrate the presence in species other than cattle of genes similar to or homologous with bovine inhibin genes. It is not excluded that inhibin cDNA sequences not included in the present choice of probes may hybridise to genomic DNA other than that in the fragments shown in Table 3.

In a separate series of experiments, A and B subunit precursor mRNA species in RNA from rat ovaries were detected using the bovine subunit cDNA as probes. These mRNA species were found to be more abundant in the ovaries of rats that had been treated with PMSG, thus demonstrating the usefulness of inhibin DNA as a diagnostic probe.

The cDNA genes coding for bovine A and B inhibin subunits, therefore, can be used to identify DNA and RNA coding for inhibin molecules in the genomes and organs of other species. Because of this, the inhibin molecules they encode are homologues of bovine inhibin and may be used in a similar manner.

EXAMPLE 8

Isolation of Human Inhibin-Like Sequences from Genomic DNA

Human DNA sequences similar to and homologous with cDNA coding for the A and B subunits of bovine inhibin have been isolated. This has been achieved by constructing human genomic libraries of DNA cloned into bacteriophage λ and probing the bacteriophage plaques with [$^{32}$P]-labelled DNA fragments prepared from the cDNA coding for either the A or B subunits of bovine inhibin. The phase DNA of positive plaques was isolated, cut with restriction endonucleases and fragments containing the inhibin-like DNA (as determined by Southern blot hybridisation using the probes and techniques in Example 7) were subcloned into M13 for nucleotide sequence determination.

More specifically a human genomic library was constructed in bacteriophage λ EMBL3 based on a method described by Maniatis et al. vide supra, or a similar human genomic library in λ L.47 (Loenen, W. A. M. and Brammar, W. J. 1980, Gene 20, 249–259). Human genomic DNA (prepared as described in Example 7) was partially digested with Sau 3A Ito give DNA ranging in size from approximately 5–30 kbp in length. This was size fractionated by sucrose gradient centrifugation (McCarty, K. S. et al., (1974) Anal. Biochem. 61, 165–183) using gradients in which Cmix=15%, Cr=31.5, Vm=34.45 and aK=2.174 in TE plus 1M NaCl and centrifuging 12.5 μg of DNA for 2 hrs at 50,000 RPM in the Beckman SW50.1 rotor.

DNA of approximately 15–25 kbp was collected from this gradient, ethanol precipitated with 5 μg tRNA as carried and ligated to EMBL3 λarms. EMBL3 DNA (Promega Biotec, Madison Wis. USA) was digested with endonucleases BamH I and EcoR I, deproteinised with phenol and chloroform and precipitated with 0.6 volumes isopropanol in the presence of 0.3M sodium acetate at 0–4° C. 2.4 μg was mixed with approximately 1 μg of 15–25 kbp human DNA in 10 mM Tris HCl pH 7.5, 10 mM MgCl$_2$, 1 mM ATP, 20 mM dithiothreitol, 2 units of T$_4$ DNA ligase (Boehringer Mannheim) in a total volume of 40 μl and incubated for 20 hours at 15°. 95 μl of Packagene (Promega Biotec) was added and incubated for 2 hours at 22° C. The mixture was plated out with the restrictive host NM539 (see Promega Biotech instructions) to an approximate density of 50,000 plaques per 14 cm diameter plate. The above reaction mixture yielded 8 such plates.

The human library in bacteriophage L47 was also plated out with NM539 to a similar plaque density.

For probing with inhibin cDNA probes, the plaques were transferred to nitrocellulose filters, two replicas per plate, as described (Maniatis et al. (1982) vide supra). The labelled probes were as follows: for sequences corresponding to the A subunit of bovine inhibin the 790 bp Sph I-Sma I fragment was used for the λ L47 library, the Bam HI-Hind III fragment from pBTA297 containing A subunit cDNA (see Table 2) was used for the EMBL3 library. For the small subunit the probe was the Sph I-Eco RI fragment described in Example 7. The preparation, labelling and hybridisation conditions are as described in Example 7 for Southern blot hybridisation. For the first plaque screen, both probes were included in the one hybridisation solution.

Potential positive plaques were eluted, re-plated and probed until pure clones were obtained. Of particular interest were two clones, λ A2 hybridising to the large (A) subunit obtained from the L47 library and λ B1 hybridising to the small (B) subunit obtained from the EMBL3 library. The λ A2 carried an insert of human DNA of approximately 11–12 kbp. Digestion with Pst I gave a number of fragments, notable of which were three which hybridised to the [$^{32}$P]-labelled Sph I-Sma I fragment of the bovine A gene (described above). Pvu II digestion gave rise to two fragments hybridising to the same probe (Table 4).

TABLE 4

| ENZYME | DNA SIZE (bp) | DEGREE OF HYBRIDISATION |
|---|---|---|
| Pst I | 2500 | + |
| " | 1160 | ++ |
| " | 480 | ++++ |
| Pvu II | 800 | +++ |
| " | 420 | ++ |

The 1160 and 480 bp fragments (Pst I digestion) and the 800 bp fragment (Pvu II digestion) are similar in size to Pst I and Pvu II fragments hybridising to the same probe in the Southern blot analysis of human genomic DNA shown in Example 7.

Hybridisation of the same λ A2 Southern blots with a [$^{32}$P]-labelled 500 bp Pst I fragment from pBTA295 identified only the 1160 bp fragment of Pst I digestion of λ A2. Such a pattern of hybridisation is consistent with the hypothesis that the cloned human DNA fragment carries a sequence similar or homologous to bovine inhibin DNA. Digestion of λ A2 with Pst I followed by excision of the 480, 1160 and 2500 bp fragments from a low gelling temperature agarose gel, subcloning into M13 and determination of the nucleotide sequence (see Example 5c) resulted in the sequence shown in FIG. 7. The DNA sequence of an intron of 1.4–1.5 kbp between bases 275 and 276 has been omitted. The similarity between the derived amino acid sequence and that of the bovine inhibin pre pro A subunit shows that it is an homologous protein, and represents the precursor of the human inhibin A and A$_C$ subunits. The A$_N$ fragment of human inhibin is defined as amino acids His 1 to Arg 171 and the A$_C$ subunit as amino acids Ser 172 to Ile 306.

The λ B1 clone carried a DNA insert of approximately 21–26 kbp. The DNA was also cut with restriction endonuclease Pst I size fractionated by electrophoresis on a 1% agarose gel and transferred to a nitrocellulose filter. On hybridising with the 136 bp or the 510 bp inhibin Pst I fragments ([$^{32}$P]-labelled) purified from pBAT293 (FIG. 4), the smaller probe bound to a fragment of DNA of approximately 1300 bp (range 1100–1350 bp) in length whilst the larger probe bound to a fragment approximately 800 bp in length (range 740–840 bp). The nucleotide sequence of part of the 800 bp fragment was determined by digesting λ B1 with Pst I, purifying Pst I fragments of approximately 800 bp on low gelling temperature agarose gels and cloning into the Pst I site of M13 mp9 followed by nucleotide sequence determination. Subcloning of smaller fragments of the 800 bp fragment (Pst I-Sau 3A I; Sau 3A I-Sau 3A I) into M13 for sequencing resulted in the nucleotide sequence shown in FIG. 8. The amino acid sequence determined from translation of the DNA sequence shows that the DNA codes for the whole of the B chain of inhibin and that the human B chain from Gly 1 to Ser 116 is identical to the bovine B chain.

It is understood that the fragments of these λ clones which carry the human inhibin DNA sequence as well as similar synthetic fragments can be inserted into prokaryote or eukaryote expression systems for the production of human inhibin or polypeptides structurally related to inhibin (see Example 10). Moreover, the λ clones themselves may be transfected into a suitable eukaryote cell line for expression.

The detection of inhibin subunit genes in various vertebrate species (Example 7) by using bovine cDNA as a probe, followed by the cloning and sequencing of human inhibin subunit genes to show extensive similarities in amino acid sequence reveals other vertibrate inhibins to be homologous with if not identical to the bovine inhibin protein defined International in Patent Application PCT/AU85/00119 and in FIGS. 5 and 6.

We have detected inhibin activity in follicular fluid or ovarian extracts from many vertibrate species (for example see Table 5) and have purified native inhibin from human FF and ovine FF by the Methods of International Patent Application PCT/AU85/00119 and Example 9 and found both species to be functionally similar to bovine inhibin and to have 58 kD and 31 kD forms with subunit structures similar to the bovine forms.

Also, rabbit, bovine and human inhibins are neutralized by the rabbit antiserum described in International Patent Application PCT/AU85/00119 which was raised against purified 58 kD bovine inhibin, and also cross-react in an RIA again indicating close structural homology (Table 5).

Nevertheless, the fact that native bovine inhibin is capable of raising an immune response in the rabbit indicates that there are differences between rabbit and bovine inhibins that are recognised by the rabbit immune system as foreign and in this way, inhibin from one species may be used as an antigen in another to generate antibodies capable of recognising endogenous inhibin.

The antibodies produced by the rabbit do not cross react significantly with ovine or rat inhibins indicating specificity of the antiserum for particular epitopes even though all species shown in Table 5 are active in the rat pituitary cell culture which demonstrates a conformational homology for interaction with the pituitary cell receptor.

It is also apparent from the foregoing discussion that, since the B subunit is highly conserved and perhaps identical in most species, use of a mutant B subunit protein as an antigen to raise antibodies that cross-react with the B subunit of endogenous inhibin will have wide applicability to and efficacy in many species. Such an antigen may be produced by techniques such as in vitro mutagenesis of the DNA followed by expression of the new gene as described in Example 10, or by chemical modification of the B subunit protein or by isolation of a B subunit gene from a species having a B subunit similar, but not identical, to that described in FIGS. 6 and 8, followed by expression of that gene as described in Example 10.

TABLE 5

INTERACTION OF INHIBINS FROM FOLLICULAR FLUIDS WITH RABBIT 474

| | ANTI-BOVINE 58 kD INHIBIN ANTISERUM | | |
|---|---|---|---|
| | | % CROSS-REACTIVITY IN RIA* | |
| SPECIES | NEUTRALISATION | 58 kD TRACER | 31 kD TRACER |
| Bovine | + | 100 | 100 |
| Human | + | 27 | 28 |
| Ovine | − | 8.0 | 0.3 |
| Rat | − | 6.0 | ND |
| Rabbit | + | ND | ND |

*See Example 16a.
ND = Not determined

EXAMPLE 9

The Relationship Between 58 kD and 31 kD Forms of Inhibin

Inhibin is made by the granulosa cells and secreted into follicular fluid. There is exists primarily as a 58 kD form as shown earlier (International Patent Application PCT/AU/85/00119).

Evidence of a small form of inhibin was obtained from studies aimed at improving the efficiency of the purification of inhibin from bovine follicular fluid. Using the purification procedure of Robertson, D. M. et al. (1985; Biochem. Biophys. Research Commun. 126, 220–226: International Patent Application No. PCT/AU85/00119), a pH 4.75 precipitation step was introduced between the initial neutral and acid buffer gel filtration chromatography steps. This resulted in the generation of a second biologically active species which was separated from the first using the acid gel filtration step. Following reversed-phase HPLC and preparative polyacrylamide gel electrophoresis of this second species it was found to be a protein of apparent molecular weight 31,000 composed of two subunits of apparent molecular weight 20,000 and 15,000 with a similar biological activity to the original 58 kD material. The apparent molecular weights of the smaller subunits of the two inhibin species are very similar (approximately 15 kD) suggesting that the difference in apparent molecular weights of the two inhibin species is mainly due to changes in the 43 kD subunit which has been shortened to approximately 20 kD.

Figure 9A:
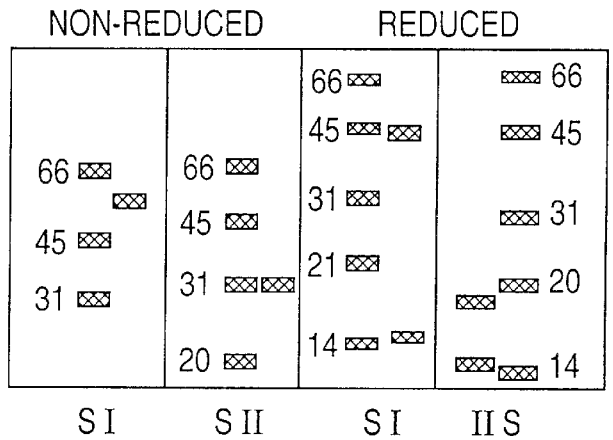
FIGS. 9A and 9B show the structure of 58 kD inhibin (I) and 31 kD inhibin (II) compared to molecular weight standa4rds (S; sizes shown in kD) on SDS-PAGE gels (A) and conversion of 58 kD native bovine inhibin to the 31 kD form after overnight incubation in steer serum (SS) and human post-menopausal serum (PMS) as determined by radioactivity measurements in slices from non-reduced SDS-PAGE gels (B).
Figure 9B:
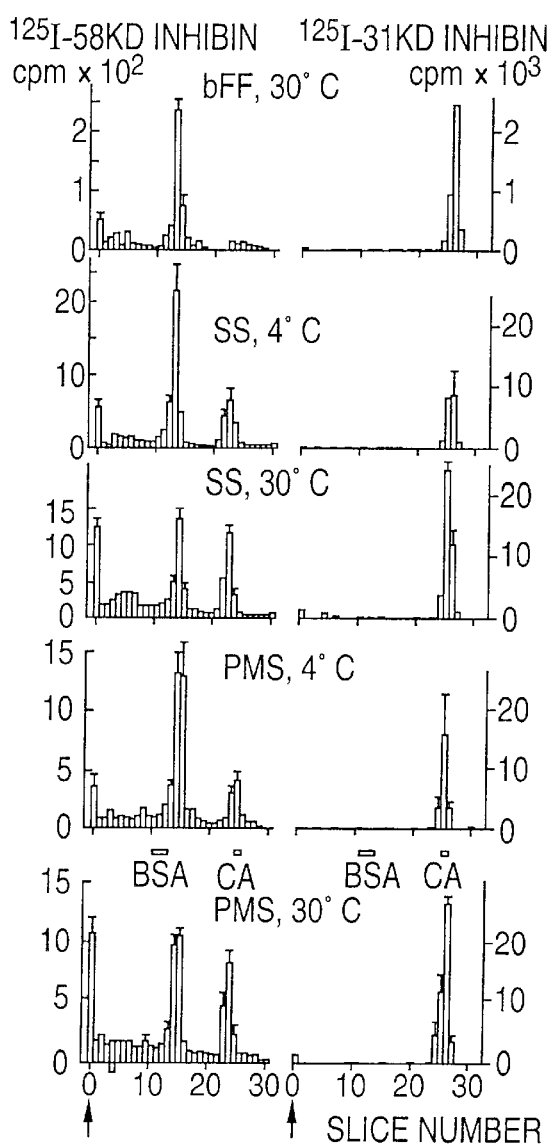

Furthermore, pure 58 kD inhibin is converted to the 31 kD form during incubation with steer serum or (SS) human post-menopausal serum (PMS). This cleavage does not take place during similar incubation with bFF (FIG. 9). Therefore, the smaller (31 kD) form of inhibin and especially its larger (20 kD) subunit may be considered to be direct derivatives of the 58 kD form of inhibin described in International Patent Application PCT/AU85/00119 and in Robertson, D. M. et al. (1985); Biochem. Biophys. Res. Commun. 126, 220–226) and directly derivable from the subunit genes described herein.

Also, it is obvious that serum devoid of natural inhibin (SS and PMS) can be used to process recombinant inhibin or its subunits in vitro, and that the enzyme responsible could be purified from serum or from cell types that carry out this reaction and used to a similar end. This enzyme activity has been characterised with respect to protease inhibitors. Following incubation of serum with iodinated 58 kD inhibin at 30° C. for 17 hrs in the presence of SS or PMS, the conversion of 58 kD to 31 kD inhibin was reduced from 24% to 4.5% by the inclusion of 3 mM parachloromercuribenzoate or 10 mM EDTA. Bacitracin and Pepstatin A (each 0.3 mM) were without effect. This pattern of protease inhibition is characteristic of processing enzymes (Lazure, C. et al. (1983) Can. J. Biochem. Cell Biol. 61, 501–515) and in agreement with these findings, there is a canoic processing site (Arg-Arg) preceeding Ser 167 in the A subunit (FIG. 5) which is utilised in this reaction.

Cleavage of inhibin on release into the serum, results in 2 molecules, the 31 kD form of inhibin and the $A_N$ fragment (amino acids 1–166 of the large subunit). Whilst the 31 kD form is known to suppress the synthesis and release of FSH by pituitary cells, it is also possible that one or both molecules return to the gonads and regulate gonadal function directly, or that inhibin itself, fragments of inhibin or its precursor molecules, such as $A_N$, have biological functions other than the pituitary regulation of FSH. An indication is provided by the fact that immunisation of rabbit 699 with Peptide 1 provided a dramatic fall to zero in FSH titre (see Example 15).

Both subunits of inhibin are formed as prepro molecules and the propeptides from each subunit may have biological activities of their own, again encompassing cell growth and regulation. The 31 kD form of inhibin itself has significant homology to transforming growth factor-β (Derynck, R. et al. (1985) Nature 316, 701–705), again suggesting a role for the native molecule in cell regulation, in addition to its known effects on FSH synthesis by pituitary cells.

EXAMPLE 10

Expression of Inhibin cDNA a. 43 kD and 20 kD subunits.

Although clone BTA405 (Table 2) contains cDNA coding for part of the large subunit of inhibin, it is not expected to make any part of inhibin because the cDNA is dC tailed (see Example 3a) and there is no ribosome binding site or initiating ATG (f-Met) codon in the sequence. In order to obtain expression of part of the inhibin gene a fusion peptide was made by cloning the largest (approx. 480 bp) PstI fragment of the cDNA in pBTA23 into the Pst I site of pUR292. In correct orientation, this generates a protein consisting of most of the E. coli protein β-gelactosidase followed by amino acids 27 to 183 of the 43 kD subunit of inhibin. The plasmid constructions were transformed into E. coli BTA647 (Table 2).

In order to identify such clones an immunological screening method was used. Following transformation, the cells were plated on LB agar containing 50 μg/ml sodium ampicillin for 16 hours at 37° C. in order to select for transformants. The colonies were replicated onto nitrocellulose membranes (Schleicher and Schuell) and orientation marks made by stabbing through the membranes into the agar with a needle dipped in indian ink. The master plates were stored at 4° C. until required and the replica filters incubated face up on fresh LB agar plates containing 50 μg/ml sodium ampicillin for 3 hours. The fusion proteins were included on LB agar containing 0.5 mM isopropyl B-D-thiogalactoside (IPTG) at 37° C. for 2 hours. The filters were laid on a sheet of Whatman 3MM paper saturated with 0.2M NaOH/1% (w/v) SDS for 5 minutes then neutralised on paper saturated with 0.5M Tris-HCl pH 7.5. Proteins released from the colonies bind to the nitrocellulose in situ. Any protein binding sites remaining on the nitrocellulose were blocked by immersion of the filters with gentle agitation in TST (150 mM NaCl/0.05% (v/v) Tween™ 20 (Sigma)/10 mM Tris-HCl pH 8.0) containing additional (0.5% (v/v)) Tween™ 20 for 1 hour. The filters were treated at room temperature overnight with a solution containing rabbit anti-bovine 58 kD inhibin antiserum (International Patent Application PCT/US85/00119) diluted 1:50 in TST then washed several times in TST to remove residual antibodies. The filters were treated for 1 hr at room temperature with a 1:200 dilution in TST of swine anti-rabbit immunoglobulin-horseradish peroxidase conjugate (Dakopatts) then washed in TST. Finally, they were washed in 20 mM Tris HCl pH 7.5 and stained with a solution containing 0.5 mg/ml 4-chloronaphthol/0.03% (v/v) $H_2O_2$/20 mM Tris-HCl pH7.5.

Colonies containing the fusion peptide were identified from areas on the filters that stained more intensely than areas on which the control strain BTA647 (pUR292) had been grown. Some background staining of other colonies was visible despite attempts to reduce the anti-E. coli antibody titre of the rabbit anti-inhibin antiserum by preincubation of the diluted antiserum with filters on which a lawn of induced E.coli BTA647 (pUR292) had been grown and lysed.

Figure 13B:
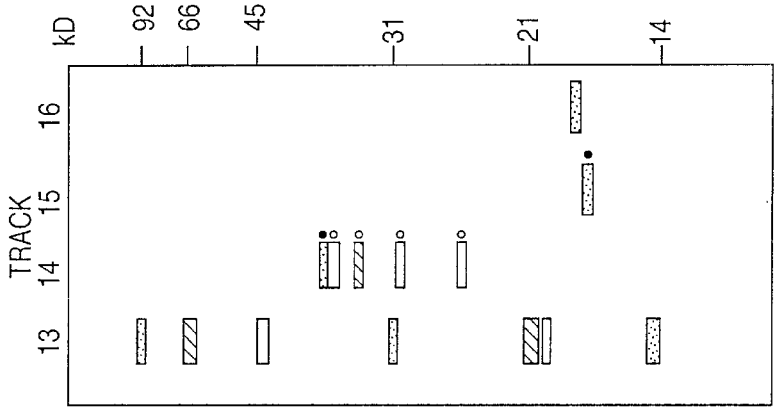
FIGS. 13A and 13B show the expression of inhibin subunit fusion proteins and β-galactosidase in *E. coli* strains.
Figure 13A:
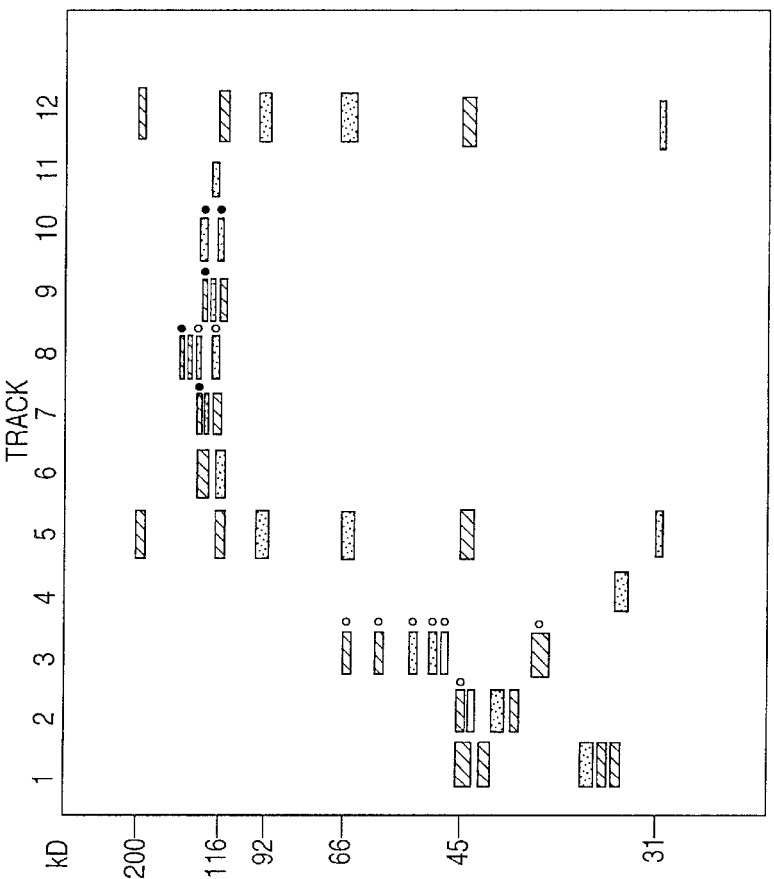
Figure 14B:
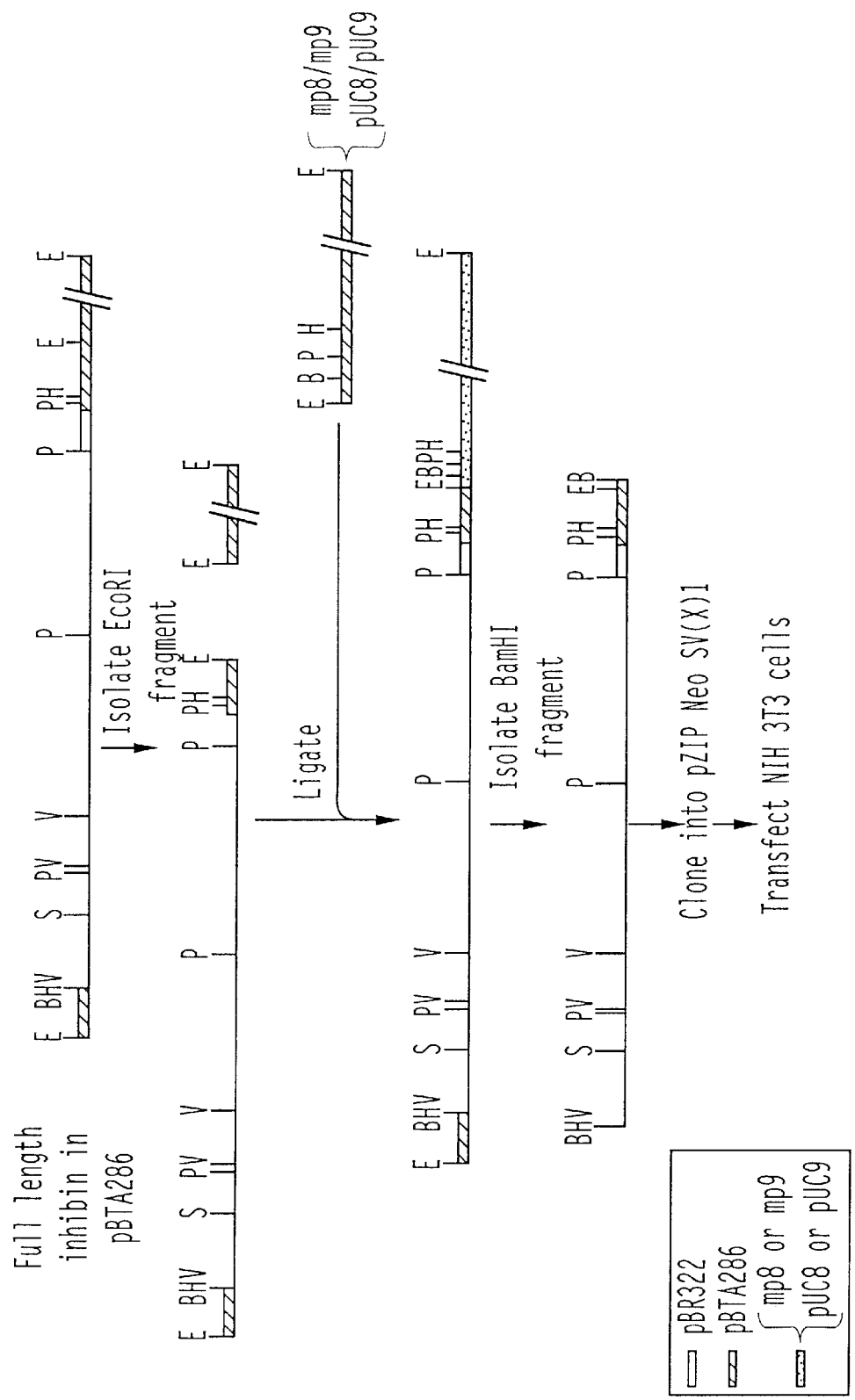

Three such colonies were purified and their plasmid content analysed. All contained pUR292 with the expected cDNA fragment in correct orientation and one of these strains was designated BTA410 and its plasmid pBTA28 (Table 2). The identity of the fusion peptide was checked by the Western blotting procedure (Towbin, H., et al., (1979) Proc. Natl. Acad. Sci. USA, 76, 4350–4354) in which proteins are denatured with sodium dodecyl sulphate and separated according to size by polyacrylamide gel electrophoresis, then transferred laterally onto a sheet of nitrocellulose. The nitrocellulose is then treated as described above in order to determine which protein band contains inhibin antigenic determinants. The protein samples were prepared as follows:

Cultures of BTA647(pUR292) and BTA410 grown overnight at 37° in LB were diluted 1:100 into fresh medium and incubated until a turbidity of $A_{600}$ 0.4 was obtained then were made 0.5 mM in IPTG and incubated for a further 2 hours before harvesting. The cell pellets were resuspended directly in 0.1 volumes loading buffer (electrophoresis buffer containing 30% (w/v) sucrose/1% (w/v) SDS/0.1M B-mercaptoethanol/0.01% bromophenol blue) and heated in a boiling water bath for 5 minutes. Samples (10–30 ul) were applied to polyacrylamide gels (Laemmli, U. K. (1970) Nature, 227, 680–685; Mattick, J. S. et al., (1980) Eur. J. Biochem. 114, 643–651) and the electrophoresis performed until the bromophenol blue dye reached the bottom of the gel. The lateral transfer was done using a Hoeffer Transblot apparatus at 1 amp for 1 hour in 15.6 mM tris base/120 mM glycine. Blocking and treatment of the filters with antisera was as described above. For direct visualisation of proteins in polyacrylamide gels, the gels were soaked in destain solution (10% (v/v) methanol/5% (v/v) glacial acetic acid) for 30 minutes then stained with 0.5% (w/v) Coomassie Brilliant Blue R250 made up in the same solution for 1 hour. The gels were destained by gentle agitation in several changes of destain solution and the protein bands compared to those found by Western blotting and immunodetection. Strain BTA410 was shown to contain at least two proteins which together may represent some 5–10% of the total cell protein which are induced by IPTG and are detected by the anti-inhibin antiserum (FIG. 13, Track 10) and which are not present in strain BTA647 (pUR292) (FIG. 13, Track 11). They are larger (approximately 130 and 117 kD) than native β-galactosidase (116 Kd) and therefore represent β-galactosidase-inhibin fusion proteins. The largest of the fusion proteins is compatible with that estimated from DNA analysis (approximately 132 kD).

Using a similar approach, the 410 bp Pst I fragment of pBTA30 was expressed in pUR291. The resultant plasmid is termed pBTA292 (Table 2) and gain, the fusion protein was detectable using the anti-inhibin antiserum (FIG. 13, Track 9).

In order to obtain expression of the complete subunit, the cDNA from pBTA290 and pBTA30 was spliced and the strategy used is shown in FIG. 10. Briefly it involved purification of Sau 3A I fragments from each of the clones, cleaving them at the unique Rsa I site and religation. The mixture of ligation products was cleaved with Sau 3A I and the products were ligated into pUR290. The clones were then screened with Probes 3 and 4 (FIG. 3) in order to identify clones containing both the 5'-Sau 3A I-Rsa I fragment of pBTA290 and the 3'-Rsa I-Sau 3A I fragment of pBTA30. The production of a β-galactosidase-inhibin fusion protein is ensured when the insert is in the correct orientation because pUR290 gives the correct reading frame from Asp −10 to Ile 300. Correct expression of the 480 and 410 bp Pst I sections can be checked independently by use of the specific antibodies isolated from columns containing the fusion products of pBTA28 and pBTA292 (see Example 9). The resulting plasmid has been termed pBTA296 (Table 2). This complete A subunit gene has also been cloned into the Bam HI site of pUC7 as a Sau 3A I-Sau 3A I fragment and the resulting plasmid (pBTA302; FIG. 12) transferred into BTA652 to generate BTA426 (ATCC67057). The sequence Asp-Pro at the Sau 3A I site can be used to cleave the inhibin portion of a fusion protein from the protein upstream because this sequence is labile in formic acid (Nilsson, B. et al. (1985) Nucl. Ac. Res. 13, 1151–1162).

The expression of a full length 43 kD subunit fused to β-galactosidase (amino acids Asp −10 to Ile 300) from strain BTA419 is shown in FIG. 13, Track 8. In addition to the full length β-galactosidase-inhibin protein there are least 3 other bands of lesser size down to a molecular weight approximately that of native β-galactosidase perhaps representing proteolytic degradation of the full length product or premature termination of transcription or translation. The bulk of the fusion protein is soluble. The inhibin DNA and flanking β-galactosidase DNA was excised from pBTA296 as an Eco RI restriction fragment and inserted into pBTA286 (Table 2; FIG. 13, track 4) to generate pBTA297 (Table 2); clones expressing the inhibin DNA at the C-terminus of the shortened β-galactosidase protein from pBTA286 were selected by colony immunohybridisation as described above. Examination of such clones under phase-contrast microscopy (e.g. BTA420; Table 2) revealed them to produce the fusion protein as an insoluble product termed an inclusion body which confers some protection from proteolytic degradation in the cell and greatly simplifies purification for antigen preparation (Examples 12 and 13). Strain BTA420 has been designated ATCC67054 and the protein from purified inclusion bodies of BTA 420 is shown in FIG. 13, Track 3. The expression of the A subunit in BTA426 is shown in FIG. 13. Track 14 and again this protein is formed predominantly as an inclusion body. In contrast to the fusion protein in BTA420, the longest fusion protein in BTA-426 is also the most abundant and the most reactive in Western blot analysis indicating it to be a superior host-vector combination for production of inhibin-like protein.

From the foregoing it is obvious that other restriction enzyme sites may be useful in the expression of the A subunit. Foremost is the unique Sph I site that spans the codon for His 1 and oligonucleotide linkers can be designed to allow expression of the A subunit or the $A_N$ fragment in a variety of hosts and vectors, either as fusion products, or as a fusion-independent protein where a new f-Met codon is introduced immediately preceeding the CAG encoding His 1 or where a signal peptide is provided prior to His 1. Such constructions are well known to those experienced in the art and an example is given in FIG. 11.

This expression linker is designed to give expression of the 43 kD protein via a new N-terminal methionine after insertion into a trp promoter plasmid such as ptrpL1 (Edman, J. C. et al. (1981) Nature 291, 503–506) by utilising the Cla I site and as a β-galactosidase-inhibin fusion protein after insertion into pUC7, pUC13 or pUR290 using the Bam HI site and as a trp E-inhibin fusion protein after insertion into pWT121 (Tacon, W. et al. (1980) Molec. Gen. Genet. 177, 427–438).

The method used for reconstruction of a full length pre pro A subunit precursor is given in FIG. 12. Basically, it involves isolation of the Pvu II-Pvu II fragment from pBTA295 and addition of the linker (non-phosphatased) shown in FIG. 11 Aii which reconstructs the first 4 amino acids of the signal peptide (Met −60 to Glu −57) 5' to the first Pvu II site and provides a Bam HI site at the 5' end. The linkered molecule is cut with SpH I and ligated into pBTA297 cut with Bam HI and Sph I to give pBTA305. This intermediate expresses the pre pro A subunit as a fusion protein. The inhibin DNA sequences can be excised as a Hind III-Hind III fragment or as an Eco RI—Eco RI fragment for subsequent manipulation. In particular, this Eco RI—Eco RI fragment can be subcloned into pUC8 or pUC9 and the inhibin cDNA sequences excised as a Bam HI—Bam HI fragment for expression in eukaryote cells using the vector pZIP Neo SV(X)1. (Cepko, C. L. et al. (1984) Cell 37, 1053–1062). This expression system is expected to yield secreted and glycosylated forms of the 43 kD protein in contrast to the prokaryote systems described earlier.

Thus the 5' Pvu II, Sau 3A I and Sph I sites all provide convenient linker sites for expression of the 43 kD protein. The Hae II site starting at base 734 provides a convenient point for expression of the $A_C$ portion of the A subunit starting at arginine 165.

It has been expressed as β-galactosidase fusion products in pUR290, pBTA286 and pUC13 by use of the Hae II site linkers described in FIG. 11A iii. In order to achieve this, the required Hae II-Sau 3A I fragment from pBTA30 was purified and linkers added. The resulting constructions wee cut with Sau 3A I then the DNA was precipitated twice with isopropanol which is efficient in precipitating large DNA fragments, but which precipitates small DNA fragments such as linkers inefficiently. The precipitated DNA was redissolved in TE and ligated into pUR290. The plasmids were transformed into BTA634. The resulting clones were replicated onto duplicate filters then one filter of each pair was screened as described in Example 4 with [$^{32}$P]-labelled Hae II linker (top strand of the DNA pair shown in FIG. 11A iii and the other with Probe 4 (FIG. 3). Clones that were detected by both probes were picked and tested for expression by Western blotting analysis. One such clone is shown in FIG. 13, Track 7 and has been designated BTA421 (Table 2). The DNA fragment encoding the inhibin $A_C$ subunit and its flanking β-galactosidase DNA sequences has also been excised as an Eco RI fragment and ligated into pBTA286 for expression as a fusion protein which is again insoluble, so conferring advantages of purification and protection from degradation. This strain has been designated BTA422, (ATCC67059, Table 2; FIG. 13, Track 2).

The new Bam HI-Sau 3A I fragment encoding the $A_C$ subunit has also been excised from pBTA298 and subcloned into pUC13 in order to generate a short fusion protein. Strain BTA427 (ATCC67056; Table 2) produces this protein as an inclusion body and gel analysis shows (FIG. 13, Track 15) that again, as with BTA426, the longest fusion protein is also the most abundant and the most visible in Western blot analysis indicating BAT427 to be a superior host-vector combination for production of inhibin-like protein.

A notable feature of each of the linkers shown in FIG. 11 is that when the DNA is correctly expressed from the Bam HI site, the amino acid sequence Asp-Pro is incorporated into the fusion protein. As mentioned above, this sequence is labile in formic acid an can be used to cleave the inhibin protein from the protein upstream (Nilsson, B. et al., (1985) Nucl. Ac. Res. 13; 1151–1162) there being no Asp-Pro sequence in the A subunit protein. It is also possible to incorporate other means of cleaving a given sequence from a fusion protein. Examples include incorporation of protease recognition sequences; for example Factor $X_a$ recognition sequences (Nagai, K. and Thogerson, H. C. (1984) Nature 309, 810–812) or collagenase recognition sequences (Sermino, J. and Bastia, D. (1984) Proc. Natl. Acad. Sci. USA 81, 4692–4696) and the possibility of using enzymes which recognise paired arginine residues has been discussed previously (see Example 9). By incorporating a methionine before the inhibin sequences above it is possible to cleave the fusion product with cyanogen bromide to obtain inhibin fragments free of β-galactosidase. Methionine residues within the inhibin sequences may be converted to alternative amino acids by in vitro mutagenesis of the cDNA and thus increase the utility of the cyanogen bromide cleavage technique because a full length inhibin-like protein would be freed from the fusion protein precursor. Conversion of the internal methionine residues may also result in a molecule with more desirable antigenic properties or inhibin-like agonist or antagonist properties.

b. Expression of the 15 kD subunit. The 510 bp Pst I cDNA fragment of pBTA293 (FIG. 4) was ligated into the Pst I site of pUR291 then the plasmids were transformed into E. coli BTA634. The resulting clones were screened for the presence of recombinant plasmids using the 24-fold degenerate 14 mer oligonucleotides that had been used initially to isolate pBTA293 and pBTA294 (Probe 2, FIG. 3). Several recombinant plasmids were then mapped using the restriction enzyme Hind II and two plasmids that contained the insert in the correct orientation were analysed for expression on polyacrylamide gels. One such strain has been designated BTA423 (Table 2).

The 510 by Pst I cDNA fragment of pBTA293 was cloned directly into the Pst I site of pBTA286 and transformed into BTA634 for expression as a fusion product. pBTA286 was derived from pUR291 so the reading frame across the Pst I site allows this direct cloning. The resulting strain is designated BTA424 (ATCC67058; Table 2) and produces the fusion product as an inclusion body.

The 510 bp Pst I cDNA fragment of pBTA293 was also cloned into the Pst I site of pUC8 and transformed into BTA637 for expression as an insoluble short fusion protein creating strain BTA1360 (ATCC67055; Table 2).

Neither of the fusion proteins from BTA423 nor BTA424 nor BTA1360 were detected by the rabbit anti-inhibin antiserum (FIG. 13, Tracks 1, 6 and 16) although each of the A and $A_C$ subunit fusions were. This indicates that the level of antibodies to the 15 kD protein is extremely low or zero and it seems likely therefore that the biological effects associated with immunisation against inhibin can be achieved using the A or $A_C$ subunits alone (see also Examples 17–20).

Expression of the 15 kD sequence may also be achieved by isolation of the Hae II fragment that spans the whole of the 15 kD sequence plus arginines −5 to −1 and by adding the Hae II site linkers described in FIG. 11A iii. The resultant fusion codes as shown in FIG. 11B i and as described above, is useful for expression of a β-galactosidase fusion in pUR290/pUC7/pUC13 using the Bam HI site, with the potential for formic acid cleavage of the fusion of the Asp-Pro sequence. Additionally the Cla I site is useful for expression in ptrpL1 (Edman, J. C. et al. (1981) vide supra) where the ATG acts as a new translational initiation site.

A third possibility for expression is to utilise the unique Hind II site and to synthesise the DNA sequence encoding amino acids 1 to 8 with the desired linkers and Met −1 sequence as shown in FIG. 11B ii.

Thus, the Pst I, Hae II and Hind II sites are all convenient sites for the addition of expression linkers. It is also possible to use the Hae III site (GGCC) spanning amino acids 1 and 2 after a partial Hae III digestion of the 510 bp Pst I fragment. Again, variations on the expression systems are well known to those skilled in the art, and the possibilities described for the A and $A_c$ subunits above are applicable to the B subunit also.

It is also obvious that parts of the subunit precursors can be expressed independently of the inhibin $A_c$ and B subunit sequences in order to study their function. For example, the $A_N$ fragment DNA can be isolated as a Sph I-Hae II (partial) fragment and expressed in pUC7 or pUC13 using linkers shown in FIG. 11A i and 11A iii in order to convert both ends to Bam HI sites.

Furthermore, it is to be understood that expression of inhibin proteins or inhibin-like proteins or peptides need not be restricted to the examples indicated above. There are many different expression systems, useful in prokaryote and eukaryote cells, well known to those experienced in the art, which are suitable for expression of the sequences given here.

Since the amino acid sequences of bovine and human B subunits are identical, it is obvious that, in having expressed the cDNA encoding the bovine B subunit, the product is identical to that which would be obtained by similar expression of the human DNA sequence. Thus strains BTA423, BTA424 and BTA1360 should also be considered to produce the B subunit of human inhibin.

EXAMPLE 11

Isolation of Anti Inhibin Antibodies

Protein fractions containing the β-galactosidase-inhibin fusion proteins from BTA410 and BTA415 were linked to Sepharose CL-6B using the carbonyldiimidazole method (Bethell, G. S. et al. (1979) J. Biol. Chem. 254; 2572–2574) and antibodies to each of the fusion proteins were isolated from 1 ml of the rabbit anti-inhibin antiserum by affinity purification. The absorbed antibodies were eluted from the column with 3M $MgCl_2$ and dialysed against 10 mM Tris-HCl/150 mM NaCl pH 7.5.

The eluted antibodies were used in Western blotting analysis of each of the fusion proteins and were shown to bind only to the fusion protein against which they had been isolated, i.e. there was no cross-reactivity and the amount of anti β-galactosidase antibodies compared to anti-inhibin antibodies was negligible. Similar experiments were performed with the fusion proteins from strains BTA425, 420, 422 and 424.

These experiments demonstrate that recombinant inhibin or inhibin-like proteins can be used to purify anti-inhibin antibodies, to screen monoclonal or polyclonal antibody preparations for anti-inhibin antibodies and as standards in inhibin assay systems such as ELISA's and RIA's.

EXAMPLE 12

Synthesis of Synthetic Peptides

An alternative to the production of inhibin-like proteins in prokaryote and eukaryote cells is to synthesise part or all of inhibin chemically. Such synthetic peptides may be used as analogues, agonists and antagonists of inhibin and have uses as described in Examples 10 and 11.

The following procedure was adapted for the synthesis, purification and characterisation of synthetic peptides. A model 430A peptide synthesiser (Applied Biosystems Inc.) was used. Version 1.00 software was used unmodified from the manufacturer. All reagents were supplied by Applied Biosystems. The reaction vessel was charged with the C terminal amino acid (0.5 mmol) which was supplied covalently attached to the PAM resin. The synthesis was monitored with a ninhydrin reaction after each residue was coupled. The overall yield of resin bound peptide was typically 75%

Cleavage of the peptide from the resin and deprotection was achieved by treating the resin bound peptide with hydrofluoric acid (10 ml) in the presence of the scavengers cresol (0.5 ml) and thiocresol (0.5 ml) at 0° C. for 1 hour. This cleavage and deprotection was performed in a Teflon HF-Reaction Apparatus (Protein Research Foundation, Osaka, Japan). The reaction product was triturated in ether (3×50 ml), filtered, then the peptide was dissolved in acetic acid (10%), filtered and the filtrate was lyophilised.

The residue was dissolved in trifluoroacetic acid (0.1%) containing acetonitrile (10%). The peptide was purified to homogeneity by reverse phase high pressure liquid chromatography. A gradient was developed using trifluoroacetic acid (0.1%) with the percentage of acetonitrile increasing linearly from 10 to 80.

An Altex C8 column was used for analytical chromatography and the eluate was monitored continuously at 220 nm at a flow rate of 1 ml/min. Preparative RP-HPLC was performed with a Vydac Protein and Peptides $C_{18}$ column (Cat. No. 218TP1010) operating at 2–4 ml/min. The gradient was adjusted to optimise the purification of each peptide. Purified peptides were recovered by evaporating the acetonitrile then lyophilising the aqueous phase.

Synthetic peptides were subjected to amino acid analysis using a Waters Pico-Tag System. The protocol provided by the manufacturer was adopted and the system calibrated with PTC amino acids. The amino acid composition of each peptide was consistent with the expected ratios for each amino acid.

Two regions of the A subunit amino acid sequence as derived from the cDNA sequence were initially used in the generation of synthetic peptides. The first from His 1 to Ala 26 and the second from Ser 167 to Asp 195, thus covering the N-termini of the 43 kD (A) and 20 kD ($A_C$) subunits of inhibin. The sequence of Peptide 1 is given in full below where the numbers are those designated for the amino acid sequence given in FIG. 5.

Peptide 1.

```
His-Ala-Val-Gly-Gly-Phe-Met-Arg-Arg-
 1   2   3   4   5   6   7   8   9

Gly-Ser-Glu-Pro-Glu-Asp-Gln-Asp-Val-
10  11  12  13  14  15  16  17  18

Ser-Gln-Ala-Ile-Leu-Phe-Pro-Ala-Lys
19  20  21  22  23  24  25  26
```

Its sequence can be abbreviated to $(H_1-A_{26})K$ using a single letter amino acid code and where the amino acids in brackets represent inhibin sequences as enumerated in FIG. 5.

Peptide 2 is $Y(H_1-A_{26})K$. It is derived from Peptide 1 by the addition of an $NH_2$-terminal tyrosine. A single synthesis was performed commencing with lysine. A portion (75%) of the resin was removed (Peptide 1) and a tyrosine residue was added to the remaining 25% of the peptide in order to generate Peptide 2. The lysine residue was incorporated to facilitate the preparation of haptens and the tyrosine was added to provide a site for radioactive iodination.

EXAMPLE 13

Production and Purification of Inclusion Bodies

Strains BTA420, BTA422 and BTA424 produce inhibin-like proteins as fusion products. The proteins from all three strains are found in vivo as insoluble agglomerates termed inclusion bodies and have been produced and purified by the following procedure.

Overnight cultures were diluted 1:50 into 2×1 litre fresh LB (10 g tryptone/5 g yeast extract/5 g NaCl per litre) in 2 litre baffled flasks and shaken at 37° until the culture density reached OD 0.3–0.4. Isopropyl-B-D-thiogalactosidase (IPTG; 0.1 mM final conc.) was added and incubation continued for 2–7 hrs. Inclusion bodies were first visible as phase bright granules after 2 hrs and empirically reached maximum size and numbers after 7 hrs.

The cells were harvested and the pellet frozen for convenience overnight at −80° C. The cells were resuspended in 20 ml $H_2O$ per liter original culture and broken by use of a French Press. The suspension was made 0.1 mM in phenylmethylsulfonyl fluoride (PMSF) and 5% Triton X-100 then centrifuged at 1,200×G for 10 minutes.

The supernatant was discarded and the pellet resuspended by ultrasound in 50 ml 1M NaCl/5% Triton X-100 and recentrifuged. This washing stage was repeated and the pellet finally resuspended using ultrasound in 2.5 ml 1M NaCl/5% Triton X-100 per liter original culture.

The suspension was layered on a 60% (w/v) sucrose density gradient and centrifuged at 32,000×G for 60 min in a Beckman SW28 rotor. The inclusion bodies were pelleted through the sucrose cushion and freed from cell debris. They can be washed in $H_2O$ and stored frozen at −80° C. for at least 3 months with no change in protein profile as seen on polyacrylamide gels.

EXAMPLE 14

Preparation of Antigens

Purified inclusion bodies were dissolved at 2 mg/ml in 8 M urea/0.1 M DTT/0.1 M Tris HCl pH8.0 under $N_2$ at 37° C. for 2 hrs. The solution was centrifuged at 12,000 rpm for 15 min and the supernatant dialysed against at least 2×5 litre changes of 50 mM $NaH_2PO_4$/150 mM NaCl pH7.5 (PBS) at 4° C. overnight. The protein content of the dialysis bags formed a white floc and was used without further purification. This material contained no pyrogens or lipopolysaccharides as shown by injection of 1 mg intraperitoneally into mice.

The floc suspensions were emulsified with an equal volume of an oil based adjuvant namely Marcol 52: Montanide 888 (9:1) to give a final concentration of 100–250 μg antigen per mol. Where antigens from two or more sources were present, the concentration of each was equal at 100–250 μg/ml.

Synthetic peptides were coupled to keyhole limpet haemocyanin (KLH) by the glutaraldehyde method (Briand, J. P. et al. (1985) J. Immunol. Methods 78, 56–69) and the conjugates emulsified as described above.

It is to be understood that there are many alternative means of preparing an antigen and many alternative routes and regimes of immunisation. Alternative means of preparing antigens include emulsification in Freund's Complete or Incomplete adjuvant, emulsification is alhydrogel or in saponin, or maceration of polyacrylamide gel segments containing the antigen. Alternatively, the antigen may be administered in the absence of adjuvants. Administration routes include oral presentation, presentation through any mucous membrane, intramuscular, intraperitaneal and subcutaneous. Also, there are many alternative means of increasing the antigenicity of a peptide or protein including cross-linking it to itself, cross-linking it to other proteins and modifications of residues or alteration of sequence.

EXAMPLE 15

Immunisation Regime

Animals were given a primary injection (week 0) and a booster 4 weeks later, with the doses of each floc antigen calculated as:

| Rabbits | 100 | μg/dose |
| Sheep | 250 | " |
| Pigs | 200–250 | " |
| Rats | 100 | " |

In addition, the synthetic peptides (Peptide 1; Example 10) coupled to keyhole limpet haemocyanin (KLH) were used in rabbits at 100 μg conjugate per dose.

EXAMPLE 16

Analysis of Antisera

Regular blood samples were taken; a typical bleeding regime includes one bleed before the first injection, one or more bleeds before the booster and weekly bleeds at, and following, the booster. The blood was allowed to clot overnight at 4° C. and the serum removed following centrifugation. The serum was distributed into aliquots and stored frozen at −20° C. pending analysis of antibody and FSH titres.

The sera were tested in 3 different experimental situations:

a. Tracer Building—The ability of antibodies to bind to iodinated 58 kD and 31 kD inhibin was determined, thus indicating whether the antibodies could recognise native bovine inhibin. The tracer antibody complexes were precipitated by use of a second antibody and the radioactivity in the pellet expressed as a percentage of the total counts in the reaction.

The iodination procedure was as follows. Purified 58 kD or 31 kD inhibin (1–2 μg in 25 μl electroelution buffer (International Patent Application PCT/AU85/00119) was added to 25 μl 0.5 M phosphate buffer, pH 7.2. Na$^{125}$I (0.5 mCi, 5 μl, Amersham, Bucks, UK) was added. Chloramine T (40 μl) was added at a ratio of 8:1 Chloramine T to hormone. The reaction proceeded for 60 seconds at room temperature with stirring and was terminated with 20 μl sodium metabisulphite (3 mg/ml). The reaction mixture was made up to 500 μl in 20 mM phosphate buffer/0.1% BSA or 0.5% Polypep pH 6.0 and gel filtered on a Sephadex G25 column (PD10, Pharmacia, Uppsala, Sweden) to remove free $^{125}$I. The void fractions were pooled, made up to 20 ml and applied to a column of 200 μl Matrex Red A (Amicon, danvers, Mass., USA) and then washed with phosphate buffer containing 400 mM KCl, the eluted counts being discarded. $^{125}$I-inhibin was eluted with 1 M KCl/4 M urea in phosphate buffer. The iodinated inhibin was further gel filtered on a Sephadex G25 column (PD10) with the appropriate RIA buffer (see below) to remove the KCl/urea.

Following iodination of 58 kD and 31 kD inhibin, 60 μCi and 25 μCi respectively were recovered in the void volume fractions following gel chromatography on Sephadex G25. Approximately 30% was eluted with the 1 M KCl/4 urea buffer. $^{125}$I-inhibin, as assessed by its molecular weight on SDS-PAGE, was found in this fraction.

The specified activity of the iodinated preparations was assessed in the radioimmunoassay using a self-displacement procedure (Marana et al. (1979) Acta Endocrinal (Kbh.) 92, 585–598) with the hormone used for iodination as standard. Specific activities of 50–60 μCi/μg for $^{125}$I-58 kD inhibin and 24 μCi/μg for $^{125}$I-31 kD inhibin were obtained with recoveries ranging from 5–25%.

The anti-inhibin antiserum from rabbit 474 that had been immunised with native 58 kD inhibin neutralises native inhibin bioactivity, binds strongly to iodinized 58 and 31 kD inhibin, but poorly to separate subunits of either inhibin thus indicating that iodination has not resulted in major conformational changes in the molecule. Therefore the ability of a test antiserum to bind to iodinated inhibin is taken as the ability of that antiserum to recognise native inhibin.

b. In vitro-bioassay—The ability of the antisera to inhibit native inhibin bioactivity in the bioassay described previously (International Patent Application PCT/AU85/00119) indicates that neutralising antibodies are present.

c. FSH—The serum levels of ovine FSH were determined by a radioimmunoassay procedure consisting of a rabbit anti-ovine FSH serum and iodinated ovine RSH as tracer. The serum levels of rabbit FSH were determined by a radioimmunoassay consisting of a guinea pig anti-rabbit FSH serum and iodinated rabbit FSH as tracer. Increases in FSH titre are expected upon removal of endogenous inhibin from the circulation by antibodies raised against recombinant material.

EXAMPLE 17

Sheep Experiments

Groups of 9 animals (Corriedales; a breed chosen to be in anoestrus for the duration of the experiment) were immunised with single or paired floc antigens as shown in Table 4 and the sera analysed as described in Example 16.

a) Tracer binding studies. Nineteen animals produced sera (taken 2 weeks post-booster) which had significant tracer binding capacity (Table 6). These animals all came from groups other than the placebo control (group A) and the group immunised with the 15 kD subunit fusion protein from pBTA301 (Group C). The best response was in animal 673 (Group D) which showed 10% binding to 31 kD tracer and 3.1% binding to 58 kD tracer at 1:1000 dilution.

TABLE 6

TRACER BINDING EXPERIMENTS WITH SHEEP ANTISERA

| GROUP | ANTIGEN SOURCE | SUBUNIT | ANIMAL | TRACER | % TRACER BOUND |
|---|---|---|---|---|---|
| A | BTA425 | — | — | — | — |
| B | BTA420 | 43 kD | 577 | 125$_{I-58\ kD}$ | 4.2 |
|   |   |   | 669 | " | 1.4 |
|   |   |   | 583 | " | 2.0 |
|   |   |   | 658 | " | 2.3 |
|   |   |   | 643 | " | 3.1 |
|   |   |   | 585 | " | 2.8 |
|   |   |   | 658 | " | 2.3 |
|   |   |   | 657 | " | 1.8 |
| C | BTA424 | 15 kD | — | — | — |
| D | BTA422 | 20 kD | 656 | 125$_{I-31\ kD}$ | 1.0 |
|   |   |   | 589 | " | 1.7 |
|   |   |   | 673 | " | 10.0 |
|   |   |   | 673 | 125$_{I-58\ kD}$ | 3.1 |

TABLE 6-continued

TRACER BINDING EXPERIMENTS WITH SHEEP ANTISERA

| GROUP | ANTIGEN SOURCE | SUBUNIT | ANIMAL | TRACER | % TRACER BOUND |
|---|---|---|---|---|---|
| E | BTA420 + BTA424 | 43 kD + 15 kD | 592 | $125_{I\text{-}58 \text{ kD}}$ | 2.3 |
|   |   |   | 652 | " | 2.8 |
|   |   |   | 624 | " | 4.3 |
|   |   |   | 570 | " | 2.7 |
|   |   |   | 628 | " | 2.4 |
|   |   |   | 663 | " | 1.7 |
| F | BTA422 + BTA424 | 20 kD + 15 kD | 661 | $125_{I\text{-}31 \text{ kD}}$ | 1.0 |
|   |   |   | 666 | " | 1.0 |

All animals not shown had less than 1% binding.

Therefore recombinant inhibin subunits, when used as antigens, have the potential to raise antisera in sheep capable of recognising native inhibin. It should be pointed out that
i) these experiments detect those antibodies free in the sera, and it is possible that the antibodies with highest affinity for sheep inhibin are actually bound to sheep inhibin so would not be detected in this assay, and ii) the screening was performed at 1:1000 dilution which is likely to be beyond the dilution titre of weaker positive sera.
b) In vitro bioassay data. None of the sera showed in vitro neutralisation of inhibin activity in the pituitary cell culture bioassay under the conditions tested (1 µl antiserum per 2 U inhibin)
c) FSH titres. The serum FSH levels for each animal group are shown in Table 7. No significant differences were observed between bleeds for the control group (A) but a significant, albeit transient, increase was observed for all but one of the test groups.

Therefore recombinant inhibin can be used as an antigen to increase FSH titre in domestic animals. As FSH is known to increase ovulation rate, immunisation against recombinant inhibin can therefore be expected to increase ovulation rate and be used as a fecundity agent for the improvement of reproductive efficiency. It also follows that administration of bioactive recombinant inhibin will suppress FSH levels and thus have potential for use as a contraceptive in both males and females since FSH is involved in the control of spermatogenesis in males and folliculogenesis in females.

TABLE 7

SHEEP SERUM FSH LEVELS

| | WEEK | | | | |
|---|---|---|---|---|---|
| GROUP | 0 (Primary) | 4 (Booster) | 5 | 6 | 7 |
| A | 8.7 ± 1.5 | 10.1 ± 3.3 | 9.6 ± 3.7 | 10.9 ± 3.6 | 10.6 ± 5.2 |
| B | 7.8 ± 3.6 | 8.0 ± 2.5 | 13.2 ± 6.0* | 10.5 ± 6.2 | 6.9 ± 2.8 |
| C | 5.5 ± 2.4 | 7.2 ± 3.6 | 11.6 ± 6.7 | 12.4 ± 6.5* | 11.0 ± 4.7* |
| D | 8.5 ± 3.6 | 7.9 ± 2.5 | 9.7 ± 4.8 | 12.7 ± 4.5** | 10.7 ± 4.2 |
| E | 8.8 ± 2.4 | 9.8 ± 3.9 | 10.5 ± 2.6 | 10.8 ± 3.1 | 9.3 ± 3.5 |
| F | 8.4 ± 3.1 | 9.7 ± 5.0 | 8.4 ± 5.7 | 11.6 ± 6.4* | 9.6 ± 3.5 |

Results shown are group mean ± standard deviation.
The groups are as shown in Table 4. Statistical comparisons were made between week 4 values and values for subsequent weeks in a paired t-test between animals in the same group.
*p < 0.05
**p < 0.01

EXAMPLE 18

Rabbit Experiments

Antisera from non-castrate male rabbits, that had been immunised with either native 58 kD or 31 kD inhibin, or with fusion proteins from cells carrying plasmids pBTA297, 299 or 301, or with a conjugate protein containing synthetic Peptide 1 (Example 10) were analysed in the tracer binding system. The results are given in Table 8.

TABLE 8

TRACER BINDING EXPERIMENTS WITH RABBIT ANTISERA

| | | % TRACER BOUND | |
|---|---|---|---|
| RABBIT | ANTIGEN SOURCE | 58 kD | 31 kD |
| 474 | 58 kD Native | 25.2 | 28.5 |
| 461 | 31 kD Native | 4.0 | 5.8 |
| 692 | BTA420 | 3.2 | 0 |
| 693 | " | 23.2 | 0 |
| 694 | " | 7.2 | 0 |
| 464 | BTA422 | 0 | 0 |
| 465 | " | 0 | 0 |
| 466 | " | 0 | 0 |
| 695 | BTA424 | 0 | 0 |
| 696 | " | 0 | 0 |
| 697 | " | 0 | 0 |
| 698 | Peptide 1 | 3.8 | 0 |
| 699 | " | 13.9 | 0 |

The serum from animal 474 was used at 1:2000 dilution whereas all the rest were used at 1:1000.

These data again show that recombinant inhibin subunits and a synthetic peptide are capable of eliciting an antibody response which includes antibodies that can recognise and bind to native inhibin. Responses vary from animal to animal but the failure of the recombinant 15 kD antigen (from BTA424) to elicit a significant response in all rabbits tested reflects the fact that all antibodies in the serum from rabbit 474 (which were raised against native 58 kD inhibin) appear to be directed against the 43 kD subunit in tests so far conducted and therefore implies that the 15 kD subunit is only poor antigenic in rabbits. It does not imply that this subunit will not be useful in other species. These results also suggest that in order to generate a significant antigenic response to the 15 kD subunit, some modification of its structure or sequence or presentation will be necessary. Similary, the kD subunit is a poor antigen in rabbits.

The serum FSH levels of rabbit 699 showed a dramatic decrease to zero following the booster immunisation with the Peptide 1-KLH conjugate antigen (FIG. 15) and those of rabbit 698 a gradual decline. The response of each animal correlates with the titre of its antserum against 58 kD tracer. Furthermore the synthetic peptide itself or the antisera directed against it were without effect in the vitro rat pituitary cell bioassay indicating them to have no direct effects on the inhibin receptor. This peptide and derivatives thereof, therefore have potential for use as contraceptives in both males and females since FSH is involved in spermatogenesis and folliculogensis (See Example 19). Furthermore, since this is the $NH_2$-terminus of the $A_N$ fragment, it follows that the $A_N$ fragment itself or other synthetic peptides derived from the $A_N$ fragment of the cow, human or other vertebrate species may also find similar use assuming that the observed response is antibody-mediated. It also follows that administration of a bioactive $A_N$ fragment or part thereof in a manner other than an antigen is expected to increase FSH levels and thus act as a fecundity agent for the improvement of reproductive efficiency (see also Example 19)

EXAMPLE 19

Pig Experiments

The protocol for this experiment differed from that described previously.

Selected gilts (aged 22–23 weeks) were immunised with 750 μg of the β-galactosidase floc antigen from BTA425 (16 animals, control group) or with a mixture containing 250 μg of each subunit floc antigen from BTA422, BTA424 and BTA426 (16 animals, test group). A similar booster was given at 25 days and again at 47 days after the primary injection. Sera were taken at 60 days after the primary injection and analysed for anti-inhibin antibodies by the tracer-binding method. The gilts were observed for signs of oestrus and mated at the earliest opportunity after day 60.

Sera from 15 test group animals were assayed for tracer binding capacity at 1:100 dilution and 10 of these showed binding to $^{125}$I-58 kD inhibin in the range 1.7–9.0% ($\overline{X}$=4.9±2.5). One serum with 2.0% binding to $^{125}$I-58kD inhibin also showed 6.4% binding to $^{125}$I-31 kD inhibin. None of the 6 control sera tested had significant binding to either tracer demonstrating that recombinant inhibin subunits are capable of eliciting an antigenic response in pigs that results in antibodies that can recognise native inhibin.

The pig oestrus cycle is 21 days so 27 days after the day 60 bleed, all animals in the trial were expected to have shown signs of oestrus and therefore to have been mated. Table 9 shows the mating data for control and test groups. A $\chi^2$ analysis reveals the treatment to have had significant effect results in many of the test group animals not being mated.

TABLE 9

$X^2$ ANALYSIS OF MATING DATA

| GROUP | MATED | NON-MATED | TOTAL |
|---|---|---|---|
| Control | 14 | 2 | 16 |
| Test | 6 | 10 | 16 |
| Total | 20 | 12 | 32 |

$X^2$ = 6.5;
p < 0.02 applying Yates correction.

It is possible that this data reflects the role of antibodies against the $A_N$ fragment of 58 kD inhibin since 9 of the 10 sera with anti-58 kD inhibin antibodies failed to detect 31 kD inhibin at 1:100 dilution indicating a large proportion of the antibodies to be $A_N$ specific. This postulate is supported by the observation in rabbits that administration of Peptide 1 as an antigen caused a fall in FSH levels (Example 18) one consequence of which in female vertebrates would be the cessation of cycling and folliculogenesis. The one animal that produced a serum with higher antibody titre against 31 kD inhibin than 58 kD inhibin was mated normally during this period. Other explanations are also possible; for example, the 43kD antigen contains amino acids −10 to −1 of the pre pro A subunit and it is possible that this sequence is responsible for the effect. Nevertheless, by whatever mechanism this paradoxical result was achieved in vivo, the data serve to emphasise the role of inhibin as a regulator of FSH and hence of reproductive physiology and processes and it substantiates a role for recombinant inhibin as a contraceptive in males and females and as a molecule for the prevention of cycling in females.

EXAMPLE 20

Rat Experiments

Groups of rats were immunised in a regime similar to that used for sheep. The sera were analysed in the iodinated tracer binding assay at 1:500 dilution and the % binding data from each group presented as mean±standard deviation in Table 10. The antigens used for groups (A–F) are as given in Table 6.

TABLE 10

TRACER BINDING EXPERIMENTS WITH RAT ANTISERA

| | | | TRACER | |
|---|---|---|---|---|
| GROUP | SEX | NUMBER | 58 kD | 31 kD |
| A | M | 9 | 1.06 ± 0.26 | 0.38 ± 0.58 |
|   | F | 10 | 0.55 ± 0.45 | 0.82 ± 0.62 |
| B | M | 9 | 7.00 ± 3.50 | 0.52 ± 0.50 |
|   | F | 9 | 4.17 ± 4.84 | 0.82 ± 0.49 |
| C | M | 9 | 0.54 ± 0.53 | 0.67 ± 0.51 |
|   | F | 10 | 0.66 ± 0.72 | 0.79 ± 0.70 |
| D | M | 9 | 1.10 ± 0.74 | 1.46 ± 0.96 |
|   | F | 10 | 0.89 ± 0.83 | 1.55 ± 0.37 |
| E | M | 10 | 8.30 ± 5.00 | 0.79 ± 0.58 |
|   | F | 10 | 4.50 ± 2.65 | 0.98 ± 0.69 |
| F | M | 9 | 0.51 ± 0.61 | 0.85 ± 0.59 |
|   | F | 10 | 0.66 ± 0.72 | 0.79 ± 0.70 |

These data show again that the A (43 kD) subunit is a better antigen than the $A_C$ (20 kD) subunit by comparing tracer binding ability of group A with group B and E or group D. The B subunit was ineffective as an antigen as assessed by tracer binding studies. These results reinforce the observation that 58 kD native inhibin generated a good antibody response and neutralising antibodies in rabbit 474 whereas no neutralising antibodies and a poor antigenic response was observed in rabbit 461 and two others immunised with 31 kD native inhibin.

As with other species (sheep, rabbits, pigs) in none of the animals immunised with recombinant inhibin subunits were neutralising antibodies detected. Furthermore, in all species, a large immune response against the β-galactosidase portion of the antigen was observed. These observations suggest that conformational epitopes may be important and that antigens such as those from BTA426, BTA427, and BTA1360 or from the tip vectors (Example 10) will be of value since the β-galactosidase portion of the fusion is substantially reduced (FIG. 12) or absent and experiments can be undertaken in order to generate conformational epitopes and to improve antigen presentation.

Nevertheless, the animal experiments presented herein establish that recombinant inhibin, subunits, fragments and synthetic analogues or homologues thereof can be used—
a) to generate antibodies that recognise native inhibin
b) to alter FSH levels
c) to have use as fecundity agents or contraceptives.

EXAMPLE 21

Production Methods for Inhibin

Host cells which contain the recombinant plasmids carrying the genetic information for the production of inhibin are maintained as freeze-dried vials in the production culture collection. Cells from the storage vial are reconstituted and plated out on a selective medium, and the cells from this medium are used to prepare fermentor inocula. The inocula are used to seed fermentors containing a suitable growth medium and the fermentation proceeds under conditions appropriate for the production of the inhibin proteins. At the completion of the fermentation the cells are harvested and the product is released from the cells and undergoes purification. The product is subjected to analyses and quality control, and is stored under conditions appropriate for good stability. The product is formulated for use by combinations with other ingredients under conditions of strict hygiene.

INDUSTRIAL APPLICATION

Uses of Inhibin

Inhibin or parts thereof produce by the present invention may be used either as antigens or as bioactive compounds; the effects due to one method of use are expected to be opposite to those produced by the other method of use.

In one form inhibin or parts thereof produced by the present invention and/or modified subsequently can be used as an antigen and thus be used to affect fertility. Elevation of ovulation rates in vertibrates including humans would improve fertility and thus increase fecundity or improve reproductive efficiency. Products of the invention could be used to increase ovulation rate and would thus find use in in vitro fertilisation programmes, such as for domestic animals or humans. It could also be used in non-domestic animals, for example to facilitate breeding programmes in zoos. Moreover, the products of the invention could be used to advance sexual maturation or puberty so as to increase reproductive lifetime and/or to advance oestrus in production animals so as to decrease the period between farrowing and mating and/or to reduce seasonal or post partum anoestrus. In males, the products of the invention could be used to stimulate spermatogenesis.

The production of farmed species such as cows, sheep, pigs, goats, deer, horses, fish and chickens thus may benefit from these applications of inhibin.

Inhibin as an active agent could be used as a means of controlling ovulation in females or suppressing spermatogenesis in males and thus used as a contraceptive agent or means to synchronise ovulation.

Parts of inhibin, for example synthetic peptides or $A_N$ fragment, may be used as antigens to suppress FSH levels and thus to act as contraceptive or molecules for suppressing oestrus.

As the products of the present invention can be used to raise antibodies, and these also form part of the present invention, anti-inhibin antibodies could be used as diagnostic agents. For example, such uses include means to monitor the status of the reproductive cycle in vertibrates including humans. In this way time of ovulation and the number of ova shed could be predicted, thus allowing assessment of therapeutic procedures used to affect the reproductive cycle.

The antibodies could be used to assess granulosa cell function in the female, as a marker for sertoli cell function in males and possibly as a marker for genetic selection of good breeders.

Thus recombinant proteins previously described and derivatives or homologues and analogues thereof have many uses which include a) use as antigens or inhibin antagonists in order to down regulate or abolish some or all of the physiological effects due to native inhibin or its precursors in vivo.

b) use as antigens in order to produce monoclonal or polyclonal antibodies.

c) use as precursors for production of a biologically active recombinant inhibin in vivo or in vitro.

d) use as standards in an inhibin radioimmunoassay (RIA) and enzyme-linked immunosorbent (ELISA) assays or assays using other detection systems such as chemilluminescence or fluorescence.

e) use in screening monoclonal and polyclonal antibody preparations f) use in purification of antibodies that recognise inhibin or inhibin-like amino acid sequences (see Example 9).

g) use as inhibin agonists to potentiate some or all of the physiological effects due to native inhibin or its precursors in vivo. Bioactive recombinant inhibin may be produced by co-expressing both subunits or precursors thereof in the same cell or by correctly refolding individual subunits or precursors, analogues, homologues or derivatives thereof in vitro.

The inhibin cDNA sequence have several uses which, by way of example, include:

1) use as cDNA templates for protein synthesis in prokarvote or eukaryote cells (see Example 8).
2) use as DNA templates for the manufacture of radiolabelled inhibin cDNA probes. These probes can be used to detect and isolate inhibin or inhibin-like sequences in the genomic DNA of various species or in the mRNA of cells making inhibin or inhibin-like peptides (see Examples 7 and 8). They thus have potential in diagnosing defects in inhibin synthesis and regulation in man and domestic animals and for the cloning and manipulation of inhibin genes.
3) use as DNA templates for the manufacture of radiolabelled RNA probes for uses similar to 2) above, and
4) use as DNA templates for the manufacture of radiolabelled inhibin.

What is claimed is:

1. A polynucleotide sequence which codes for 58 kD bovine inhibin comprising amino acids His 1 to Ile 300 of FIG. 5 and amino acids Gly 1 to Ser 116 of FIG. 6, or 31 kD bovine inhibin comprising amino acids Ser 167 to Ile 300 of FIG. 5 and amino acids Gly 1 and Ser 116 of FIG. 6, or a precursor or subunit of bovine inhibin selected from the group consisting of a 43 kD subunit which comprises amino acids His 1 to Ile 300 of FIG. 5, a 20 kD subunit comprising amino acids Ser 167 to Ile 300 of FIG. 5, a 15 kD subunit comprising amino acids Gly 1 to Ser 116 to FIG. 6, and an $A_N$ subunit comprising amino acids His 1 to Arg 166 of FIG. 5.

2. A recombinant DNA molecule characterized by a polynucleotide sequence is claimed in claim 1, and vector DNA.

3. A polynucleotide sequence according to claim 1, which on expression codes for the 43 kD subunit of bovine inhibin.

4. A polynucleotide sequence according to claim 1, which on expression codes for the 20 kD subunit of bovine inhibin.

5. A polynucleotide sequence according to claim 1, which on expression codes for the 15 kD subunit of bovine inhibin.

6. A polynucleotide sequence according to claim 1, which codes for bovine inhibin.

7. A molecular probe useful for the indication of bovine inhibin-like RNA or DNA, comprising:

(a) a polynucleotide sequence according to claim 1, or a sequence which hybridises to said polynucleotide sequence in 5×SSC/10×Denhardt's solution, and continues to bind to said polynucleotide sequences after washing the complex in 1×SSC/0.1% sodium dodecyl sulphate at 37° C., and (b) a label for detecting the presence of said sequence.

8. A molecular probe according to claim 7, wherein said label is a radioactive label.

9. A molecular probe according to claim 7, wherein the polynucleotide sequence acts as a coding sequence for a polypeptide having the primary structure shown in FIG. 5 or FIG. 6.

10. The recombinant DNA molecule according to claim 2, wherein the polynucleotide sequence codes for the 43 kD subunit of bovine inhibin.

11. The recombinant DNA molecule according to claim 2, wherein the polynucleotide sequence codes for the 20 kD subunit of bovine inhibin.

12. The recombinant DNA molecule according to claim 2, wherein the polyncleotide sequence codes for the 15 kD subunit of bovine inhibin.

13. The recombinant DNA molecule according to claim 2, wherein the polynucleotide sequence codes for a bovine inhibin.

14. The recombinant DNA molecule according to claim 2, in the form of a plasmid, virus, or bacteriophage DNA.

15. The recombinant DNA molecule according to claim 2, in the form of a plasmid.

16. The recombinant DNA molecule according to claim 2, wherein an expression control sequence is operatively linked to said polynucleotide sequence.

17. The recombinant DNA molecule according to claim 16, wherein said expression control sequence a promoter and a translation start signal.

18. The recombinant DNA molecule according to claim 17, wherein said expression control sequence is selected from the group consisting of the b-galactosidase gene of *E. coli*, the trp operon, the leftward promoter of bacteriophage lambda, and the long terminal repeat of a Moloney leukemia virus.

19. A process for manufacture of a recombinant DNA molecule, which comprises:
 (a) providing a DNA insert comprising a DNA sequence which on expression codes for a polypeptide selected from the group consisting of:
  (i) 58 kD bovine inhibin having the sequence of amino acids His 1 to Ile 300 of FIG. 5 and amino acids Gly 1 to Ser 116 of FIG. 6,
  (ii) 31 kD bovine inhibin having the sequence of amino acids Ser 167 to Ile 300 of FIG. 5 and amino acids Gly 1 to Ser 116 of FIG. 6,
  (iii) 43 kD subunit of bovine inhibin having the sequence of amino acids His 1 to Ile 300 of FIG. 5,
  (iv) 20 kD subunit of bovine inhibin having the sequence of amino acids Ser 167 to Ile 300 of FIG. 5,
  (v) 15 kD subunit of bovine inhibin having the sequence of amino acids Gly 1 to Ser 116 of FIG. 6,
  (vi) $A_N$ subunit of bovine inhibin having the sequence of amino acids His 1 to Arg 166 of FIG. 5,
  (vii) bovine inhibin A subunit having the sequence of amino acids in FIG. 5, and
  (viii) bovine inhibin B subunit having the sequence of amino acids in FIG. 6; and
 (b) cloning said DNA insert into a cloning vehicle to produce a recombinant DNA molecule.

20. The process according to claim 19, wherein said cloning vehicle is a bacterial plasmid, a bacteriophage, or a plasmid of virus capable of replicating in an eukaryotic cell.

21. The process according to claim 19, wherein said DNA insert is introduced into the cloning vehicle in the correct reading frame with an expression control sequence.

22. The process according to claim 19, wherein the cloning vehicle is the b-galactosidase gene of *E. coli*.

23. The process according to claim 19, wherein the DNA sequence codes for a bovine inhibin.

24. A process for transforming a host so that it is capable of producing a polypeptide of bovine inhibin or a precursor thereof, which process comprises providing a suitable host, and introducing into said host a recombinant DNA molecule of claim 2 in correct reading frame.

25. The process according to claim 24, wherein said host is selected from the group consisting of bacteria, yeast, bacteriophage, and eukaryotic cells.

26. The process according to claim 24, wherein the polypeptide is bovine inhibin.

27. A host capable of expressing a polypeptide of bovine inhibin or a precursor thereof, said host being prepared by the process of claim 24.

28. The host according to claim 27, wherein said host is selected from the group consisting of bacteria, yeasts, fungi, and eukaryotic cells.

29. The host according to claim 27, wherein said host is a vertebrate or plant eukaryotic cell.

30. The host according to claim 27, which is capable of expressing at least one of the 43 kD, 20 kD, or 15 kD sub-units of bovine inhibin in non-glycosylated form.

31. The host according to claim 27, wherein the host is an *E. coli* microrganism selected from the group consisting of ATCC 67054, ATCC 67055, ATCC 67056, ATCC 67057, ATCC 67058, AND ATCC 67059.

32. A process for the biosynthesis of a peptide of bovine inhibin or a precursor thereof, which comprises:
 (a) providing a recombinant DNA molecule according to claim 2 which is capable of replication, and which on expression codes for a polypeptide of bovine inhibin or a precursor thereof;
 (b) transforming a host with said recombinant DNA molecule so that said host is capable of expressing a product which includes said polypeptide
 (c) culturing said host to obtain said expression; and
 (d) collecting said polypeptide product.

33. The process according to claim 32, wherein said polypeptide product is formed as an inclusion body.

34. The process according to claim 32, wherein said wherein said polypeptide product consists essentially of at least one of the 43 kD, 20 kD, or 15 kD sub-units of bovine inhibin.

35. The process according to claim 32, wherein said polypeptide product is bovine inhibin.

36. A molecular probe according to claim 7, wherein said probe is selected from the group consisting of:

```
                       T   G
Probe 1     5' C CAT AANCCNCC 3'
                       G   A A  A  T  A
Probe 2     5' CCGAT TC TT AA 3'
                     T  G  C  G Probe 3     5' ACGCCTGACTCCAGA 3'

Probe 4     5' CCTCCAGTTTCATCT 3'

C      C
Probe 5     5' ATGTT ACCTT CCGTC 3'
                       G      G

Probe 6     5' CTTTGAGATTTCCAAAGAAGC 3'.
```

37. The recombinant DAN molecule according to claim 15, wherein the plasmid is selected from the group consisting of NCCB PC V3019, NCCB PC V3029, NCCB PC V3165, NCCB PC V3180, NCCB PC V3249, NCCB PCV3072, NCCB PC V3073, and NCCB PC V3074.

38. The recombinant DNA molecule according to claim 15, wherein the plasmid is selected from the group consisting of AGAL NM00/13784, AGAL NM00/13785, AGAL NM00/13786, AGAL NM00/13787, ATCC 67054, ATCC 67055, ATCC 67056, ATCC 67057, ATCC 67058, and ATCC 67059.

* * * * *